United States Patent
Kelly et al.

(10) Patent No.: US 10,588,682 B2
(45) Date of Patent: Mar. 17, 2020

(54) APPARATUS AND METHODS RELATED TO CONSTRAINED DEPLOYMENT OF CRYOGENIC BALLOONS FOR LIMITED CRYOGENIC ABLATION OF VESSEL WALLS

(71) Applicant: Medtronic Ardian Luxembourg S.a.r.l., Luxembourg (LU)

(72) Inventors: Brian Kelly, Galway (IE); John Kelly, Ballinsloe (IE); Gary P. Kelly, Galway (IE); Barry Mullins, Wicklow (IE)

(73) Assignee: MEDTRONIC ARDIAN LUXEMBOURG S.A.R.L., Luxembourg (LU)

( * ) Notice: Subject to any disclaimer, the term of this patent is extended or adjusted under 35 U.S.C. 154(b) by 1520 days.

(21) Appl. No.: 14/114,345

(22) Filed: Jun. 12, 2014

(65) Prior Publication Data
US 2015/0126986 A1 May 7, 2015

Related U.S. Application Data

(60) Provisional application No. 61/572,288, filed on Apr. 25, 2011.

(51) Int. Cl.
*A61B 18/02* (2006.01)
*A61B 18/00* (2006.01)

(52) U.S. Cl.
CPC .... *A61B 18/02* (2013.01); *A61B 2018/00041* (2013.01); *A61B 2018/00166* (2013.01);
(Continued)

(58) Field of Classification Search
CPC .. A61B 2018/0262; A61B 2018/00023; A61B 2018/0025; A61B 2018/00261
See application file for complete search history.

(56) References Cited

U.S. PATENT DOCUMENTS 3,125,096 A 3/1964 Antiles et al.
3,298,371 A 1/1967 Lee
(Continued)

FOREIGN PATENT DOCUMENTS

CN 202386778 8/2012
CN 202960760 U 6/2013
(Continued)

OTHER PUBLICATIONS

US 8,398,630 B2, 03/2013, Demarais et al. (withdrawn)
(Continued)

*Primary Examiner* — Michael F Peffley
*Assistant Examiner* — Bo Ouyang
(74) *Attorney, Agent, or Firm* — Snell & Wilmer LLP

(57) ABSTRACT

Embodiments related to cryogenically ablating a portion of the inner surface of a vessel by constraining a cryoballoon using various apparatuses and methods are disclosed. For example, a catheter can include a cryoballoon for ablation of the vessel wall and a constraining element disposed substantially in parallel with the cryoballoon to deflect or offset a portion of the cryoballoon away from non-target tissue of the vessel wall and prevent ablation of the non-target tissue. Partial circumferential, non-continuous, or helical ablation can be effective for treating a variety of renal, cardio-renal, and other diseases including but not limited to hypertension, heart failure, renal disease, renal failure, contrast nephropathy, arrhythmia, and myocardial infarction. The constraining element may be, for example, a second inflatable balloon or one or more self-expanding prongs.

19 Claims, 12 Drawing Sheets

(52) U.S. Cl.
CPC .............. *A61B 2018/00244* (2013.01); *A61B 2018/00261* (2013.01); *A61B 2018/00404* (2013.01); *A61B 2018/00434* (2013.01); *A61B 2018/00511* (2013.01); *A61B 2018/0212* (2013.01)

(56) References Cited

U.S. PATENT DOCUMENTS

| | | |
|---|---|---|
| 3,901,241 A | 8/1975 | Allen, Jr. |
| 3,924,628 A | 12/1975 | Droegemueller et al. |
| 4,275,734 A | 6/1981 | Mitchiner |
| 4,483,341 A | 11/1984 | Witteles |
| 4,531,943 A | 7/1985 | Van Tassel et al. |
| 4,602,624 A | 7/1986 | Naples et al. |
| 4,649,936 A | 3/1987 | Ungar et al. |
| 4,709,698 A | 12/1987 | Johnston et al. |
| 4,764,504 A | 8/1988 | Johnson et al. |
| 4,770,653 A | 9/1988 | Shturman |
| 4,784,132 A | 11/1988 | Fox et al. |
| 4,790,310 A | 12/1988 | Ginsburg et al. |
| 4,862,886 A | 9/1989 | Clarke et al. |
| 4,890,623 A | 1/1990 | Cook et al. |
| 4,938,766 A | 7/1990 | Jarvik |
| 4,976,711 A | 12/1990 | Parins et al. |
| 5,034,010 A | 7/1991 | Kittrell et al. |
| 5,053,033 A | 10/1991 | Clarke |
| 5,071,424 A | 12/1991 | Reger |
| 5,074,871 A | 12/1991 | Groshong |
| 5,078,717 A | 1/1992 | Parins et al. |
| 5,098,429 A | 3/1992 | Sterzer |
| 5,102,402 A | 4/1992 | Dror et al. |
| 5,108,390 A | 4/1992 | Potocky et al. |
| 5,109,859 A | 5/1992 | Jenkins |
| 5,125,928 A | 6/1992 | Parins et al. |
| 5,129,396 A | 7/1992 | Rosen et al. |
| 5,156,151 A | 10/1992 | Imran |
| 5,156,610 A | 10/1992 | Reger |
| 5,178,620 A | 1/1993 | Eggers et al. |
| 5,178,625 A | 1/1993 | Groshong |
| 5,190,539 A | 3/1993 | Fletcher et al. |
| 5,190,540 A | 3/1993 | Lee |
| 5,211,651 A | 5/1993 | Reger et al. |
| 5,234,407 A | 8/1993 | Teirstein et al. |
| 5,277,201 A | 1/1994 | Stern |
| 5,282,484 A | 2/1994 | Reger |
| 5,300,068 A | 4/1994 | Rosar et al. |
| 5,304,115 A | 4/1994 | Pflueger et al. |
| 5,304,120 A | 4/1994 | Crandell et al. |
| 5,304,171 A | 4/1994 | Gregory et al. |
| 5,306,250 A | 4/1994 | March et al. |
| 5,326,342 A | 7/1994 | Pflueger et al. |
| 5,333,614 A | 8/1994 | Feiring |
| 5,334,181 A | 8/1994 | Rubinsky et al. |
| 5,342,301 A | 8/1994 | Saab |
| 5,344,395 A | 9/1994 | Whalen et al. |
| 5,345,936 A | 9/1994 | Pomeranz et al. |
| 5,358,514 A | 10/1994 | Schulman et al. |
| 5,368,591 A | 11/1994 | Lennox et al. |
| 5,372,138 A | 12/1994 | Crowley |
| 5,380,319 A | 1/1995 | Saito et al. |
| 2,701,559 A | 2/1995 | Cooper |
| 5,397,301 A | 3/1995 | Pflueger et al. |
| 5,417,355 A | 5/1995 | Broussalian et al. |
| 5,419,767 A | 5/1995 | Eggers et al. |
| 5,423,744 A | 6/1995 | Gencheff et al. |
| 5,425,364 A | 6/1995 | Imran |
| 5,427,118 A | 6/1995 | Nita et al. |
| 5,451,207 A | 9/1995 | Yock |
| 5,453,091 A | 9/1995 | Taylor et al. |
| 5,454,788 A | 10/1995 | Walker et al. |
| 5,474,530 A | 12/1995 | Passafaro et al. |
| 5,484,400 A | 1/1996 | Edwards et al. |
| 5,496,311 A | 3/1996 | Abele et al. |
| 5,498,261 A | 3/1996 | Strul |
| 5,505,730 A | 4/1996 | Edwards |
| 5,507,744 A | 4/1996 | Tay et al. |
| 5,540,679 A | 7/1996 | Fram et al. |
| 5,562,720 A | 10/1996 | Stern et al. |
| 5,571,147 A | 11/1996 | Sluijter et al. |
| 5,588,962 A | 12/1996 | Nicholas et al. |
| 5,588,964 A | 12/1996 | Imran et al. |
| 5,599,345 A | 2/1997 | Edwards et al. |
| 5,609,606 A | 3/1997 | O'Boyle |
| 5,624,392 A | 4/1997 | Saab |
| 5,626,576 A | 5/1997 | Janssen |
| 5,647,847 A | 7/1997 | Lafontaine et al. |
| 5,649,923 A | 7/1997 | Gregory et al. |
| 5,665,062 A | 9/1997 | Houser |
| 5,667,490 A | 9/1997 | Keith et al. |
| 5,672,174 A | 9/1997 | Gough et al. |
| 5,688,266 A | 11/1997 | Edwards et al. |
| 5,693,015 A | 12/1997 | Walker et al. |
| 5,693,043 A | 12/1997 | Kittrell et al. |
| 5,693,082 A | 12/1997 | Warner et al. |
| 5,695,504 A | 12/1997 | Gifford, III et al. |
| 5,700,282 A | 12/1997 | Zabara |
| 5,704,908 A | 1/1998 | Hofmann et al. |
| 5,707,400 A | 1/1998 | Terry, Jr. et al. |
| 5,713,942 A | 2/1998 | Stern et al. |
| 5,749,914 A | 5/1998 | Janssen |
| 5,755,682 A | 5/1998 | Knudson et al. |
| 5,758,505 A | 6/1998 | Dobak, III et al. |
| 5,769,880 A | 6/1998 | Truckai et al. |
| 5,772,590 A | 6/1998 | Webster, Jr. |
| 5,775,338 A | 7/1998 | Hastings |
| 5,779,698 A | 7/1998 | Clayman et al. |
| 5,792,105 A | 8/1998 | Lin et al. |
| 5,797,903 A | 8/1998 | Swanson et al. |
| 5,800,484 A | 9/1998 | Gough et al. |
| 5,807,306 A | 9/1998 | Shapland et al. |
| 5,807,391 A | 9/1998 | Wijkamp |
| 5,810,810 A | 9/1998 | Tay et al. |
| 5,817,113 A | 10/1998 | Gifford, III et al. |
| 5,823,956 A | 10/1998 | Roth et al. |
| 5,829,447 A | 11/1998 | Stevens et al. |
| 5,830,213 A | 11/1998 | Panescu et al. |
| 5,836,874 A | 11/1998 | Swanson et al. |
| 5,837,003 A | 11/1998 | Ginsburg |
| 5,840,076 A | 11/1998 | Swanson et al. |
| 5,843,016 A | 12/1998 | Lugnani et al. |
| 5,846,238 A | 12/1998 | Jackson et al. |
| 5,846,239 A | 12/1998 | Swanson et al. |
| 5,848,969 A | 12/1998 | Panescu et al. |
| 5,853,411 A | 12/1998 | Whayne et al. |
| 5,855,614 A | 1/1999 | Stevens et al. |
| 5,860,970 A | 1/1999 | Goddard et al. |
| 5,860,974 A | 1/1999 | Abele |
| 5,865,787 A | 2/1999 | Shapland et al. |
| 5,865,801 A | 2/1999 | Houser |
| 5,868,735 A | 2/1999 | Lafontaine |
| 5,868,736 A | 2/1999 | Swanson et al. |
| 5,871,483 A | 2/1999 | Jackson et al. |
| 5,875,782 A | 3/1999 | Ferrari et al. |
| 5,876,369 A | 3/1999 | Houser |
| 5,876,374 A | 3/1999 | Alba et al. |
| 5,879,348 A | 3/1999 | Owens et al. |
| 5,891,135 A | 4/1999 | Jackson et al. |
| 5,891,136 A | 4/1999 | McGee et al. |
| 5,893,885 A | 4/1999 | Webster et al. |
| 5,902,299 A | 5/1999 | Jayaraman |
| 5,902,328 A | 5/1999 | LaFontaine et al. |
| 5,904,697 A | 5/1999 | Gifford, III et al. |
| 5,916,227 A | 6/1999 | Keith et al. |
| 5,924,424 A | 7/1999 | Stevens et al. |
| 5,925,038 A | 7/1999 | Panescu et al. |
| 5,934,284 A | 8/1999 | Plaia et al. |
| 5,938,670 A | 8/1999 | Keith et al. |
| 5,944,710 A | 8/1999 | Dev et al. |
| 5,947,977 A | 9/1999 | Slepian et al. |
| 5,951,539 A | 9/1999 | Nita et al. |
| 5,954,719 A | 9/1999 | Chen et al. |
| 5,961,513 A | 10/1999 | Swanson et al. |

(56) References Cited

U.S. PATENT DOCUMENTS

| | | |
|---|---|---|
| 5,967,984 A | 10/1999 | Chu et al. |
| 5,971,979 A | 10/1999 | Joye et al. |
| 5,983,141 A | 11/1999 | Sluijter et al. |
| 5,989,208 A | 11/1999 | Nita |
| 5,989,284 A | 11/1999 | Laufer |
| 5,997,497 A | 12/1999 | Nita et al. |
| 6,004,269 A | 12/1999 | Crowley et al. |
| 6,004,316 A | 12/1999 | Laufer |
| 6,009,877 A | 1/2000 | Edwards |
| 6,012,457 A | 1/2000 | Lesh |
| 6,024,740 A | 2/2000 | Lesh et al. |
| 6,024,752 A | 2/2000 | Horn et al. |
| 6,032,675 A | 3/2000 | Rubinsky |
| 6,033,397 A | 3/2000 | Laufer et al. |
| 6,033,398 A | 3/2000 | Farley et al. |
| 6,036,687 A | 3/2000 | Laufer et al. |
| 6,036,689 A | 3/2000 | Tu et al. |
| 6,056,744 A | 5/2000 | Edwards |
| 6,063,085 A | 5/2000 | Tay et al. |
| 6,066,134 A | 5/2000 | Eggers et al. |
| 6,068,638 A | 5/2000 | Makower |
| 6,068,653 A | 5/2000 | LaFontaine |
| 6,071,277 A | 6/2000 | Farley et al. |
| 6,071,278 A | 6/2000 | Panescu et al. |
| 6,079,414 A | 6/2000 | Roth |
| 6,080,171 A | 6/2000 | Keith et al. |
| 6,081,749 A | 6/2000 | Ingle et al. |
| 6,086,581 A | 7/2000 | Reynolds et al. |
| 6,091,995 A | 7/2000 | Ingle et al. |
| 6,093,166 A | 7/2000 | Knudson et al. |
| 6,096,021 A | 8/2000 | Helm et al. |
| 6,099,524 A | 8/2000 | Lipson et al. |
| 6,099,526 A | 8/2000 | Whayne et al. |
| 6,102,908 A | 8/2000 | Tu et al. |
| 6,110,187 A | 8/2000 | Donlon |
| 6,110,192 A | 8/2000 | Ravenscroft et al. |
| 6,117,101 A | 9/2000 | Diederich et al. |
| 6,120,516 A | 9/2000 | Selmon et al. |
| 6,123,682 A | 9/2000 | Knudson et al. |
| 6,123,718 A | 9/2000 | Tu et al. |
| 6,135,997 A | 10/2000 | Laufer et al. |
| 6,135,999 A | 10/2000 | Fanton et al. |
| 6,142,991 A | 11/2000 | Schatzberger |
| 6,142,993 A | 11/2000 | Whayne et al. |
| 6,149,620 A | 11/2000 | Baker et al. |
| 6,152,899 A | 11/2000 | Farley et al. |
| 6,159,225 A | 12/2000 | Makower |
| 6,161,048 A | 12/2000 | Sluijter et al. |
| 6,161,049 A | 12/2000 | Rudie et al. |
| 6,161,543 A | 12/2000 | Cox et al. |
| 6,164,283 A | 12/2000 | Lesh |
| 6,165,172 A | 12/2000 | Farley et al. |
| 6,165,187 A | 12/2000 | Reger |
| 6,168,594 B1 | 1/2001 | LaFontaine et al. |
| 6,171,321 B1 | 1/2001 | Gifford, III et al. |
| 6,179,832 B1 | 1/2001 | Jones et al. |
| 6,179,835 B1 | 1/2001 | Panescu et al. |
| 6,179,859 B1 | 1/2001 | Bates et al. |
| 6,183,486 B1 | 2/2001 | Snow et al. |
| 6,190,356 B1 | 2/2001 | Bersin |
| 6,190,379 B1 | 2/2001 | Heuser et al. |
| 6,216,704 B1 | 4/2001 | Ingle et al. |
| 6,219,577 B1 | 4/2001 | Brown, III et al. |
| 6,224,592 B1 | 5/2001 | Eggers et al. |
| 6,231,587 B1 | 5/2001 | Makower |
| 6,237,355 B1 | 5/2001 | Li |
| 6,237,605 B1 | 5/2001 | Vaska et al. |
| 6,238,389 B1 | 5/2001 | Paddock et al. |
| 6,238,392 B1 | 5/2001 | Long |
| 6,241,722 B1 | 6/2001 | Dobak et al. |
| 6,246,912 B1 | 6/2001 | Sluijter et al. |
| 6,254,598 B1 | 7/2001 | Edwards et al. |
| 6,273,886 B1 | 8/2001 | Edwards et al. |
| 6,280,466 B1 | 8/2001 | Kugler et al. |
| 6,283,951 B1 | 9/2001 | Flaherty et al. |
| 6,283,959 B1 | 9/2001 | Lalonde et al. |
| 6,290,696 B1 | 9/2001 | Lafontaine |
| 6,292,695 B1 | 9/2001 | Webster, Jr. et al. |
| 6,296,619 B1 | 10/2001 | Brisken et al. |
| 6,309,379 B1 | 10/2001 | Willard et al. |
| 6,314,325 B1 | 11/2001 | Fitz |
| 6,315,776 B1 | 11/2001 | Edwards et al. |
| 6,317,615 B1 | 11/2001 | Kenknight et al. |
| 6,319,242 B1 | 11/2001 | Patterson et al. |
| 6,319,251 B1 | 11/2001 | Tu et al. |
| 6,322,558 B1 | 11/2001 | Taylor et al. |
| 6,322,559 B1 | 11/2001 | Daulton et al. |
| 6,346,074 B1 | 2/2002 | Roth |
| 6,350,248 B1 | 2/2002 | Knudson et al. |
| 6,355,029 B1 | 3/2002 | Joye et al. |
| 6,357,447 B1 | 3/2002 | Swanson et al. |
| 6,361,519 B1 | 3/2002 | Knudson et al. |
| 6,364,840 B1 | 4/2002 | Crowley |
| 6,371,965 B2 | 4/2002 | Gifford, III et al. |
| 6,375,668 B1 | 4/2002 | Gifford et al. |
| 6,379,352 B1 | 4/2002 | Reynolds et al. |
| 6,379,373 B1 | 4/2002 | Sawhney et al. |
| 6,383,151 B1 | 5/2002 | Diederich et al. |
| 6,387,105 B1 | 5/2002 | Gifford, III et al. |
| 6,389,314 B2 | 5/2002 | Feiring |
| 6,394,096 B1 | 5/2002 | Constantz |
| 6,398,780 B1 | 6/2002 | Farley et al. |
| 6,398,792 B1 | 6/2002 | O'Connor |
| 6,401,720 B1 | 6/2002 | Stevens et al. |
| 6,405,732 B1 | 6/2002 | Edwards et al. |
| 6,409,723 B1 | 6/2002 | Edwards |
| 6,413,255 B1 | 7/2002 | Stern |
| 6,425,867 B1 | 7/2002 | Vaezy et al. |
| 6,427,089 B1 | 7/2002 | Knowlton |
| 6,428,534 B1 | 8/2002 | Joye et al. |
| 6,428,536 B2 | 8/2002 | Panescu et al. |
| 6,432,102 B2 | 8/2002 | Joye et al. |
| 6,436,056 B1 | 8/2002 | Wang et al. |
| 6,442,413 B1 | 8/2002 | Silver |
| 6,443,965 B1 | 9/2002 | Gifford, III et al. |
| 6,447,505 B2 | 9/2002 | McGovern et al. |
| 6,451,034 B1 | 9/2002 | Gifford, III et al. |
| 6,451,045 B1 | 9/2002 | Walker et al. |
| 6,458,098 B1 | 10/2002 | Kanesaka |
| 6,468,297 B1 | 10/2002 | Williams et al. |
| 6,470,219 B1 | 10/2002 | Edwards et al. |
| 6,475,213 B1 | 11/2002 | Whayne et al. |
| 6,477,426 B1 | 11/2002 | Fenn et al. |
| 6,485,489 B2 | 11/2002 | Teirstein et al. |
| 6,488,679 B1 | 12/2002 | Swanson et al. |
| 6,491,705 B2 | 12/2002 | Gifford, III et al. |
| 6,496,737 B2 | 12/2002 | Rudie et al. |
| 6,497,703 B1 | 12/2002 | Korteling et al. |
| 6,497,711 B1 | 12/2002 | Plaia et al. |
| 6,500,174 B1 | 12/2002 | Maguire et al. |
| 6,506,189 B1 | 1/2003 | Rittman, III et al. |
| 6,511,478 B1 | 1/2003 | Burnside et al. |
| 6,511,496 B1 | 1/2003 | Huter et al. |
| 6,514,226 B1 | 2/2003 | Levin et al. |
| 6,514,245 B1 | 2/2003 | Williams et al. |
| 6,517,533 B1 | 2/2003 | Swaminathan |
| 6,517,534 B1 | 2/2003 | McGovern et al. |
| 6,517,572 B2 | 2/2003 | Kugler et al. |
| 6,522,913 B2 | 2/2003 | Swanson et al. |
| 6,522,926 B1 | 2/2003 | Kieval et al. |
| 6,524,274 B1 | 2/2003 | Rosenthal et al. |
| 6,527,739 B1 | 3/2003 | Bigus et al. |
| 6,527,765 B2 | 3/2003 | Kelman et al. |
| 6,527,769 B2 | 3/2003 | Langberg et al. |
| 6,537,271 B1 | 3/2003 | Murray et al. |
| 6,540,734 B1 | 4/2003 | Chiu et al. |
| 6,540,761 B2 | 4/2003 | Houser |
| 6,542,781 B1 | 4/2003 | Koblish et al. |
| 6,551,309 B1 | 4/2003 | LePivert |
| 6,558,381 B2 | 5/2003 | Ingle et al. |
| 6,562,034 B2 | 5/2003 | Edwards et al. |
| 6,565,582 B2 | 5/2003 | Gifford, III et al. |

(56) References Cited

U.S. PATENT DOCUMENTS

| | | | |
|---|---|---|---|
| 6,575,933 B1 | 6/2003 | Wittenberger et al. |
| 6,579,311 B1 | 6/2003 | Makower |
| 6,582,423 B1 | 6/2003 | Thapliyal et al. |
| 6,589,238 B2 | 7/2003 | Edwards et al. |
| 6,592,526 B1 | 7/2003 | Lenker |
| 6,602,246 B1 | 8/2003 | Joye et al. |
| 6,602,247 B2 | 8/2003 | Lalonde |
| 6,607,502 B1 | 8/2003 | Maguire et al. |
| 6,610,083 B2 | 8/2003 | Keller et al. |
| 6,616,624 B1 | 9/2003 | Kieval |
| 6,622,731 B2 | 9/2003 | Daniel et al. |
| 6,623,452 B2 | 9/2003 | Chien et al. |
| 6,623,453 B1 | 9/2003 | Guibert et al. |
| 6,632,196 B1 | 10/2003 | Houser |
| 6,635,054 B2 | 10/2003 | Fjield et al. |
| 6,640,120 B1 | 10/2003 | Swanson et al. |
| 6,648,854 B1 | 11/2003 | Patterson et al. |
| 6,648,878 B2 | 11/2003 | Lafontaine |
| 6,648,879 B2 | 11/2003 | Joye et al. |
| 6,651,672 B2 | 11/2003 | Roth |
| 6,652,515 B1 | 11/2003 | Maguire et al. |
| 6,658,279 B2 | 12/2003 | Swanson et al. |
| 6,666,858 B2 | 12/2003 | Lafontaine |
| 6,673,040 B1 | 1/2004 | Samson et al. |
| 6,673,066 B2 | 1/2004 | Werneth |
| 6,673,290 B1 | 1/2004 | Whayne et al. |
| 6,676,678 B2 | 1/2004 | Gifford, III et al. |
| 6,679,268 B2 | 1/2004 | Stevens et al. |
| 6,681,773 B2 | 1/2004 | Murphy et al. |
| 6,682,541 B1 | 1/2004 | Gifford, III et al. |
| 6,685,648 B2 | 2/2004 | Flaherty et al. |
| 6,685,732 B2 | 2/2004 | Kramer |
| 6,685,733 B1 | 2/2004 | Dae et al. |
| 6,689,086 B1 | 2/2004 | Nita et al. |
| 6,689,148 B2 | 2/2004 | Sawhney et al. |
| 6,692,490 B1 | 2/2004 | Edwards |
| 6,695,830 B2 | 2/2004 | Vigil et al. |
| 6,695,857 B2 | 2/2004 | Gifford, III et al. |
| 6,699,241 B2 | 3/2004 | Rappaport et al. |
| 6,699,257 B2 | 3/2004 | Gifford, III et al. |
| 6,706,010 B1 | 3/2004 | Miki et al. |
| 6,706,037 B2 | 3/2004 | Zvuloni et al. |
| 6,709,431 B2 | 3/2004 | Lafontaine |
| 6,711,444 B2 | 3/2004 | Koblish |
| 6,712,815 B2 | 3/2004 | Sampson et al. |
| 6,736,811 B2 | 5/2004 | Panescu et al. |
| 6,736,835 B2 | 5/2004 | Pellegrino et al. |
| 6,746,464 B1 | 6/2004 | Makower |
| 6,746,465 B2 | 6/2004 | Diederich et al. |
| 6,748,255 B2 | 6/2004 | Fuimaono et al. |
| 6,748,953 B2 | 6/2004 | Sherry et al. |
| 6,752,805 B2 | 6/2004 | Maguire et al. |
| 6,755,823 B2 | 6/2004 | Lalonde |
| 6,763,261 B2 | 7/2004 | Casscells, III et al. |
| 6,764,501 B2 | 7/2004 | Ganz |
| 6,771,996 B2 | 8/2004 | Bowe et al. |
| 6,780,183 B2 | 8/2004 | Jimenez, Jr. et al. |
| 6,786,900 B2 | 9/2004 | Joye et al. |
| 6,786,901 B2 | 9/2004 | Joye et al. |
| 6,788,977 B2 | 9/2004 | Fenn et al. |
| 6,790,222 B2 | 9/2004 | Kugler et al. |
| 6,800,075 B2 | 10/2004 | Mische et al. |
| 6,807,444 B2 | 10/2004 | Tu et al. |
| 6,811,550 B2 | 11/2004 | Holland et al. |
| 6,813,520 B2 | 11/2004 | Truckai et al. |
| 6,814,733 B2 | 11/2004 | Schwartz et al. |
| 6,824,516 B2 | 11/2004 | Batten et al. |
| 6,824,543 B2 | 11/2004 | Lentz |
| 6,827,726 B2 | 12/2004 | Parodi |
| 6,845,267 B2 | 1/2005 | Harrison et al. |
| 6,847,848 B2 | 1/2005 | Sterzer et al. |
| 6,850,801 B2 | 2/2005 | Kieval et al. |
| 6,855,143 B2 | 2/2005 | Davison et al. |
| 6,869,431 B2 | 3/2005 | Maguire et al. |
| 6,875,209 B2 | 4/2005 | Zvuloni et al. |
| 6,884,260 B2 | 4/2005 | Kugler et al. |
| 6,885,888 B2 | 4/2005 | Rezai |
| 6,893,436 B2 | 5/2005 | Woodard et al. |
| 6,895,265 B2 | 5/2005 | Silver |
| 6,898,454 B2 | 5/2005 | Atalar et al. |
| 6,899,718 B2 | 5/2005 | Gifford, III et al. |
| 6,905,494 B2 | 6/2005 | Yon et al. |
| 6,905,510 B2 | 6/2005 | Saab |
| 6,908,462 B2 | 6/2005 | Joye et al. |
| 6,909,009 B2 | 6/2005 | Koridze |
| 6,917,834 B2 | 7/2005 | Koblish et al. |
| 6,923,805 B1 | 8/2005 | LaFontaine et al. |
| 6,923,808 B2 | 8/2005 | Taimisto |
| 6,926,716 B2 | 8/2005 | Baker et al. |
| 6,929,639 B2 | 8/2005 | Lafontaine |
| 6,939,346 B2 | 9/2005 | Kannenberg et al. |
| 6,942,657 B2 | 9/2005 | Sinofsky et al. |
| 6,942,692 B2 | 9/2005 | Landau et al. |
| 6,949,097 B2 | 9/2005 | Stewart et al. |
| 6,949,121 B1 | 9/2005 | Laguna |
| 6,952,615 B2 | 10/2005 | Satake |
| 6,955,174 B2 | 10/2005 | Joye et al. |
| 6,955,175 B2 | 10/2005 | Stevens et al. |
| 6,958,075 B2 | 10/2005 | Mon et al. |
| 6,959,711 B2 | 11/2005 | Murphy et al. |
| 6,964,660 B2 | 11/2005 | Maguire et al. |
| 6,966,908 B2 | 11/2005 | Maguire et al. |
| 6,972,015 B2 | 12/2005 | Joye et al. |
| 6,972,024 B1 | 12/2005 | Kilpatrick et al. |
| 6,974,456 B2 | 12/2005 | Edwards et al. |
| 6,979,420 B2 | 12/2005 | Weber |
| 6,981,382 B2 | 1/2006 | Lentz et al. |
| 6,984,238 B2 | 1/2006 | Gifford, III et al. |
| 6,989,009 B2 | 1/2006 | Lafontaine |
| 6,991,617 B2 | 1/2006 | Hektner et al. |
| 7,001,378 B2 | 2/2006 | Yon et al. |
| 7,006,858 B2 | 2/2006 | Silver et al. |
| 7,022,105 B1 | 4/2006 | Edwards |
| 7,022,120 B2 | 4/2006 | Lafontaine |
| 7,033,322 B2 | 4/2006 | Silver |
| 7,041,098 B2 | 5/2006 | Farley et al. |
| 7,060,062 B2 | 6/2006 | Joye et al. |
| 7,066,895 B2 | 6/2006 | Podany |
| 7,066,904 B2 | 6/2006 | Rosenthal et al. |
| 7,081,112 B2 | 7/2006 | Joye et al. |
| 7,081,115 B2 | 7/2006 | Taimisto |
| 7,087,026 B2 | 8/2006 | Callister et al. |
| 7,087,052 B2 | 8/2006 | Sampson et al. |
| 7,100,614 B2 | 9/2006 | Stevens et al. |
| 7,101,368 B2 | 9/2006 | Lafontaine |
| 7,108,715 B2 | 9/2006 | Lawrence-Brown et al. |
| 7,112,198 B2 | 9/2006 | Satake |
| 7,112,211 B2 | 9/2006 | Gifford, III et al. |
| 7,122,033 B2 | 10/2006 | Wood |
| 7,149,574 B2 | 12/2006 | Yun et al. |
| 7,150,745 B2 | 12/2006 | Stern et al. |
| 7,153,315 B2 | 12/2006 | Miller |
| 7,156,840 B2 | 1/2007 | Lentz et al. |
| 7,158,832 B2 | 1/2007 | Kieval et al. |
| 7,162,303 B2 | 1/2007 | Levin et al. |
| 7,165,551 B2 | 1/2007 | Edwards et al. |
| 7,172,589 B2 | 2/2007 | Lafontaine |
| 7,172,610 B2 | 2/2007 | Heitzmann et al. |
| 7,181,261 B2 | 2/2007 | Silver et al. |
| 7,184,827 B1 | 2/2007 | Edwards |
| 7,189,227 B2 | 3/2007 | Lafontaine |
| 7,197,354 B2 | 3/2007 | Sobe |
| 7,198,632 B2 | 4/2007 | Lim et al. |
| 7,200,445 B1 | 4/2007 | Dalbec et al. |
| 7,214,234 B2 | 5/2007 | Rapacki et al. |
| 7,220,233 B2 | 5/2007 | Nita et al. |
| 7,220,270 B2 | 5/2007 | Sawhney et al. |
| 7,221,979 B2 | 5/2007 | Zhou et al. |
| 7,241,273 B2 | 7/2007 | Maguire et al. |
| 7,241,736 B2 | 7/2007 | Hunter et al. |
| 7,250,041 B2 | 7/2007 | Chiu et al. |
| 7,252,679 B2 | 8/2007 | Fischell et al. |
| 7,264,619 B2 | 9/2007 | Venturelli |
| 7,285,120 B2 | 10/2007 | Im et al. |

(56) References Cited

U.S. PATENT DOCUMENTS

| | | |
|---|---|---|
| 7,288,089 B2 | 10/2007 | Yon et al. |
| 7,288,096 B2 | 10/2007 | Chin |
| 7,291,146 B2 | 11/2007 | Steinke et al. |
| 7,293,562 B2 | 11/2007 | Malecki et al. |
| 7,294,126 B2 | 11/2007 | Sampson et al. |
| 7,297,475 B2 | 11/2007 | Koiwai et al. |
| 7,300,433 B2 | 11/2007 | Lane et al. |
| 7,306,590 B2 | 12/2007 | Swanson |
| 7,314,483 B2 | 1/2008 | Landau et al. |
| 7,323,006 B2 | 1/2008 | Andreas et al. |
| 7,326,235 B2 | 2/2008 | Edwards |
| 7,326,237 B2 | 2/2008 | DePalma et al. |
| 7,329,236 B2 | 2/2008 | Kesten et al. |
| 7,335,192 B2 | 2/2008 | Keren et al. |
| 7,338,467 B2 | 3/2008 | Lutter |
| 7,341,570 B2 | 3/2008 | Keren et al. |
| 7,357,797 B2 | 4/2008 | Ryba |
| 7,364,566 B2 | 4/2008 | Elkins et al. |
| 7,367,970 B2 | 5/2008 | Govari et al. |
| 7,367,975 B2 | 5/2008 | Malecki et al. |
| 7,371,231 B2 | 5/2008 | Rioux et al. |
| 7,381,200 B2 | 6/2008 | Katoh et al. |
| 7,387,126 B2 | 6/2008 | Cox et al. |
| 7,390,894 B2 | 6/2008 | Weinshilboum et al. |
| 7,404,824 B1 | 7/2008 | Webler et al. |
| 7,407,506 B2 | 8/2008 | Makower |
| 7,407,671 B2 | 8/2008 | McBride et al. |
| 7,410,486 B2 | 8/2008 | Fuimaono et al. |
| 7,413,556 B2 | 8/2008 | Zhang et al. |
| 7,425,212 B1 | 9/2008 | Danek et al. |
| 7,426,409 B2 | 9/2008 | Casscells, III et al. |
| 7,449,018 B2 | 11/2008 | Kramer |
| 7,481,803 B2 | 1/2009 | Kesten et al. |
| 7,481,808 B2 | 1/2009 | Koyfman et al. |
| 7,485,104 B2 | 2/2009 | Kieval |
| 7,487,780 B2 | 2/2009 | Hooven |
| 7,494,485 B2 | 2/2009 | Beck et al. |
| 7,494,486 B2 | 2/2009 | Mische et al. |
| 7,505,812 B1 | 3/2009 | Eggers et al. |
| 7,507,233 B2 | 3/2009 | Littrup et al. |
| 7,512,445 B2 | 3/2009 | Truckai et al. |
| 7,529,589 B2 | 5/2009 | Williams et al. |
| RE40,863 E | 7/2009 | Tay et al. |
| 7,556,624 B2 | 7/2009 | Laufer et al. |
| 7,563,247 B2 | 7/2009 | Maguire et al. |
| 7,566,319 B2 | 7/2009 | McAuley et al. |
| 7,582,111 B2 | 9/2009 | Krolik et al. |
| 7,591,996 B2 | 9/2009 | Hwang et al. |
| 7,597,704 B2 | 10/2009 | Frazier et al. |
| 7,603,166 B2 | 10/2009 | Casscells, III et al. |
| 7,604,631 B2 | 10/2009 | Reynolds |
| 7,604,633 B2 | 10/2009 | Truckai et al. |
| 7,615,072 B2 | 11/2009 | Rust et al. |
| 7,617,005 B2 | 11/2009 | Demarais et al. |
| 7,632,268 B2 | 12/2009 | Edwards et al. |
| 7,635,383 B2 | 12/2009 | Gumm |
| 7,641,633 B2 | 1/2010 | Laufer et al. |
| 7,641,679 B2 | 1/2010 | Joye et al. |
| 7,647,115 B2 | 1/2010 | Levin et al. |
| 7,653,438 B2 | 1/2010 | Deem et al. |
| 7,670,279 B2 | 3/2010 | Gertner |
| 7,678,108 B2 | 3/2010 | Christian et al. |
| 7,706,882 B2 | 4/2010 | Francischelli et al. |
| 7,717,948 B2 | 5/2010 | Demarais et al. |
| 7,722,539 B2 | 5/2010 | Carter et al. |
| 7,736,360 B2 | 6/2010 | Mody et al. |
| 7,736,362 B2 | 6/2010 | Eberl et al. |
| 7,744,594 B2 | 6/2010 | Yamazaki et al. |
| 7,753,907 B2 | 7/2010 | DiMatteo et al. |
| 7,758,571 B2 | 7/2010 | Saadat |
| 7,766,892 B2 | 8/2010 | Keren et al. |
| 7,778,703 B2 | 8/2010 | Gross et al. |
| 7,785,289 B2 | 8/2010 | Rios et al. |
| 7,792,568 B2 | 9/2010 | Zhong et al. |
| 7,803,168 B2 | 9/2010 | Gifford et al. |
| 7,811,313 B2 | 10/2010 | Mon et al. |
| 7,818,053 B2 | 10/2010 | Kassab |
| 7,822,460 B2 | 10/2010 | Halperin et al. |
| 7,832,407 B2 | 11/2010 | Gertner |
| 7,833,220 B2 | 11/2010 | Mon et al. |
| 7,837,720 B2 | 11/2010 | Mon |
| 7,841,978 B2 | 11/2010 | Gertner |
| 7,846,172 B2 | 12/2010 | Makower |
| 7,849,860 B2 | 12/2010 | Makower et al. |
| 7,861,725 B2 | 1/2011 | Swanson |
| 7,901,402 B2 | 3/2011 | Jones et al. |
| 7,927,370 B2 | 4/2011 | Webler et al. |
| 7,942,928 B2 | 5/2011 | Webler et al. |
| 7,946,976 B2 | 5/2011 | Gertner |
| 1,015,285 A1 | 6/2011 | Mayse et al. |
| 7,959,627 B2 | 6/2011 | Utley et al. |
| 7,967,782 B2 | 6/2011 | Laufer et al. |
| 7,972,327 B2 | 7/2011 | Eberl et al. |
| 7,972,330 B2 | 7/2011 | Alejandro et al. |
| 8,001,976 B2 | 8/2011 | Gertner |
| 8,012,147 B2 | 9/2011 | Lafontaine |
| 8,019,435 B2 | 9/2011 | Hastings et al. |
| 8,021,362 B2 | 9/2011 | Deem et al. |
| 8,021,413 B2 | 9/2011 | Dierking et al. |
| 8,025,661 B2 | 9/2011 | Arnold et al. |
| 1,026,392 A1 | 10/2011 | Vrba et al. |
| 1,026,408 A1 | 10/2011 | Ingle |
| 1,027,023 A1 | 11/2011 | Rizq et al. |
| 1,028,227 A1 | 11/2011 | Lafontaine |
| 8,062,289 B2 | 11/2011 | Babaev |
| 8,075,580 B2 | 12/2011 | Makower |
| 8,080,006 B2 | 12/2011 | Lafontaine et al. |
| 8,088,125 B2 | 1/2012 | Lafontaine |
| 8,088,127 B2 | 1/2012 | Mayse et al. |
| 8,123,741 B2 | 2/2012 | Marrouche et al. |
| 8,128,617 B2 | 3/2012 | Bencini et al. |
| 8,131,371 B2 | 3/2012 | Demarais et al. |
| 8,131,372 B2 | 3/2012 | Levin et al. |
| 8,140,170 B2 | 3/2012 | Rezai et al. |
| 8,145,317 B2 | 3/2012 | Demarais et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,152,830 B2 | 4/2012 | Gumm |
| 8,175,711 B2 | 5/2012 | Demarais et al. |
| 8,187,261 B2 | 5/2012 | Watson |
| 8,221,407 B2 | 7/2012 | Phan et al. |
| 8,226,637 B2 | 7/2012 | Satake |
| 8,231,617 B2 | 7/2012 | Satake |
| 8,251,992 B2 | 8/2012 | Utley et al. |
| 8,257,413 B2 | 9/2012 | Danek et al. |
| 8,257,724 B2 | 9/2012 | Cromack et al. |
| 8,257,725 B2 | 9/2012 | Cromack et al. |
| 8,277,379 B2 | 10/2012 | Lau et al. |
| 8,287,532 B2 | 10/2012 | Carroll et al. |
| 8,295,902 B2 | 10/2012 | Salahieh et al. |
| 8,317,776 B2 | 11/2012 | Ferren et al. |
| 8,343,031 B2 | 1/2013 | Gertner |
| 8,347,891 B2 | 1/2013 | Demarais et al. |
| 8,353,945 B2 | 1/2013 | Andreas et al. |
| 8,382,697 B2 | 2/2013 | Brenneman et al. |
| 8,388,680 B2 | 3/2013 | Starksen et al. |
| 8,396,548 B2 | 3/2013 | Perry et al. |
| 8,401,650 B2 | 3/2013 | Simon et al. |
| 8,401,667 B2 | 3/2013 | Gustus et al. |
| 8,403,881 B2 | 3/2013 | Ferren et al. |
| 8,409,172 B2 | 4/2013 | Moll et al. |
| 8,439,909 B2 | 5/2013 | Wang et al. |
| 8,460,358 B2 | 6/2013 | Andreas et al. |
| 8,465,452 B2 | 6/2013 | Kassab |
| 8,469,919 B2 | 6/2013 | Ingle et al. |
| 8,473,067 B2 | 6/2013 | Hastings et al. |
| 8,475,441 B2 | 7/2013 | Babkin et al. |
| 8,480,663 B2 | 7/2013 | Ingle et al. |
| 8,480,664 B2 | 7/2013 | Watson et al. |
| 8,663,211 B2 | 3/2014 | Fourkas |
| 8,666,496 B2 | 3/2014 | Simon et al. |
| 8,740,895 B2 | 6/2014 | Mayse et al. |
| 8,758,334 B2 | 6/2014 | Coe et al. |

(56) References Cited

U.S. PATENT DOCUMENTS

| | | |
|---|---|---|
| 8,777,943 B2 | 7/2014 | Mayse et al. |
| 8,909,316 B2 | 12/2014 | Ng |
| 8,920,414 B2 | 12/2014 | Stone et al. |
| 8,951,251 B2 | 2/2015 | Willard |
| 9,005,191 B2 | 4/2015 | Azamian et al. |
| 9,072,902 B2 | 7/2015 | Mathur et al. |
| 9,084,609 B2 | 7/2015 | Smith |
| 9,101,343 B2 | 8/2015 | Duong et al. |
| 9,174,050 B2 | 11/2015 | Mathur et al. |
| 9,179,973 B2 | 11/2015 | Nabutovsky et al. |
| 9,186,211 B2 | 11/2015 | Mathur |
| 9,237,984 B2 | 1/2016 | Hawkins et al. |
| 9,265,575 B2 | 2/2016 | Coe et al. |
| 9,314,300 B2 | 4/2016 | Nabutovsky et al. |
| 9,402,676 B2 | 8/2016 | Babkin et al. |
| 9,402,684 B2 | 8/2016 | Mathur et al. |
| 9,414,885 B2 | 8/2016 | Willard |
| 9,427,283 B2 | 8/2016 | Nabutovsky et al. |
| 9,463,062 B2 | 10/2016 | Smith et al. |
| 9,463,065 B2 | 10/2016 | Sugimoto et al. |
| 9,566,114 B2 | 2/2017 | Mathur |
| 2001/0007070 A1 | 7/2001 | Stewart et al. |
| 2001/0044596 A1 | 11/2001 | Jaafar |
| 2002/0045811 A1 | 4/2002 | Kittrell et al. |
| 2002/0045893 A1 | 4/2002 | Lane et al. |
| 2002/0077592 A1 | 6/2002 | Barry |
| 2002/0082552 A1 | 6/2002 | Ding et al. |
| 2002/0087208 A1 | 7/2002 | Koblish et al. |
| 2002/0095197 A1 | 7/2002 | Lardo et al. |
| 2002/0103445 A1 | 8/2002 | Rahdert et al. |
| 2002/0107536 A1 | 8/2002 | Hussein |
| 2002/0120258 A1 | 8/2002 | Lalonde |
| 2002/0139379 A1 | 10/2002 | Edwards et al. |
| 2002/0143324 A1 | 10/2002 | Edwards |
| 2002/0147480 A1 | 10/2002 | Mamayek |
| 2002/0165532 A1 | 11/2002 | Hill et al. |
| 2002/0165535 A1 | 11/2002 | Lesh et al. |
| 2002/0183682 A1 | 12/2002 | Darvish et al. |
| 2003/0018327 A1 | 1/2003 | Truckai et al. |
| 2003/0028114 A1 | 2/2003 | Casscells et al. |
| 2003/0036752 A1 | 2/2003 | Joye et al. |
| 2003/0050635 A1 | 3/2003 | Truckai et al. |
| 2003/0050637 A1 | 3/2003 | Maguire et al. |
| 2003/0050681 A1 | 3/2003 | Pianca et al. |
| 2003/0060762 A1 | 3/2003 | Zvuloni et al. |
| 2003/0060857 A1 | 3/2003 | Perrson et al. |
| 2003/0060858 A1 | 3/2003 | Kieval et al. |
| 2003/0069619 A1 | 4/2003 | Fenn et al. |
| 2003/0074039 A1 | 4/2003 | Puskas |
| 2003/0088189 A1 | 5/2003 | Tu et al. |
| 2003/0088240 A1 | 5/2003 | Saadat |
| 2003/0114791 A1 | 6/2003 | Rosenthal et al. |
| 2003/0120271 A1 | 6/2003 | Burnside et al. |
| 2003/0125790 A1 | 7/2003 | Fastovsky et al. |
| 2003/0144658 A1 | 7/2003 | Schwartz et al. |
| 2003/0158584 A1 | 8/2003 | Cates et al. |
| 2003/0181897 A1 | 9/2003 | Thomas et al. |
| 2003/0199747 A1 | 10/2003 | Michlitsch et al. |
| 2003/0199863 A1 | 10/2003 | Swanson et al. |
| 2003/0216792 A1 | 11/2003 | Levin et al. |
| 2003/0229340 A1 | 12/2003 | Sherry et al. |
| 2003/0229384 A1 | 12/2003 | Mon |
| 2003/0233099 A1 | 12/2003 | Danaek et al. |
| 2004/0006359 A1 | 1/2004 | Laguna |
| 2004/0010289 A1 | 1/2004 | Biggs et al. |
| 2004/0019348 A1 | 1/2004 | Stevens et al. |
| 2004/0024371 A1 | 2/2004 | Plicchi et al. |
| 2004/0024392 A1 | 2/2004 | Lewis et al. |
| 2004/0064090 A1 | 4/2004 | Keren et al. |
| 2004/0064093 A1 | 4/2004 | Hektner et al. |
| 2004/0073206 A1 | 4/2004 | Foley et al. |
| 2004/0082978 A1 | 4/2004 | Harrison et al. |
| 2004/0088002 A1 | 5/2004 | Boyle et al. |
| 2004/0111016 A1 | 6/2004 | Casscells et al. |
| 2004/0117032 A1 | 6/2004 | Roth |
| 2004/0122421 A1 | 6/2004 | Wood |
| 2004/0147915 A1 | 7/2004 | Hasebe |
| 2004/0162555 A1 | 8/2004 | Farley et al. |
| 2004/0167506 A1 | 8/2004 | Chen |
| 2004/0186468 A1 | 9/2004 | Edwards |
| 2004/0215186 A1 | 10/2004 | Cornelius et al. |
| 2004/0220556 A1 | 11/2004 | Cooper et al. |
| 2004/0243022 A1 | 12/2004 | Carney et al. |
| 2004/0243119 A1 | 12/2004 | Lane et al. |
| 2004/0243199 A1 | 12/2004 | Mon et al. |
| 2004/0253304 A1 | 12/2004 | Gross et al. |
| 2004/0267250 A1 | 12/2004 | Yon et al. |
| 2005/0080374 A1 | 4/2005 | Esch et al. |
| 2005/0080409 A1 | 4/2005 | Young et al. |
| 2005/0096647 A1 | 5/2005 | Steinke et al. |
| 2005/0143817 A1 | 6/2005 | Hunter et al. |
| 2005/0149069 A1 | 7/2005 | Bertolero et al. |
| 2005/0149080 A1 | 7/2005 | Hunter et al. |
| 2005/0149158 A1 | 7/2005 | Hunter et al. |
| 2005/0149173 A1 | 7/2005 | Hunter et al. |
| 2005/0149175 A1 | 7/2005 | Hunter et al. |
| 2005/0154445 A1 | 7/2005 | Hunter et al. |
| 2005/0154453 A1 | 7/2005 | Hunter et al. |
| 2005/0154454 A1 | 7/2005 | Hunter et al. |
| 2005/0165389 A1 | 7/2005 | Swain et al. |
| 2005/0165391 A1 | 7/2005 | Maguire et al. |
| 2005/0165467 A1 | 7/2005 | Hunter et al. |
| 2005/0165488 A1 | 7/2005 | Hunter et al. |
| 2005/0175661 A1 | 8/2005 | Hunter et al. |
| 2005/0175662 A1 | 8/2005 | Hunter et al. |
| 2005/0175663 A1 | 8/2005 | Hunter et al. |
| 2005/0177103 A1 | 8/2005 | Hunter et al. |
| 2005/0177225 A1 | 8/2005 | Hunter et al. |
| 2005/0181004 A1 | 8/2005 | Hunter et al. |
| 2005/0181008 A1 | 8/2005 | Hunter et al. |
| 2005/0181011 A1 | 8/2005 | Hunter et al. |
| 2005/0181977 A1 | 8/2005 | Hunter et al. |
| 2005/0182479 A1 | 8/2005 | Bonsignore et al. |
| 2005/0183728 A1 | 8/2005 | Hunter et al. |
| 2005/0186242 A1 | 8/2005 | Hunter et al. |
| 2005/0186243 A1 | 8/2005 | Hunter et al. |
| 2005/0187579 A1 | 8/2005 | Danek et al. |
| 2005/0191331 A1 | 9/2005 | Hunter et al. |
| 2005/0203434 A1 | 9/2005 | Kassab |
| 2005/0203498 A1 | 9/2005 | Mon et al. |
| 2005/0209587 A1 | 9/2005 | Joye et al. |
| 2005/0228286 A1 | 10/2005 | Messerly et al. |
| 2005/0228415 A1 | 10/2005 | Gertner |
| 2005/0228460 A1 | 10/2005 | Levin et al. |
| 2005/0240117 A1 | 10/2005 | Zvuloni et al. |
| 2005/0267556 A1 | 12/2005 | Shuros et al. |
| 2006/0004323 A1 | 1/2006 | Chang |
| 2006/0084962 A1 | 4/2006 | Joye et al. |
| 2006/0085054 A1 | 4/2006 | Zikorus et al. |
| 2006/0095029 A1 | 5/2006 | Young et al. |
| 2006/0100618 A1 | 5/2006 | Chan et al. |
| 2006/0142790 A1 | 6/2006 | Gertner |
| 2006/0147492 A1 | 7/2006 | Hunter et al. |
| 2006/0149166 A1 | 7/2006 | Zvuloni |
| 2006/0171895 A1 | 8/2006 | Bucay-Couto |
| 2006/0182873 A1 | 8/2006 | Klisch et al. |
| 2006/0184221 A1 | 8/2006 | Stewart et al. |
| 2006/0195139 A1 | 8/2006 | Gertner |
| 2006/0206150 A1 | 9/2006 | Demarais et al. |
| 2006/0212027 A1 | 9/2006 | Marrouche et al. |
| 2006/0224153 A1 | 10/2006 | Fischell et al. |
| 2006/0240070 A1 | 10/2006 | Cromack et al. |
| 2006/0247611 A1 | 11/2006 | Abboud et al. |
| 2006/0247760 A1 | 11/2006 | Ganesan et al. |
| 2006/0271111 A1 | 11/2006 | Demarais et al. |
| 2006/0280858 A1 | 12/2006 | Kokish |
| 2007/0043409 A1 | 2/2007 | Brian et al. |
| 2007/0049924 A1 | 3/2007 | Rahn |
| 2007/0093710 A1 | 4/2007 | Maschke |
| 2007/0100405 A1 | 5/2007 | Thompson et al. |
| 2007/0129720 A1 | 6/2007 | Demarais et al. |
| 2007/0149963 A1 | 6/2007 | Matsukuma et al. |
| 2007/0162109 A1 | 7/2007 | Davila et al. |
| 2007/0179496 A1 | 8/2007 | Swoyer et al. |

(56) References Cited

U.S. PATENT DOCUMENTS

| | | |
|---|---|---|
| 2007/0185445 A1 | 8/2007 | Nahon et al. |
| 2007/0207186 A1 | 9/2007 | Scanlon et al. |
| 2007/0208256 A1 | 9/2007 | Marilla |
| 2007/0208301 A1 | 9/2007 | Evard et al. |
| 2007/0219576 A1 | 9/2007 | Cangialosi |
| 2007/0225781 A1 | 9/2007 | Saadat et al. |
| 2007/0233170 A1 | 10/2007 | Gertner |
| 2007/0239062 A1 | 10/2007 | Chopra et al. |
| 2007/0265687 A1 | 11/2007 | Deem et al. |
| 2007/0278103 A1 | 12/2007 | Hoerr et al. |
| 2007/0282302 A1 | 12/2007 | Wachsman et al. |
| 2007/0299433 A1 | 12/2007 | Williams et al. |
| 2008/0009927 A1 | 1/2008 | Vilims |
| 2008/0015501 A1 | 1/2008 | Gertner |
| 2008/0071306 A1 | 3/2008 | Gertner |
| 2008/0082109 A1 | 4/2008 | Moll et al. |
| 2008/0086072 A1 | 4/2008 | Bonutti et al. |
| 2008/0097251 A1 | 4/2008 | Babaev |
| 2008/0119879 A1 | 5/2008 | Brenneman et al. |
| 2008/0125772 A1 | 5/2008 | Stone et al. |
| 2008/0140002 A1 | 6/2008 | Ramzipoor et al. |
| 2008/0147002 A1 | 6/2008 | Gertner |
| 2008/0161717 A1 | 7/2008 | Gertner |
| 2008/0171974 A1 | 7/2008 | Lafontaine et al. |
| 2008/0172035 A1 | 7/2008 | Starksen et al. |
| 2008/0172104 A1 | 7/2008 | Kieval et al. |
| 2008/0208169 A1 | 8/2008 | Boyle et al. |
| 2008/0208182 A1 | 8/2008 | Lafontaine et al. |
| 2008/0245371 A1 | 10/2008 | Gruber |
| 2008/0255550 A1 | 10/2008 | Bell |
| 2008/0275484 A1 | 11/2008 | Gertner |
| 2008/0281347 A1 | 11/2008 | Gertner |
| 2008/0300584 A1 | 12/2008 | Lentz et al. |
| 2008/0300618 A1 | 12/2008 | Gertner |
| 2008/0306475 A1 | 12/2008 | Lentz et al. |
| 2008/0312644 A1 | 12/2008 | Fourkas et al. |
| 2008/0319513 A1 | 12/2008 | Pu et al. |
| 2009/0018486 A1 | 1/2009 | Goren et al. |
| 2009/0036948 A1 | 2/2009 | Levin et al. |
| 2009/0074828 A1 | 3/2009 | Alexis et al. |
| 2009/0118726 A1 | 5/2009 | Auth et al. |
| 2009/0143640 A1 | 6/2009 | Saadat et al. |
| 2009/0156988 A1 | 6/2009 | Ferren et al. |
| 2009/0157057 A1 | 6/2009 | Ferren et al. |
| 2009/0157161 A1 | 6/2009 | Desai et al. |
| 2009/0171333 A1 | 7/2009 | Hon |
| 2009/0182316 A1 | 7/2009 | Bencini |
| 2009/0182317 A1 | 7/2009 | Bencini |
| 2009/0203962 A1 | 8/2009 | Miller et al. |
| 2009/0209949 A1 | 8/2009 | Ingle et al. |
| 2009/0216317 A1 | 8/2009 | Cromack et al. |
| 2009/0221955 A1 | 9/2009 | Babaev |
| 2009/0234345 A1* | 9/2009 | Hon ................. A61B 18/02 606/21 |
| 2009/0247933 A1 | 10/2009 | Maor et al. |
| 2009/0248012 A1 | 10/2009 | Maor et al. |
| 2009/0270850 A1 | 10/2009 | Zhou et al. |
| 2009/0281533 A1 | 11/2009 | Ingle et al. |
| 2009/0287137 A1 | 11/2009 | Crowley |
| 2009/0287202 A1 | 11/2009 | Ingle et al. |
| 2009/0299355 A1 | 12/2009 | Bencini et al. |
| 2009/0318749 A1 | 12/2009 | Stolen et al. |
| 2010/0049184 A1 | 2/2010 | George et al. |
| 2010/0049186 A1 | 2/2010 | Ingle et al. |
| 2010/0049188 A1 | 2/2010 | Nelson et al. |
| 2010/0069837 A1 | 3/2010 | Rassat et al. |
| 2010/0069900 A1 | 3/2010 | Shirley et al. |
| 2010/0076425 A1 | 3/2010 | Carroux |
| 2010/0087782 A1 | 4/2010 | Ghaffari et al. |
| 2010/0100087 A1 | 4/2010 | Mazzone et al. |
| 2010/0106148 A1 | 4/2010 | Joye et al. |
| 2010/0114269 A1 | 5/2010 | Wittenberger et al. |
| 2010/0125266 A1 | 5/2010 | Deem et al. |
| 2010/0125268 A1 | 5/2010 | Gustus et al. |
| 2010/0130836 A1 | 5/2010 | Malchano et al. |
| 2010/0130970 A1 | 5/2010 | Williams et al. |
| 2010/0137860 A1 | 6/2010 | Demarais et al. |
| 2010/0137952 A1 | 6/2010 | Demarais et al. |
| 2010/0160906 A1 | 6/2010 | Jarrard |
| 2010/0168624 A1 | 7/2010 | Sliwa |
| 2010/0179526 A1 | 7/2010 | Lawrence |
| 2010/0179527 A1 | 7/2010 | Watson et al. |
| 2010/0191112 A1 | 7/2010 | Demarais et al. |
| 2010/0191232 A1 | 7/2010 | Boveda |
| 2010/0198203 A1 | 8/2010 | Kuck et al. |
| 2010/0204560 A1 | 8/2010 | Salahieh et al. |
| 2010/0222786 A1 | 9/2010 | Kassab |
| 2010/0222851 A1 | 9/2010 | Deem et al. |
| 2010/0222854 A1 | 9/2010 | Demarais et al. |
| 2010/0234838 A1 | 9/2010 | Watson |
| 2010/0249702 A1 | 9/2010 | Magana et al. |
| 2010/0249766 A1 | 9/2010 | Saadat |
| 2010/0256616 A1 | 10/2010 | Katoh et al. |
| 2010/0256621 A1 | 10/2010 | Babkin et al. |
| 2010/0268217 A1 | 10/2010 | Habib |
| 2010/0280507 A1 | 11/2010 | Babkin et al. |
| 2010/0298821 A1 | 11/2010 | Garbagnati |
| 2010/0324472 A1 | 12/2010 | Wulfman |
| 2011/0009750 A1 | 1/2011 | Taylor et al. |
| 2011/0125143 A1 | 5/2011 | Gross et al. |
| 2011/0137155 A1 | 6/2011 | Weber et al. |
| 2011/0146673 A1 | 6/2011 | Keast et al. |
| 2011/0166499 A1 | 7/2011 | Demarais et al. |
| 2011/0184400 A1* | 7/2011 | Pageard ................. A61B 18/02 606/21 |
| 2011/0190751 A1* | 8/2011 | Ingle ................... A61B 18/02 606/21 |
| 2011/0202098 A1 | 8/2011 | Demarais et al. |
| 2011/0257622 A1 | 10/2011 | Salahieh et al. |
| 2011/0257642 A1 | 10/2011 | Griggs, III |
| 2011/0270238 A1* | 11/2011 | Rizq ................... A61B 18/02 606/21 |
| 2011/0306851 A1 | 12/2011 | Wang |
| 2011/0319809 A1 | 12/2011 | Smith |
| 2012/0029496 A1 | 2/2012 | Smith |
| 2012/0029500 A1 | 2/2012 | Jenson |
| 2012/0029509 A1 | 2/2012 | Smith |
| 2012/0029511 A1 | 2/2012 | Smith et al. |
| 2012/0029512 A1 | 2/2012 | Willard et al. |
| 2012/0071870 A1 | 3/2012 | Salahieh et al. |
| 2012/0089047 A1 | 4/2012 | Ryba et al. |
| 2012/0109021 A1 | 5/2012 | Hastings et al. |
| 2012/0123261 A1 | 5/2012 | Jenson et al. |
| 2012/0130289 A1 | 5/2012 | Demarais et al. |
| 2012/0130345 A1 | 5/2012 | Levin et al. |
| 2012/0130360 A1 | 5/2012 | Buckley et al. |
| 2012/0130368 A1 | 5/2012 | Jenson |
| 2012/0136417 A1 | 5/2012 | Buckley et al. |
| 2012/0136418 A1 | 5/2012 | Buckley et al. |
| 2012/0143097 A1 | 6/2012 | Pike, Jr. |
| 2012/0143177 A1 | 6/2012 | Avitall |
| 2012/0150267 A1 | 6/2012 | Buckley et al. |
| 2012/0157992 A1 | 6/2012 | Smith et al. |
| 2012/0157993 A1 | 6/2012 | Jenson et al. |
| 2012/0172837 A1 | 7/2012 | Demarais et al. |
| 2012/0184952 A1 | 7/2012 | Jenson et al. |
| 2012/0191083 A1 | 7/2012 | Moll et al. |
| 2012/0253336 A1 | 10/2012 | Littrup et al. |
| 2012/0271277 A1 | 10/2012 | Fischell et al. |
| 2012/0296232 A1 | 11/2012 | Ng |
| 2012/0296329 A1 | 11/2012 | Ng |
| 2013/0012866 A1 | 1/2013 | Deem et al. |
| 2013/0012867 A1 | 1/2013 | Demarais et al. |
| 2013/0035681 A1 | 2/2013 | Subramaniam et al. |
| 2013/0053732 A1 | 2/2013 | Heuser |
| 2013/0066316 A1 | 3/2013 | Steinke et al. |
| 2013/0085493 A1 | 4/2013 | Bloom et al. |
| 2013/0090649 A1 | 4/2013 | Smith et al. |
| 2013/0090650 A1 | 4/2013 | Jenson et al. |
| 2013/0096604 A1 | 4/2013 | Hanson et al. |
| 2013/0116687 A1 | 5/2013 | Willard |
| 2013/0123770 A1 | 5/2013 | Smith |
| 2013/0123778 A1 | 5/2013 | Richardson et al. |
| 2013/0165916 A1 | 6/2013 | Mathur et al. |

(56) References Cited

U.S. PATENT DOCUMENTS

| | | |
|---|---|---|
| 2013/0165917 A1 | 6/2013 | Mathur et al. |
| 2013/0165923 A1 | 6/2013 | Mathur et al. |
| 2013/0165924 A1 | 6/2013 | Mathur et al. |
| 2013/0165925 A1 | 6/2013 | Mathur et al. |
| 2013/0165926 A1 | 6/2013 | Mathur et al. |
| 2013/0165990 A1 | 6/2013 | Mathur et al. |
| 2013/0172815 A1 | 7/2013 | Perry et al. |
| 2013/0172872 A1 | 7/2013 | Subramaniam et al. |
| 2013/0172877 A1 | 7/2013 | Subramaniam et al. |
| 2013/0172881 A1 | 7/2013 | Hill et al. |
| 2013/0184696 A1 | 7/2013 | Fourkas et al. |
| 2013/0231658 A1 | 9/2013 | Wang et al. |
| 2013/0231659 A1 | 9/2013 | Hill et al. |
| 2013/0253628 A1 | 9/2013 | Smith et al. |
| 2013/0274658 A1 | 10/2013 | Steinke et al. |
| 2013/0289555 A1 | 10/2013 | Mayse et al. |
| 2013/0289556 A1 | 10/2013 | Mayse et al. |
| 2013/0296853 A1 | 11/2013 | Sugimoto et al. |
| 2013/0304052 A1 | 11/2013 | Rizq et al. |
| 2013/0345688 A1 | 12/2013 | Babkin |
| 2014/0018794 A1 | 1/2014 | Anderson et al. |
| 2014/0018888 A1 | 1/2014 | Ostroot et al. |
| 2014/0046313 A1 | 2/2014 | Pederson et al. |
| 2014/0058374 A1 | 2/2014 | Edmunds et al. |
| 2014/0058376 A1 | 2/2014 | Horn et al. |
| 2014/0066914 A1 | 3/2014 | Lafontaine |
| 2014/0066921 A1 | 3/2014 | Coe et al. |
| 2014/0066924 A1 | 3/2014 | Azamian et al. |
| 2014/0074083 A1 | 3/2014 | Horn et al. |
| 2014/0074089 A1 | 3/2014 | Nishii |
| 2014/0128859 A1 | 5/2014 | Lee |
| 2014/0135661 A1 | 5/2014 | Garrison et al. |
| 2014/0135715 A1 | 5/2014 | Lambert et al. |
| 2014/0135755 A1 | 5/2014 | Sutermeister et al. |
| 2014/0180077 A1 | 6/2014 | Huennekens et al. |
| 2014/0180196 A1 | 6/2014 | Stone et al. |
| 2014/0188103 A1 | 7/2014 | Millett |
| 2014/0200578 A1 | 8/2014 | Salahieh et al. |
| 2014/0243821 A1 | 8/2014 | Salahieh et al. |
| 2014/0276724 A1 | 9/2014 | Goshayeshgar |
| 2014/0276728 A1 | 9/2014 | Goshayeshgar |
| 2014/0276811 A1 | 9/2014 | Koblish et al. |
| 2014/0378962 A1 | 12/2014 | Anderson et al. |
| 2014/0378966 A1 | 12/2014 | Haverkost et al. |
| 2014/0378968 A1 | 12/2014 | Sutermeister et al. |
| 2015/0005762 A1 | 1/2015 | Belk et al. |
| 2015/0005764 A1 | 1/2015 | Hanson et al. |
| 2015/0005799 A1 | 1/2015 | Lindquist et al. |
| 2015/0018817 A1 | 1/2015 | Willard |
| 2015/0018819 A1 | 1/2015 | Sutermeister |
| 2015/0025525 A1 | 1/2015 | Willard et al. |
| 2015/0025532 A1 | 1/2015 | Hanson et al. |
| 2015/0025533 A1 | 1/2015 | Groff et al. |
| 2015/0057656 A1 | 2/2015 | Gupta et al. |
| 2015/0057657 A1 | 2/2015 | Squire et al. |
| 2015/0066013 A1 | 3/2015 | Salahieh et al. |
| 2015/0066023 A1 | 3/2015 | Anderson et al. |
| 2015/0080882 A1 | 3/2015 | Skinner et al. |
| 2015/0080883 A1 | 3/2015 | Haverkost et al. |
| 2015/0105659 A1 | 4/2015 | Salahieh et al. |
| 2015/0105764 A1 | 4/2015 | Rizq et al. |
| 2015/0105773 A1 | 4/2015 | Weber et al. |
| 2015/0105774 A1 | 4/2015 | Lindquist et al. |
| 2015/0112328 A1 | 4/2015 | Willard et al. |
| 2015/0112329 A1 | 4/2015 | Ng |
| 2015/0119882 A1 | 4/2015 | Cao et al. |
| 2015/0148794 A1 | 5/2015 | Squire et al. |
| 2015/0148797 A1 | 5/2015 | Willard |
| 2015/0190194 A1 | 7/2015 | Weber et al. |
| 2015/0190195 A1 | 7/2015 | Hanson et al. |
| 2015/0196354 A1 | 7/2015 | Haverkost et al. |
| 2015/0201997 A1 | 7/2015 | Osypka |
| 2015/0216591 A1 | 8/2015 | Cao et al. |
| 2015/0265339 A1 | 9/2015 | Lindquist et al. |
| 2015/0289770 A1 | 10/2015 | Wang |
| 2015/0297292 A1 | 10/2015 | Sutermeister et al. |
| 2015/0342673 A1 | 12/2015 | Squire et al. |
| 2015/0366608 A1 | 12/2015 | Weber et al. |
| 2016/0015452 A1 | 1/2016 | Nabutovsky et al. |
| 2016/0022359 A1 | 1/2016 | Sugimoto et al. |
| 2016/0066992 A1 | 3/2016 | Mathur |
| 2016/0074112 A1 | 3/2016 | Himmelstein et al. |
| 2016/0106984 A1 | 4/2016 | Mathur et al. |
| 2016/0175582 A1 | 6/2016 | Serna et al. |
| 2016/0184010 A1 | 6/2016 | Nabutovsky et al. |
| 2016/0324574 A1 | 11/2016 | Willard |
| 2016/0331451 A1 | 11/2016 | Nabutovsky et al. |
| 2016/0367316 A1 | 12/2016 | Smith et al. |
| 2016/0374748 A9 | 12/2016 | Salahieh et al. |
| 2017/0000560 A1 | 1/2017 | Mathur et al. |

FOREIGN PATENT DOCUMENTS

| | | |
|---|---|---|
| CN | 103549993 A | 2/2014 |
| DE | 4406451 | 9/1995 |
| DE | 29909082 | 7/1999 |
| DE | 10252325 | 5/2004 |
| DE | 10257146 | 6/2004 |
| DE | 102005041601 | 4/2007 |
| DE | 20 2004 021 941 | 5/2013 |
| DE | 20 2004 021 942 | 5/2013 |
| DE | 20 2004 021 949 | 5/2013 |
| DE | 20 2004 021 951 | 6/2013 |
| DE | 20 2004 021 952 | 6/2013 |
| DE | 20 2004 021 953 | 6/2013 |
| DE | 20 2004 021 944 | 7/2013 |
| EP | 0655225 | 5/1995 |
| EP | 0955012 | 11/1999 |
| EP | 1129670 | 9/2001 |
| EP | 1164963 | 1/2002 |
| EP | 1389477 | 2/2004 |
| EP | 1502553 | 2/2005 |
| EP | 1559362 | 8/2005 |
| EP | 1559362 A2 | 8/2005 |
| EP | 1667595 | 6/2006 |
| EP | 1865870 | 12/2007 |
| EP | 1948301 | 7/2008 |
| EP | 1009303 | 6/2009 |
| EP | 2076193 | 7/2009 |
| EP | 2076194 | 7/2009 |
| EP | 2076198 | 7/2009 |
| EP | 2341839 | 7/2011 |
| EP | 2352542 | 8/2011 |
| EP | 2355737 | 8/2011 |
| EP | 2370015 | 10/2011 |
| EP | 2429641 | 3/2012 |
| EP | 2438877- | 4/2012 |
| EP | 2452648 | 5/2012 |
| EP | 2455034 | 5/2012 |
| EP | 2455035 | 5/2012 |
| EP | 2455036 | 5/2012 |
| EP | 2519173 | 11/2012 |
| EP | 2555699 | 2/2013 |
| EP | 2558016 | 2/2013 |
| EP | 2558016 A2 | 2/2013 |
| EP | 2568905 | 3/2013 |
| EP | 2598068 | 6/2013 |
| EP | 2598070 | 6/2013 |
| EP | 2598070 A1 | 6/2013 |
| EP | 2598071 | 6/2013 |
| EP | 2598071 A2 | 6/2013 |
| EP | 2608837 | 7/2013 |
| EP | 2608837 A2 | 7/2013 |
| EP | 2656807 | 10/2013 |
| EP | 2694150 | 2/2014 |
| EP | 2694158 | 2/2014 |
| EP | 2701795 | 3/2014 |
| EP | 2709517 A1 | 3/2014 |
| EP | 2731531 | 5/2014 |
| EP | 2755588 | 7/2014 |
| EP | 2760532 | 8/2014 |
| EP | 2793724 A2 | 10/2014 |
| EP | 2818129 A1 | 12/2014 |
| EP | 2836151 A2 | 2/2015 |

(56) References Cited

FOREIGN PATENT DOCUMENTS

| | | | |
|---|---|---|---|
| EP | 2848225 A1 | 3/2015 |
| EP | 2851027 A1 | 3/2015 |
| EP | 2872064 A1 | 5/2015 |
| EP | 2895093 A1 | 7/2015 |
| EP | 2914328 A1 | 9/2015 |
| EP | 2967734 A1 | 1/2016 |
| EP | 3003191 A1 | 4/2016 |
| EP | 3010435 A1 | 4/2016 |
| EP | 3010437 A1 | 4/2016 |
| EP | 3016605 A1 | 5/2016 |
| EP | 3019103 A1 | 5/2016 |
| EP | 3019106 A1 | 5/2016 |
| EP | 3024405 A1 | 6/2016 |
| EP | 3024406 A1 | 6/2016 |
| EP | 3035878 A1 | 6/2016 |
| EP | 3035879 A1 | 6/2016 |
| EP | 3041425 A1 | 7/2016 |
| EP | 3043733 A1 | 7/2016 |
| EP | 3049007 A1 | 8/2016 |
| EP | 3057520 A1 | 8/2016 |
| EP | 3057521 A1 | 8/2016 |
| EP | 3060153 A1 | 8/2016 |
| EP | 3091922 A1 | 11/2016 |
| EP | 3091923 A1 | 11/2016 |
| EP | 3091924 A1 | 11/2016 |
| EP | 3102136 A1 | 12/2016 |
| GB | 228367 | 2/1925 |
| GB | 1422535 | 1/1976 |
| GB | 1422535 A | 1/1976 |
| GB | 2283678 | 5/1995 |
| GB | 2283678 A | 5/1995 |
| GB | 2289414 | 11/1995 |
| GB | 2289414 A | 11/1995 |
| JP | 2016086998 A | 5/2016 |
| SU | 718099 | 2/1980 |
| SU | 1153901 | 5/1985 |
| SU | 1329781 | 8/1987 |
| SU | 1329781 A2 | 8/1987 |
| SU | 1378835 | 3/1988 |
| SU | 1771725 | 6/1990 |
| SU | 1771725 | 5/2001 |
| WO | WO-199211898 | 7/1992 |
| WO | WO-1992020291 | 11/1992 |
| WO | WO-1994007446 | 4/1994 |
| WO | WO-199510319 | 4/1995 |
| WO | WO-1995025472 | 9/1995 |
| WO | WO-9531142 | 11/1995 |
| WO | WO-199634559 | 11/1996 |
| WO | WO-9725011 | 7/1997 |
| WO | WO-199725011 | 7/1997 |
| WO | WO-1997036548 | 10/1997 |
| WO | WO-1998042403 | 10/1998 |
| WO | WO-1999/00060 | 1/1999 |
| WO | WO-9900060 | 1/1999 |
| WO | WO-9905979 | 2/1999 |
| WO | WO-199905979 | 2/1999 |
| WO | WO-9927862 | 6/1999 |
| WO | WO-1999027862 | 6/1999 |
| WO | WO-199952424 | 10/1999 |
| WO | WO-1999062413 | 12/1999 |
| WO | WO-0047118 | 8/2000 |
| WO | WO-0122897 | 4/2001 |
| WO | WO-2001022897 | 4/2001 |
| WO | WO-0164145 | 9/2001 |
| WO | WO-2001064145 | 9/2001 |
| WO | WO-2001070114 | 9/2001 |
| WO | WO-2002000128 | 1/2002 |
| WO | WO-2002004042 | 1/2002 |
| WO | WO-2002007625 | 1/2002 |
| WO | WO-2002007628 | 1/2002 |
| WO | WO-0213710 | 2/2002 |
| WO | WO-0215807 | 2/2002 |
| WO | WO-2002013710 | 2/2002 |
| WO | WO-0204042 | 5/2002 |
| WO | WO-02058576 | 8/2002 |
| WO | WO-2002058576 | 8/2002 |
| WO | WO-03020334 A2 | 3/2003 |
| WO | WO-2003020334 | 3/2003 |
| WO | WO-2003022167 | 3/2003 |
| WO | WO-03061496 | 7/2003 |
| WO | WO-2003061496 | 7/2003 |
| WO | WO-2003/082080 | 10/2003 |
| WO | WO-2005030072 | 4/2005 |
| WO | WO-2005037070 | 4/2005 |
| WO | WO-2005038357 | 4/2005 |
| WO | WO-2005038357 A2 | 4/2005 |
| WO | WO-2005041748 | 5/2005 |
| WO | WO--2005041748 | 5/2005 |
| WO | WO-2005110528 | 11/2005 |
| WO | WO-2006041881 | 4/2006 |
| WO | WO-2006096272 | 9/2006 |
| WO | WO-2006124177 | 11/2006 |
| WO | WO-2007008954 | 1/2007 |
| WO | WO-0207625 | 7/2007 |
| WO | WO-2007078997 A2 | 7/2007 |
| WO | WO-2008049084 A2 | 4/2008 |
| WO | WO-0207628 | 7/2008 |
| WO | WO-2008131037 | 10/2008 |
| WO | WO-2008131037 A2 | 10/2008 |
| WO | WO-2009121017 | 10/2009 |
| WO | WO-0200128 | 5/2010 |
| WO | WO-2011056684 | 5/2011 |
| WO | WO-2011056684 A2 | 5/2011 |
| WO | WO-2011082278 | 7/2011 |
| WO | WO-2011082279 | 7/2011 |
| WO | WO-2011082279 A2 | 7/2011 |
| WO | WO-2011119857 | 9/2011 |
| WO | WO-2011126580 | 10/2011 |
| WO | WO-2011130534 | 10/2011 |
| WO | WO-2011143468 | 11/2011 |
| WO | WO-2012016135 | 2/2012 |
| WO | WO-2012016137 | 2/2012 |
| WO | WO-2012016137 A2 | 2/2012 |
| WO | WO-2012058430 | 5/2012 |
| WO | WO-2012058430 A2 | 5/2012 |
| WO | WO-2012075156 | 6/2012 |
| WO | WO-2012122157 | 9/2012 |
| WO | WO-2012130337 | 10/2012 |
| WO | WO-2012131107 | 10/2012 |
| WO | WO-2012135703 | 10/2012 |
| WO | WO-2012161875 | 11/2012 |
| WO | WO-2012174375 | 12/2012 |
| WO | WO-2013013156 | 1/2013 |
| WO | WO-2013028812 | 2/2013 |
| WO | WO-2013040201 | 3/2013 |
| WO | WO-2013/055685 | 4/2013 |
| WO | WO-2013049601 | 4/2013 |
| WO | WO-2013070724 | 5/2013 |
| WO | WO-2013074683 | 5/2013 |
| WO | WO-2013077283 | 5/2013 |
| WO | WO-2013096913 | 6/2013 |
| WO | WO-2013096916 | 6/2013 |
| WO | WO-2013096919 | 6/2013 |
| WO | WO-2013096920 | 6/2013 |
| WO | WO-2013096922 | 6/2013 |
| WO | WO-2013101446 | 7/2013 |
| WO | WO-2013101452 | 7/2013 |
| WO | WO2013106859 | 7/2013 |
| WO | WO-2013106859 | 7/2013 |
| WO | WO-2013112844 | 8/2013 |
| WO | WO-2013/131046 | 9/2013 |
| WO | WO-2013154775 | 10/2013 |
| WO | WO-2014022379 | 2/2014 |
| WO | WO 2014036160 | 3/2014 |
| WO | WO-2014056460 | 4/2014 |
| WO | WO-2014059165 | 4/2014 |
| WO | WO-2014071223 | 5/2014 |
| WO | WO-2014078301 | 5/2014 |
| WO | WO-2014096969 | 6/2014 |
| WO | WO-2014100226 | 6/2014 |
| WO | WO-2014110579 | 7/2014 |
| WO | WO-2014150204 | 9/2014 |

(56) References Cited

FOREIGN PATENT DOCUMENTS

| WO | WO-2014158727 | 10/2014 |
|---|---|---|
| WO | WO-2014164445 | 10/2014 |

OTHER PUBLICATIONS

International Search Report and Written Opinion for International Application No. PCT/US2011/046845, dated Dec. 16, 2011, 16 pages.
Beale et al., "Minimally Invasive Treatment for Varicose Veins: A Review of Endovenous Laser Treatment and Radiofrequency Ablation". Lower Extremity Wounds 3(4), 2004, 10 pages.
Eick, Olaf, "Temperature Controlled Radiofrequency Ablation." Indian Pacing and Electrophysiology Journal, vol. 2. No. 3, 2002, 8 pages.
European Search Report dated Feb. 22, 2013; Application No. 12180432.2; Applicant: Medtronic Ardian Luxembourg S.a.r.l.; 6 pages.
European Search Report dated Feb. 28, 2013; European Application No. 12180427.2; Applicant: Medtronic Ardian Luxembourg S.a.r.l.; 4 pages.
European Search Report dated May 3, 2012; European Patent Application No. 11192514.5; Applicant: Ardian, Inc.; 7 pages.
European Search Report dated Jan. 30, 2013; Application No. 12180428.0; Applicant: Medtronic Ardian Luxembourg S.a.r.l.; 6 pages.
European Search Report dated Jan. 30, 2013; Application No. 12180430.6; Applicant: Medtronic Ardian Luxembourg S.a.r.l.; 6 pages.
European Search Report dated Jan. 30, 2013; Application No. 12180431.4; Applicant: Medtronic Ardian Luxembourg S.a.r.l.; 6 pages.
European Search Report dated Jan. 30, 2013; European Application No. 12180426.4; Applicant: Medtronic Ardian Luxembourg S.a.r.l.; 6 pages.
European Search Report dated May 3, 2012; European Patent Application No. 11192511.1; Applicant: Ardain, Inc.; 6 pages.
Pieper et al., "Design and implementation of a new computerized system for intraoperative cardiac mapping." the American Physiological Society. 1991, 12 pages.
Allen, E.V., Sympathectomy for essential hypertension, Circulation, 1952, 6:131-140.
Bello-Reuss, E. et al., "Effects of Acute Unilateral Renal Denervation in the Rat," Journal of Clinical Investigation, vol. 56, Jul. 1975, pp. 208-217.
Bello-Reuss, E. et al., "Effects of Renal Sympathetic Nerve Stimulation on Proximal Water and Sodium Reabsorption," Journal of Clinical Investigation, vol. 57, Apr. 1976, pp. 1104-1107.
Bhandari, A. and Ellias, M., "Loin Pain Hemaluria Syndrome: Pain Control with RFA to the Splanchanic Plexus," The Pain Clinc, 2000, vol. 12, No. 4, pp. 323-327.
Curtis, John J. et al., "Surgical Therapy for Persistent Hypertension After Renal Transplantation" Transplantation, 31:125-128 (1981).
Dibona, Gerald F. et al., "Neural Control of Renal Function," Physiological Reviews, vol. 77, No. 1, Jan. 1997, The American Physiological Society 1997, pp. 75-197.
Dibona, Gerald F., "Neural Control of the Kidney—Past, Present and Future," Nov. 4, 2002, Novartis Lecture, Hypertension 2003, 41 part 2, 2002 American Heart Association, Inc., pp. 621-624.
Janssen, Ben J.A. et al., "Effects of Complete Renal Denervation and Selective Afferent Renal Denervation on the Hypertension Induced by Intrenal Norepinephrine Infusion in Conscious Rats", Journal of Hypertension 1989, 7: 447-455.
Katholi, Richard E., "Renal Nerves in the Pathogenesis of Hypertension in Experimental Animals and Humans," Am J. Physiol. vol. 245, 1983, the American Physiological Society 1983, pp. F1-F14.
Krum, Henry et al., "Catheter-Based Renal Sympathetic Denervation for Resistant Hypertension: A Mulitcentre Safety and Proof-of Principle Cohort Study," Lancet 2009; 373:1275-81.
Krum, et al., "Renal Sympathetic-Nerve Ablation for Uncontrolled Hypertension." New England Journal of Med, Aug. 2009, 361;9.
Luippold, Gerd et al., "Chronic Renal Denervation Prevents Glomerular Hyperfiltration in Diabetic Rats", Nephrol Dial Transplant, vol. 19, No. 2, 2004, pp. 342-347.
Mahfoud et al. "Treatment strategies for resistant arterial hypertension" Dtsch Arztebl Int. 2011;108:725-731.
Osborn, et al., "Effect of Renal Nerve Stimulation on Renal Blood Flow Autoregulation and Antinatriuresis During Reductions in Renal Perfusion Pressure," Proceedings of the Society for Experimentla Biology and Medicine, vol. 168, 77-81, 1981.
Page, I.H. et al., "The Effect of Renal Denervation on Patients Suffering From Nephritis," Feb. 27, 1935;443-458.
Page, I.H. et al., "The Effect of Renal Denervation on the Level of Arterial Blood Pressure and Renal Function in Essential Hypertension," J. Clin Invest. 1934;14:27-30.
Rocha-Singh, "Catheter-Based Sympathetic Renal Denervation," Endovascular Today, Aug. 2009.
Schlaich, M.P. et al., "Renal Denervation as a Therapeutic Approach for Hypertension: Novel Implictions for an Old Concept," Hypertension, 2009; 54:1195-1201.
Schlaich, M.P. et al., "Renal Sympathetic-Nerve Ablation for Uncontrolled Hypertension," N Engl J Med 2009; 361(9): 932-934.
Smithwick, R.H. et al., "Splanchnicectomy for Essential Hypertension," Journal Am Med Assn, 1953; 152:1501-1504.
Symplicity HTN-1 Investigators; Krum H, Barman N, Schlaich M, et al. Catheter-based renal sympathetic denervation for resistant hypertension: durability of blood pressure reduction out to 24 months. Hypertension. 2011;57(5):911-917.
Symplicity HTN-2 Investigators, "Renal Sympathetic Denervation in Patients with Treatment-Resistant Hypertension (The Symplicity HTN-2 Trial): A Randomised Controlled Trial"; Lancet, Dec. 4, 2010, vol. 376, pp. 1903-1909.
United States Renal Data System, USRDS 2003 Annual Data Report: Atlas of End-Stage Renal Disease in the United States, National Institutes of Health, National Institute of Diabetes and Digestive and Kidney Diseases, 2003, 593 pages.
Valente, John F. et al., "Laparoscopic Renal Denervation for Intractable ADPKD-Related Pain", Nephrol Dial Transplant (2001) 16:160.
Wagner, C.D. et al., "Very Low Frequency Oscillations in Arterial Blood Pressure After Autonomic Blockade in Conscious Dogs," Feb. 5, 1997, Am J Physiol Regul Integr Comp Physiol 1997, vol. 272, 1997 the American Physiological Society, pp. 2034-2039.
Ahmed, Humera et al., Renal Sympathetic Denervation Using an Irrigated Radiofrequency Ablation Catheter for the Management of Drug-Resistant Hypertension, JACC Cardiovascular Interventions, vol. 5, No. 7, 2012, pp. 758-765.
Avitall et al., "The creation of linear contiguous lesions in the atria with an expandable loop catheter," Journal of the American College of Cardiology, 1999; 33; pp. 972-984.
Blessing, Erwin et al., Cardiac Ablation and Renal Denervation Systems Have Distinct Purposes and Different Technical Requirements, JACC Cardiovascular Interventions, vol. 6, No. 3, 2013, 1 page.
ClinicalTrials.gov, Renal Denervation in Patients with uncontrolled Hypertension in Chinese (2011), 6pages. www.clinicaltrials.gov/ct2/show/NCT01390831.
Excerpt of Operator's Manual of Boston Scientific's EPT-1000 XP Cardiac Ablation Controller & Accessories, Version of Apr. 2003, (6 pages).
Excerpt of Operator's Manual of Boston Scientific's Maestro 30000 Cardiac Ablation System, Version of Oct. 17, 2005 , (4 pages).
Holmes et al., Pulmonary Vein Stenosis Complicating Ablation for Atrial Fibrillation: Clinical Spectrum and Interventional Considerations, JACC: Cardiovascular Interventions, 2: 4, 2009, 10 pages.
Kandarpa, Krishna et al., "Handbook of Interventional Radiologic Procedures", Third Edition, pp. 194-210 (2002).
Mount Sinai School of Medicine clinical trial for Impact of Renal Sympathetic Denervation of Chronic Hypertension, Mar. 2013, 11 pages. http://clinicaltrials.gov/ct2/show/NCT01628198.
Opposition to European Patent No. EP1802370, Granted Jan. 5, 2011, Date of Opposition Oct. 5, 2011, 20 pages.

(56) References Cited

OTHER PUBLICATIONS

Opposition to European Patent No. EP2037840, Granted Dec. 7, 2011, Date of Opposition Sep. 7, 2012, 25 pages.
Opposition to European Patent No. EP2092957, Granted Jan. 5, 2011, Date of Opposition Oct. 5, 2011, 26 pages.
Oz, Mehmet, Pressure Relief, TIME, Jan. 9, 2012, 2 pages. <www.time.come/time/printout/0,8816,2103278,00.html>.
Papademetriou, Vasilios, Renal Sympathetic Denervation for the Treatment of Difficult-to-Control or Resistant Hypertension, Int. Journal of Hypertension, 2011, 8 pages.
Prochnau, Dirk et al., Catheter-based renal denervation for drug-resistant hypertension by using a standard electrophysiology catheter; Euro Intervention 2012, vol. 7, pp. 1077-1080.
Purerfellner, Helmut et al., Incidence, Management, and Outcome in Significant Pulmonary Vein Stenosis Complicating Ablation for Atrial Fibrillation, Am. J. Cardiol , 93, Jun. 1, 2004, 4 pages.
Purerfellner, Helmut et al., Pulmonary Vein Stenosis Following Catheter Ablation of Atrial Fibrillation, Curr. Opin. Cardio. 20 :484-490, 2005.
Schneider, Peter A., "Endovascular Skills—Guidewire and Catheter Skills for Endovascular Surgery," Second Edition Revised and Expanded, 10 pages, (2003).
ThermoCool Irrigated Catheter and Integrated Ablation System, Biosense Webster (2006), 6 pages.
Tsao, Hsuan-Ming, Evaluation of Pulmonary Vein Stenosis after Catheter Ablation of Atrial Fibrillation, Cardiac Electrophysiology Review, 6, 2002, 4 pages.
Wittkampf et al., "Control of radiofrequency lesion size by power regulation," Journal of the American Heart Associate, 1989, 80: pp. 962-968.
Zheng et al., "Comparison of the temperature profile and pathological effect at unipolar, bipolar and phased radiofrequency current configurations," Journal of Interventional Cardiac Electrophysiology, 2001, pp. 401-410.
510K Summary of CryoGen Cryosurgery System, filed with FDA Jul. 3, 1997—approved Oct. 1, 1997, 1997, 5 pages.
CO2/Gas Composite Regulator, Sep. 6, 2011, 2 pages. <http://www.genuineinnovations.com/composite-regulator.html>.
CryoGen SS&E: HerOption Uterine Cryoblatin Therapy System, filed with FDA Aug. 15, 2000—approved Apr. 20, 2001, 1999, 84 pages.
International Search Report and Written Opinion dated Apr. 12, 2012, International Application No. PCT/US2011/057514, 15 pages.
International Search Report and Written Opinion dated Apr. 13, 2012, International Application No. PCT/US2011/057502, 14 pages.
International Search Report and Written Opinion dated Dec. 28, 2011, International Application No. PCT/US2011/057508, 12 pages.
International Search Report and Written Opinion dated Feb. 14, 2012, International Application No. PCT/US2011/057504, 12 pages.
International Search Report and Written Opinion dated Feb. 20, 2012, International Application No. PCT/US2011/057483, 11 pages.
International Search Report and Written Opinion dated Feb. 23, 2012, International Application No. PCT/US2011/057490, 14 pages.
International Search Report and Written Opinion dated Feb. 6, 2012, International Application No. PCT/US2011/057497, 12 pages.
International Search Report and Written Opinion dated Jun. 13, 2013, International Application No. PCT/US2012/063411, 13 pages.
International Search Report and Written Opinion dated Mar. 16, 2012, International Application No. PCT/US2011/057511, 16 pages.
International Search Report and Written Opinion dated Mar. 9, 2012, International Application No. PCT/US2011/057523, 15 pages.
Lura Harrison, Ph.D. et al., "Cryosurgical Ablation of the A-V Node-His Bundle—A New Method for Producing A-V Block," Circulation, vol. 55, 1977 pp. 463-470.
Medical Grade Gas Dispenser, Sep. 6, 2011, 1 page, <http://www.abd-inc.com/Frame-904990-page1namepage904990.html?refresh=1205442262133>.
Sesia G. et al., "The use of nitrous oxide as a freezing agent in cryosurgery of the prostate," International Surgery [Int Surg], vol. 53, 1970, pp. 82-90.

Special Order Only Thermal Dilution Injector, Obsolete Product, Sep. 6, 2011, 1 page, <http://www.abd-inc.com/Frame-904990-page1namepage904990.html?refresh=1205442262133>.
Torre, Douglas, MD, "Alternate Cryogens for Cryosurgery," J. Derm. Surgery, Jun. 1975, pp. 56-58.
Voĭtyna SV, "Cryocatheter-tourniquet," Meditsinskaia Tekhnika [Med Tekh], vol. 6, 1976, pp. 47-48.
European Search Report for European Application No. 13159256, dated Oct. 17, 2013, 6 pages.
International Search Report and Written Opinion for International App. No. PCT/US2012/034917, dated Nov. 14, 2012, 13 pages.
U.S. Appl. No. 95/002,110, filed Aug. 29, 2012, Demarais et al.
U.S. Appl. No. 95/002,209, filed Sep. 13, 2012, Levin et al.
U.S. Appl. No. 95/002,233, filed Sep. 13, 2012, Levin et al.
U.S. Appl. No. 95/002,243, filed Sep. 13, 2012, Levin et al.
U.S. Appl. No. 95/002,253, filed Sep. 13, 2012, Demarais et al.
U.S. Appl. No. 95/002,255, filed Sep. 13, 2012, Demarais et al.
U.S. Appl. No. 95/002,292, filed Sep. 14, 2012, Demarais et al.
U.S. Appl. No. 95/002,327, filed Sep. 14, 2012, Demarais et al.
U.S. Appl. No. 95/002,335, filed Sep. 14, 2012, Demarais et al.
U.S. Appl. No. 95/002,336, filed Sep. 14, 2012, Levin et al.
U.S. Appl. No. 95/002,356, filed Sep. 14, 2012, Demarais et al.
"2011 Edison Award Winners." Edison Awards: Honoring Innovations & Innovators, 2011, 6 pages, <http://www.edisonawards.com/BestNewProduct_2011.php>.
"2012 top 10 advances in heart disease and stroke research: American Heart Association/America Stroke Association Top 10 Research Report." American Heart Association, Dec. 17, 2012, 5 pages, <http://newsroom.heart.org/news/2012-top-10-advances-in-heart-241901>.
"Ardian(R) Receives 2010 EuroPCR Innovation Award and Demonstrates Further Durability of Renal Denervation Treatment for Hypertension." PR Newswire, Jun. 3, 2010, 2 pages, <http://www.prnewswire.com/news-releases/ardianr-receives-2010-europcr-innovation-award-and-demonstrates-further-durability-of-renal-denervation-treatment-for-hypertension-95545014.html>.
"Boston Scientific to Acquire Vessix Vascular, Inc.: Company to Strengthen Hypertension Program with Acquisition of Renal Denervation Technology." Boston Scientific: Advancing science for life—Investor Relations, Nov. 8, 2012, 2 pages, <http://phx.corporate-ir.net/phoenix.zhtml?c=62272&p=irol-newsArticle&id=1756108>.
"Cleveland Clinic Unveils Top 10 Medical Innovations for 2012: Experts Predict Ten Emerging Technologies that will Shape Health Care Next Year." Cleveland Clinic, Oct. 6, 2011, 2 pages. <http://my.clevelandclinic.org/media_relations/library/2011/2011-10-6-cleveland-clinic-unveils-top-10-medical-innovations-for-2012.aspx>.
"Does renal denervation represent a new treatment option for resistant hypertension?" Interventional News, Aug. 3, 2010, 2 pages. <http://www.cxvascular.com/in-latest-news/interventional-news---latest-news/does-renal-denervation-represent-a-new-treatment-option-for-resistant-hypertension>.
"Iberis—Renal Sympathetic Denervation System: Turning innovation into quality care." [Brochure], Terumo Europe N.V., 2013, Europe, 3 pages.
"Neurotech Reports Announces Winners of Gold Electrode Awards." Neurotech business report, 2009. 1 page. <http://www.neurotechreports.com/pages/goldelectrodes09.html>.
"Quick. Consistent. Controlled. OneShot renal Denervation System" [Brochure], Covidien: positive results for life, 2013, (n.l.), 4 pages.
"Renal Denervation Technology of Vessix Vascular, Inc. been acquired by Boston Scientific Corporation (BSX) to pay up to $425 Million." Vessix Vascular Pharmaceutical Intelligence: A blog specializing in Pharmaceutical Intelligence and Analytics, Nov. 8, 2012, 21 pages, <http://pharmaceuticalintelligence.com/tag/vessix-vascular/>.
"The Edison Awards™" Edison Awards: Honoring Innovations & Innovators, 2013, 2 pages, <http://www.edisonawards.com/Awards.php>.
"The Future of Renal denervation for the Treatment of Resistant Hypertension." St. Jude Medical, Inc., 2012, 12 pages.

(56) References Cited

OTHER PUBLICATIONS

"Vessix Renal Denervation System: So Advanced It's Simple." [Brochure], Boston Scientific: Advancing science for life, 2013, 6 pages.

Asbell, Penny, "Conductive Keratoplasty for the Correction of Hyperopia." Tr Am Ophth Soc, 2001, vol. 99, 10 pages.

Badoer, Emilio, "Cardiac afferents play the dominant role in renal nerve inhibition elicited by volume expansion in the rabbit." Am J Physiol Regul Integr Comp Physiol, vol. 274, 1998, 7 pages.

Bengel, Frank, "Serial Assessment of Sympathetic Reinnervation After Orthotopic Heart Transplantation: A longitudinal Study Using PET and C-11 Hydroxyephedrine." Circulation, vol. 99, 1999,7 pages.

Benito, F., et al. "Radiofrequency catheter ablation of accessory pathways in infants." Heart, 78:160-162 (1997).

Bettmann, Michael, Carotid Stenting and Angioplasty: A Statement for Healthcare Professionals From the Councils on Cardiovascular Radiology, Stroke, Cardio-Thoracic and Vascular Surgery, Epidemiology and Prevention, and Clinical Cardiology, American Heart Association, Circulation, vol. 97, 1998, 4 pages.

Bohm, Michael et al., "Rationale and design of a large registry on renal denervation: the Global SYMPLICITY registry." EuroIntervention, vol. 9, 2013, 9 pages.

Brosky, John, "EuroPCR 2013: CE-approved devices line up for renal denervation approval." Medical Device Daily, May 28, 2013, 3 pages, <http://www.medicaldevicedaily.com/servlet/com.accumedia.web.Dispatcher?next=bioWorldHeadlines_article&forceid=83002>.

Davis, Mark et al., "Effectiveness of Renal Denervation Therapy for Resistant Hypertension." Journal of the American College of Cardiology, vol. 62, No. 3, 2013, 11 pages.

Dibona, G.F. "Sympathetic nervous system and kidney in hypertension." Nephrol and Hypertension, 11: 197-200 (2002).

Dubuc, M., et al., "Feasibility of cardiac cryoablation using a transvenous steerable electrode catheter." J Interv Cardiac Electrophysiol, 2:285-292 (1998).

Final Office Action; U.S. Appl. No. 12/827,700; dated Feb. 5, 2013, 61 pages.

Geisler, Benjamin et al., "Cost-Effectiveness and Clinical Effectiveness of Catheter-Based Renal Denervation for Resistant Hypertension." Journal of the American College of Cardiology, col. 60, No. 14, 2012, 7 pages.

Gelfand, M., et al., "Treatment of renal failure and hypertension." U.S. Appl. No. 60/442,970, filed Jan. 29, 2003, 23 pages.

Gertner, Jon, "Meet the Tech Duo That's Revitalizing the Medical Device Industry." Fast Company, Apr. 15, 2013, 6:00 AM, 17 pages, <http://www.fastcompany.com/3007845/meet-tech-duo-thats-revitalizing-medical-device-industry>.

Golwyn, D. H., Jr., et al. "Percutaneous Transcatheter Renal Ablation with Absolute Ethanol for Uncontrolled Hypertension or Nephrotic Syndrome: Results in 11 Patients with End-Stage Renal Disease." JVIR, 8: 527-533 (1997).

Hall, W. H., et al. "Combined embolization and percutaneous radiofrequency ablation of a solid renal tumor." Am. J. Roentgenol,174: 1592-1594 (2000).

Han, Y.-M, et al., "Renal artery ebolization with diluted hot contrast medium: An experimental study." J Vasc Interv Radiol, 12: 862-868 (2001).

Hansen, J. M., et al. "The transplanted human kidney does not achieve functional reinnervation." Clin. Sci, 87: 13-19 (1994).

Hendee, W. R. et al. "Use of Animals in Biomedical Research: The Challenge and Response." *American Medical Association White Paper* (1988) 39 pages.

Hering, Dagmara et al., "Chronic kidney disease: role of sympathetic nervous system activation and potential benefits of renal denervation." EuroIntervention, vol. 9, 2013, 9 pages.

Huang et al., "Renal denervation prevents and reverses hyperinsulinemia-induced hypertension in rats." Hypertension 32 (1998) pp. 249-254.

Imimdtanz, "Medtronic awarded industry's highest honour for renal denervation system." The official blog of Medtronic Australasia, Nov. 12, 2012, 2 pages, <http://97waterlooroad.wordpress.com/2012/11/12/medtronic-awarded-industrys-highest-honour-for-renal-denervation-system/>.

Kaiser, Chris, AHA Lists Year's Big Advances in CV Research, medpage Today, Dec. 18, 2012, 4 pages, <http://www.medpagetoday.com/Cardiology/PCI/36509>.

Kompanowska, E., et al., "Early Effects of renal denervation in the anaesthetised rat: Natriuresis and increased cortical blood flow." J Physiol, 531. 2:527-534 (2001).

Lee, S.J., et al. "Ultrasonic energy in endoscopic surgery." Yonsei Med J, 40:545-549 (1999).

Linz, Dominik et al., "Renal denervation suppresses ventricular arrhythmias during acute ventricular ischemia in pigs." Heart Rhythm, vol. 0, No. 0, 2013, 6 pages.

Lustgarten, D.L.,et al., "Cryothermal ablation: Mechanism of tissue injury and current experience in the treatment of tachyarrhythmias." Progr Cardiovasc Dis, 41:481-498 (1999).

Mabin, Tom et al., "First experience with endovascular ultrasound renal denervation for the treatment of resistant hypertension." EuroIntervention, vol. 8, 2012, 5 pages.

Mahfoud, Felix et al., "Ambulatory Blood Pressure Changes after Renal Sympathetic Denervation in Patients with Resistant Hypertension." Circulation, 2013, 25 pages.

Mahfoud, Felix et al., "Expert consensus document from the European Society of Cardiology on catheter-based renal denervation." European Heart Journal, 2013, 9 pages.

Mahfoud, Felix et al., "Renal Hemodynamics and Renal Function After Catheter-Based Renal Sympathetic Denervation in Patients With Resistant Hypertension." Hypertension, 2012, 6 pages.

Medical-Dictionary.com, Definition of "Animal Model," http://medical-dictionary.com (search "Animal Model"), 2005, 1 page.

Medtronic, Inc., Annual Report (Form 10-K) (Jun. 28, 2011) 44 pages.

Millard, F. C., et al, "Renal Embolization for ablation of function in renal failure and hypertension." Postgraduate Medical Journal, 65, 729-734, (1989).

Oliveira, V., et al., "Renal denervation normalizes pressure and baroreceptor reflex in high renin hypertension in conscious rats." Hypertension, 19:II-17-II-21 (1992).

Ong, K. L., et al. "Prevalence, Awareness, Treatment, and Control of Hypertension Among United States Adults 1999-2004." Hypertension, 49: 69-75 (2007) (originally published online Dec. 11, 2006).

Ormiston, John et al., "First-in-human use of the OneShot™ renal denervation system from Covidien." EuroIntervention, vol. 8, 2013, 4 pages.

Ormiston, John et al., "Renal denervation for resistant hypertension using an irrigated radiofrequency balloon: 12-month results from the Renal Hypertension Ablation System (RHAS) trial." EuroIntervention, vol. 9, 2013, 5 pages.

Pedersen, Amanda, "TCT 2012: Renal denervation device makers play show and tell." Medical Device Daily, Oct. 26, 2012, 2 pages, <http://www.medicaldevicedaily.com/servlet/com.accumedia.web.Dispatcher?next=bioWorldHeadlines_article&forceid=80880>.

Peet, M., "Hypertension and its Surgical Treatment by bilateral supradiaphragmatic splanchnicectomy" Am J Surgery (1948) pp. 48-68.

Renal Denervation (RDN), Symplicity RDN System Common Q&A (2011), 4 pages, http://www.medtronic.com/rdn/mediakit/RDN%20FAQ.pdf.

Schauerte, P., et al. "Catheter ablation of cardiac autonomic nerves for prevention of vagal atrial fibrillation." Circulation, 102:2774-2780 (2000).

Schlaich, Markus et al., "Renal Denervation in Human Hypertension: Mechanisms, Current Findings, and Future Prospects." Curr Hypertens Rep, vol. 14, 2012, 7 pages.

Schmid, Axel et al. "Does Renal Artery Supply Indicate Treatment Success of Renal Denervation." Cardiovasc Intervent Radiol, vol. 36, 2013, 5 pages.

(56) References Cited

OTHER PUBLICATIONS

Schmieder, Roland E. et al., "Updated ESH position paper on interventional therapy of resistant hypertension." EuroIntervention, vol. 9, 2013, 9 pages.
Sievert, Horst, "Novelty Award EuroPCR 2010." Euro PCR, 2010, 15 pages.
Solis-Herruzo et al., "Effects of lumbar sympathetic block on kidney function in cirrhotic patients with hepatorenal syndrome," J. Hepatol. 5 (1987), pp. 167-173.
Stella, A., et al., "Effects of reversible renal deneravation on haemodynamic and excretory functions on the ipsilateral and contralateral kidney in the cat." Hypertension, 4:181-188 (1986).
Stouffer, G. A. et al., Journal of Molecular and Cellular Cardiology, vol. 62, 2013, 6 pages.
Swartz, J.F., et al., "Radiofrequency endocardial catheter ablation of accessory atrioventricular pathway atrial insertion sites." Circulation, 87: 487-499 (1993).
Uchida, F., et al., "Effect of radiofrequency catheter ablation on parasympathetic denervation: A comparison of three different ablation sites." PACE, 21:2517-2521 (1998).
Verloop, W. L. et al., "Renal denervation: a new treatment option in resistant arterial hypertension." Neth Heart J., Nov. 30, 2012, 6 pages, <http://www.ncbi.nlm.nih.gov/pmc/articles/PMC3547427/>.
Weinstock, M., et al., "Renal denervation prevents sodium rentention and hypertension in salt sensitive rabbits with genetic baroreflex impairment." Clinical Science, 90:287-293 (1996).
Wilcox, Josiah N., Scientific Basis Behind Renal Denervation for the Control of Hypertension, ICI 2012, Dec. 5-6, 2012. 38 pages.
Worthley, Stephen et al., "Safety and efficacy of a multi-electrode renal sympathetic denervation system in resistant hypertension: the EnligHTN I trial." European Heart Journal, vol. 34, 2013, 9 pages.
Worthley, Stephen, "The St. Jude Renal Denervation System Technology and Clinical Review." The University of Adelaide Australia, 2012, 24 pages.
Zuern, Christine S., "Impaired Cardiac Baroflex Sensitivity Predicts Response to Renal Sympathetic Denervation in Patients with Resistant Hypertension." Journal of the American College of Cardiology, 2013, doi: 10.1016/j.jacc.2013.07.046, 24 pages.
International Search Report and Written Opinion for International Application No. PCT/US2012/063411 dated Jun. 13, 2013, 13 pages.
U.S. Appl. No. 60/852,787, filed Oct. 18, 2006, 112 pages.
U.S. Appl. No. 60/976,733, filed Oct. 1, 2007, 49 pages.
U.S. Appl. No. 60/921,973, filed Apr. 4, 2007, 130 pages.
Gornick, C. et al., "Validation of a New Noncontact Catheter System for Electroanatomic Mapping of Left Ventricular Endocardium." Circulation, 1999; 99: 829-835.
Tanaka, K. et al., "A New Radiofrequency Thermal Balloon Catheter for Pulmonary Vein Isolation." Journal of the American College of Cardiology, vol. 38, No. 7, 2001, 8 pages.
Satake, S., "Usefulness of a New Radiofrequency Thermal Balloon Catheter for Pulmonary Vein Isolation: A New Device for Treatment of Atrial Fibrillation." Journal of Cardiovascular Electrophysiology, vol. 14, No. 6, Jun. 2003, 7pages.
Miller, Reed, "Finding a Future for Renal Denervation With Better Controlled Trials." Pharma & Medtech Business Intelligence, Article # 01141006003, Oct. 6, 2014, 4 pages.
Papademetriou, Vasilios, "Renal Denervation and Symplicity HTN-3: "Dubium Sapientiae Initium" (Doubt Is the Beginning of Wisdom)", Circulation Research, 2014; 115: 211-214.
Papademetriou, Vasilios et al., "Renal Nerve Ablation for Resistant Hypertension: How Did We Get Here, Present Status, and Future Directions." Circulation. 2014; 129: 1440-1450.
Papademetriou, Vasilios et al., "Catheter-Based Renal Denervation for Resistant Hypertension: 12-Month Results of the EnligHTN I First-in-Human Study Using a Multielectrode Ablation System." Hypertension. 2014; 64: 565-572.
Doumas, Michael et al., "Renal Nerve Ablation for Resistant Hypertension: The Dust Has Not Yet Settled." The Journal of Clinical Hypertension. 2014; vol. 16, No. 6, 2 pages.
Messerli, Franz H. et al. "Renal Denervation for Resistant Hypertension: Dead or Alive?" Healio: Cardiology today's Intervention, May/Jun. 2014, 2 pages.
Dodge, et al., "Lumen Diameter of Normal Human Coronary Arteries Influence of Age, Sex, Anatomic Variation, and Left Ventricular Hypertrophy or Dilation", Circulation, 1992, vol. 86 (1), pp. 232-246.
Opposition to European Patent No. 2465470, Granted Oct. 28, 2015, Date of Opposition Jul. 27, 2016, 34 pp.
U.S. Appl. No. 11/363,867, filed Feb. 27, 2006, 70 pp.
U.S. Appl. No. 60/813,589, filed Dec. 29, 2005, 62 pp.
Ureter, https://en.wikigedia.org/wiki/Ureter, Jun. 2016, 6 pp.

\* cited by examiner

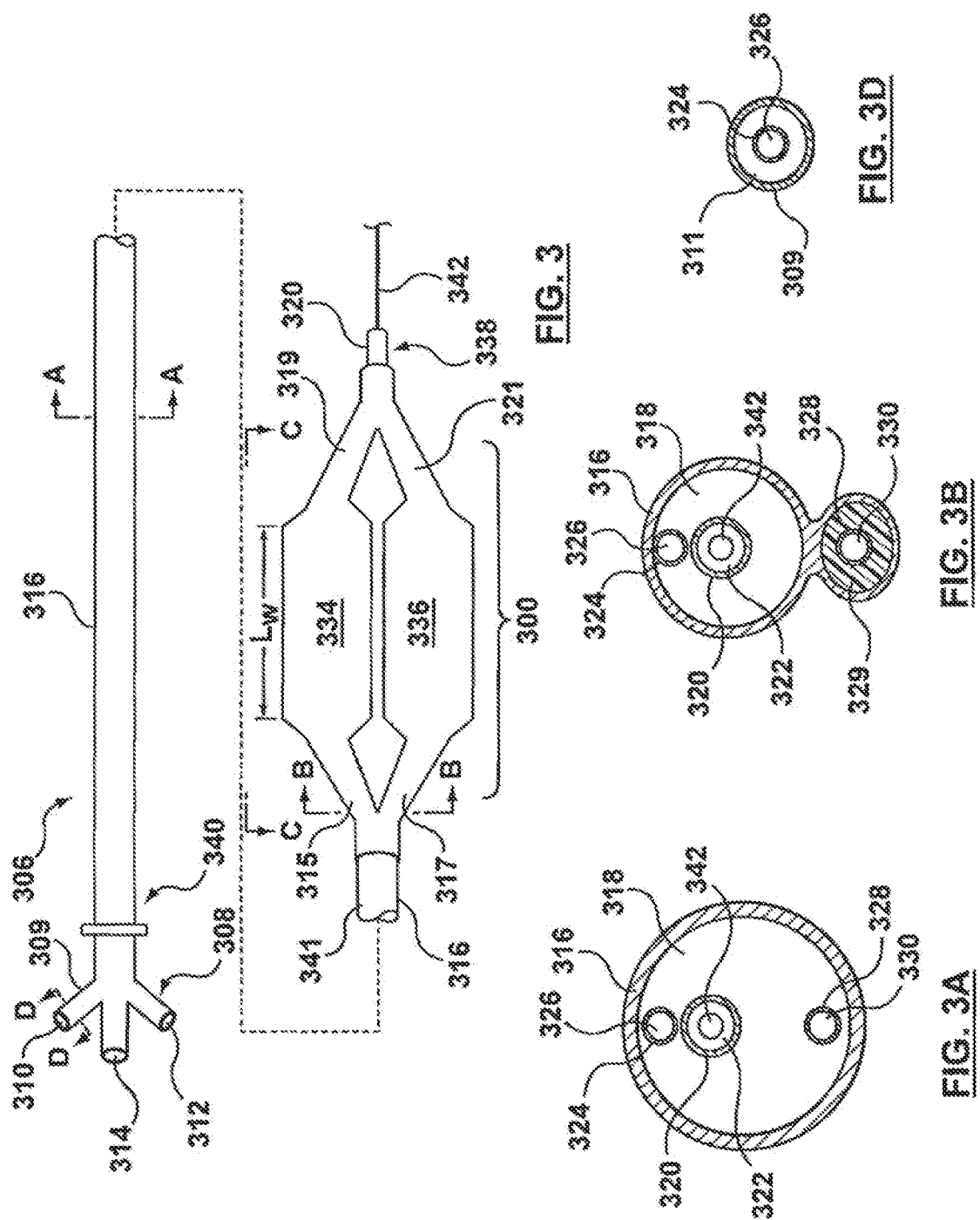

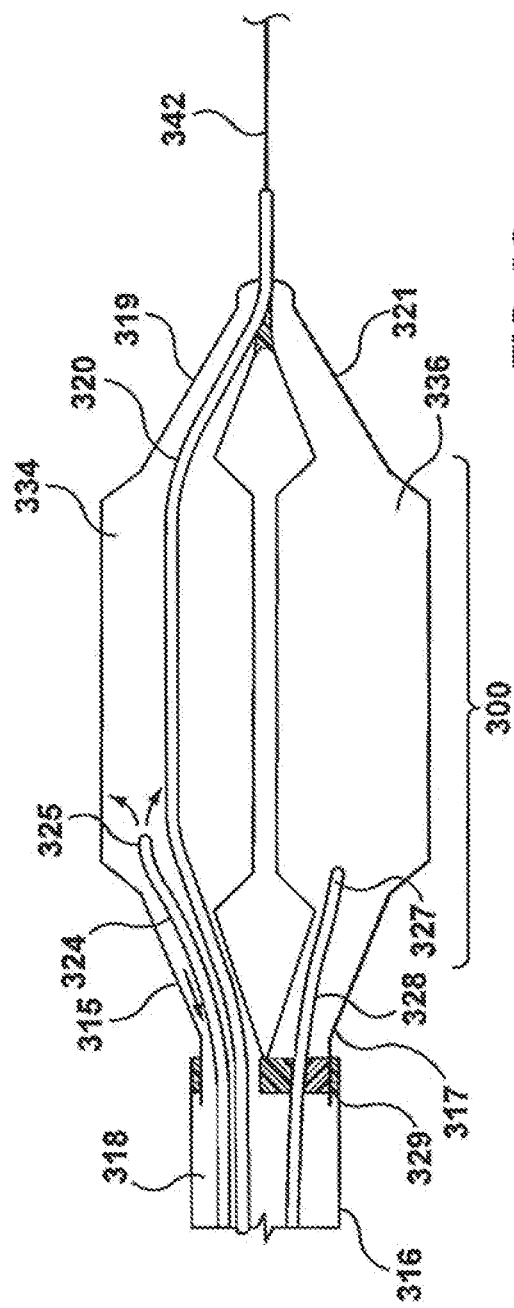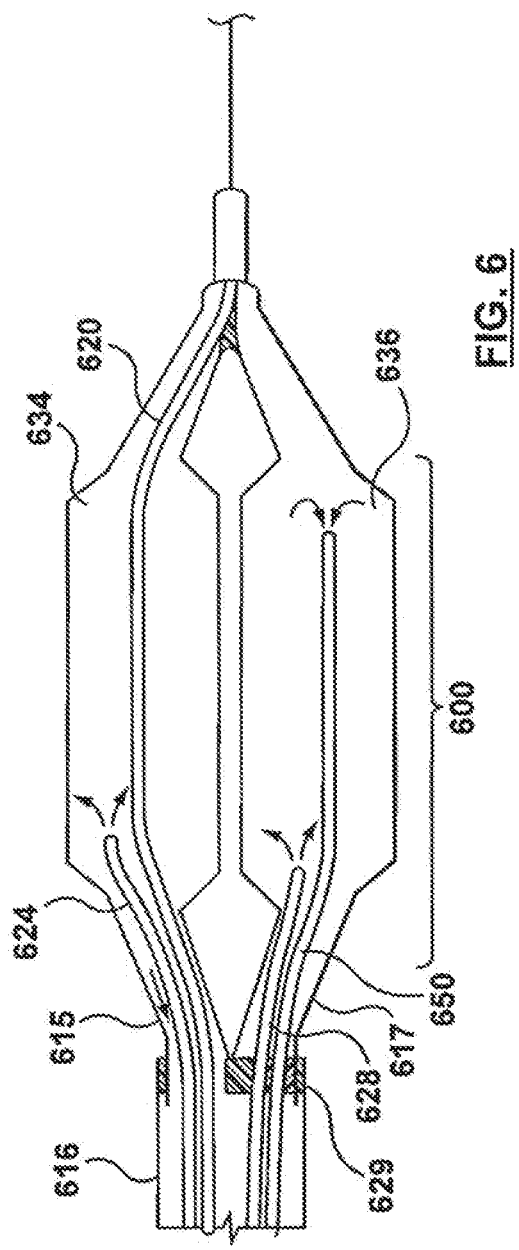

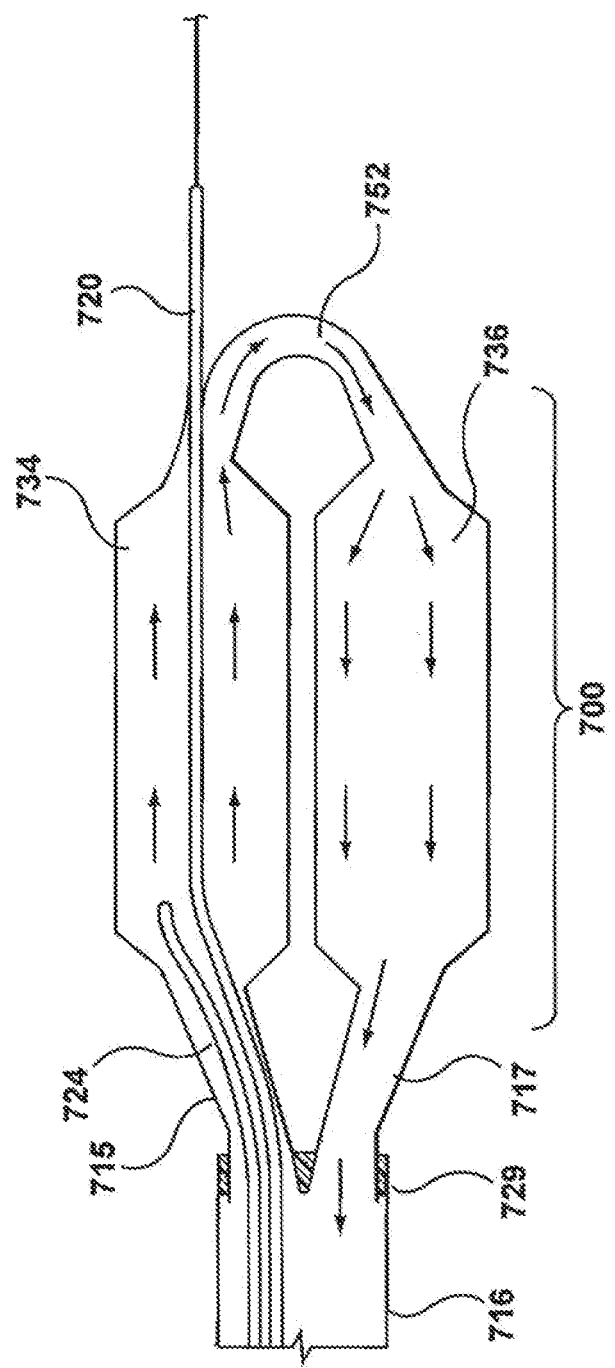

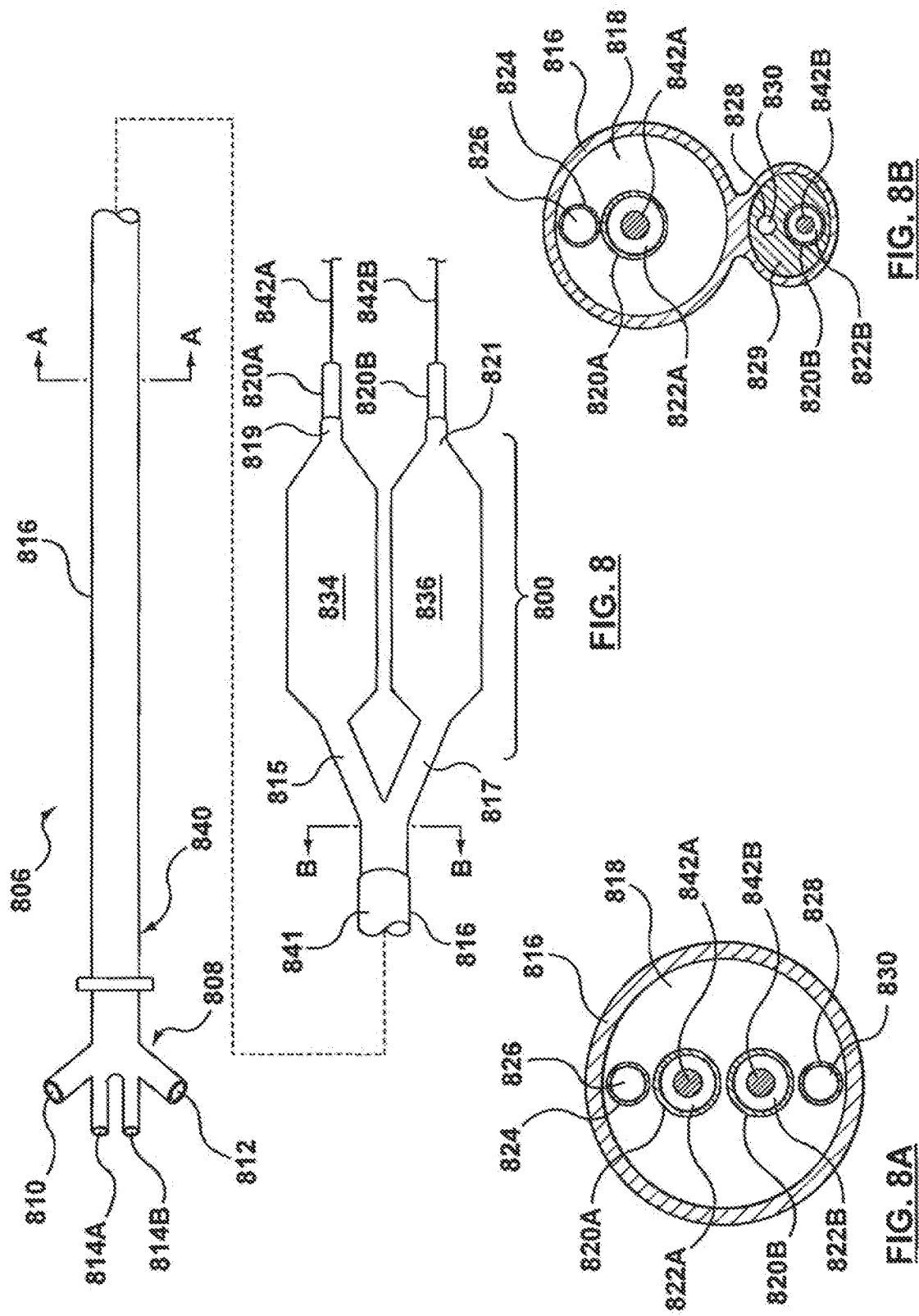

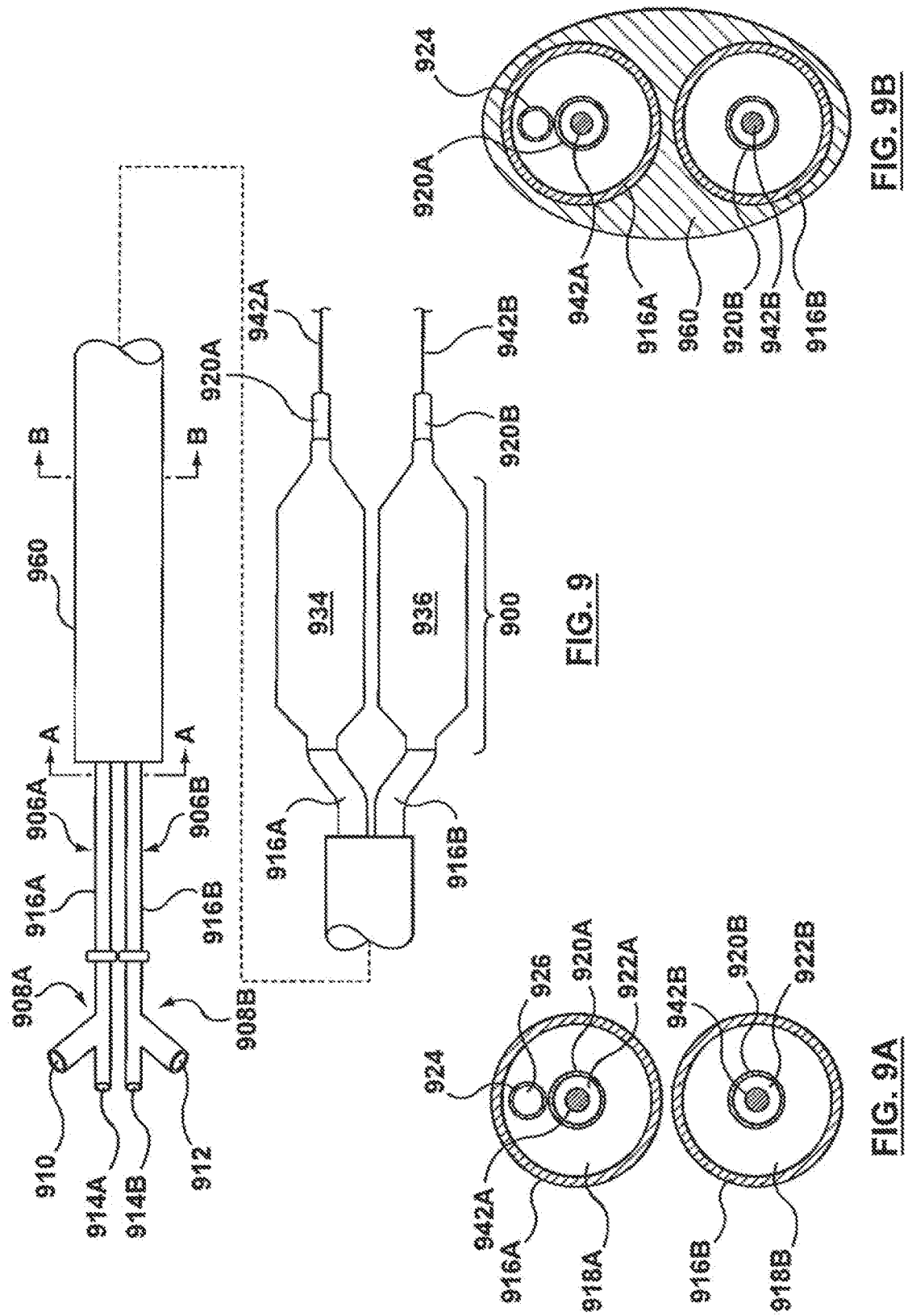

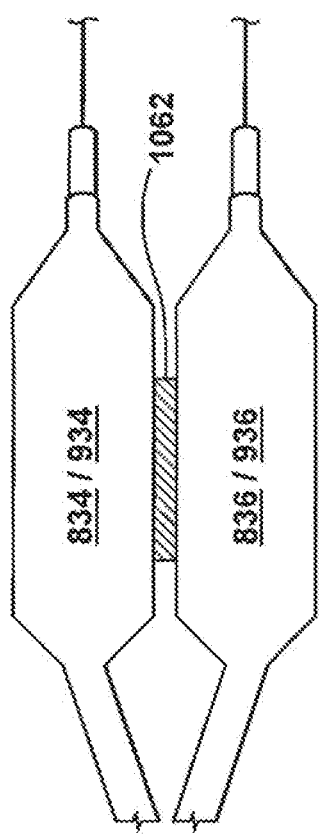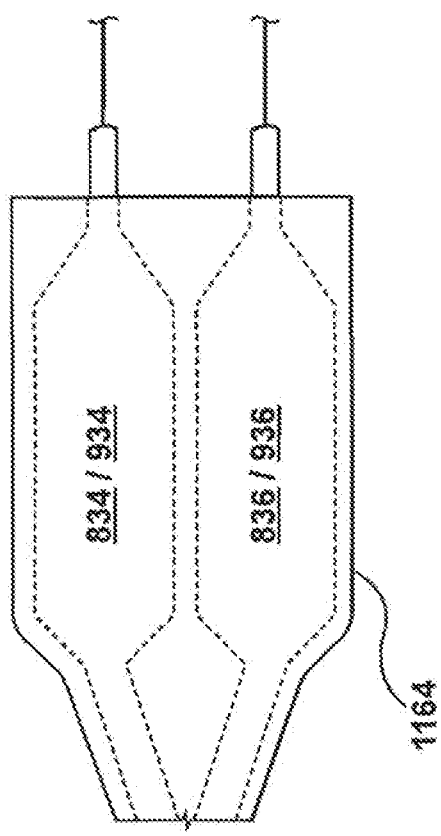

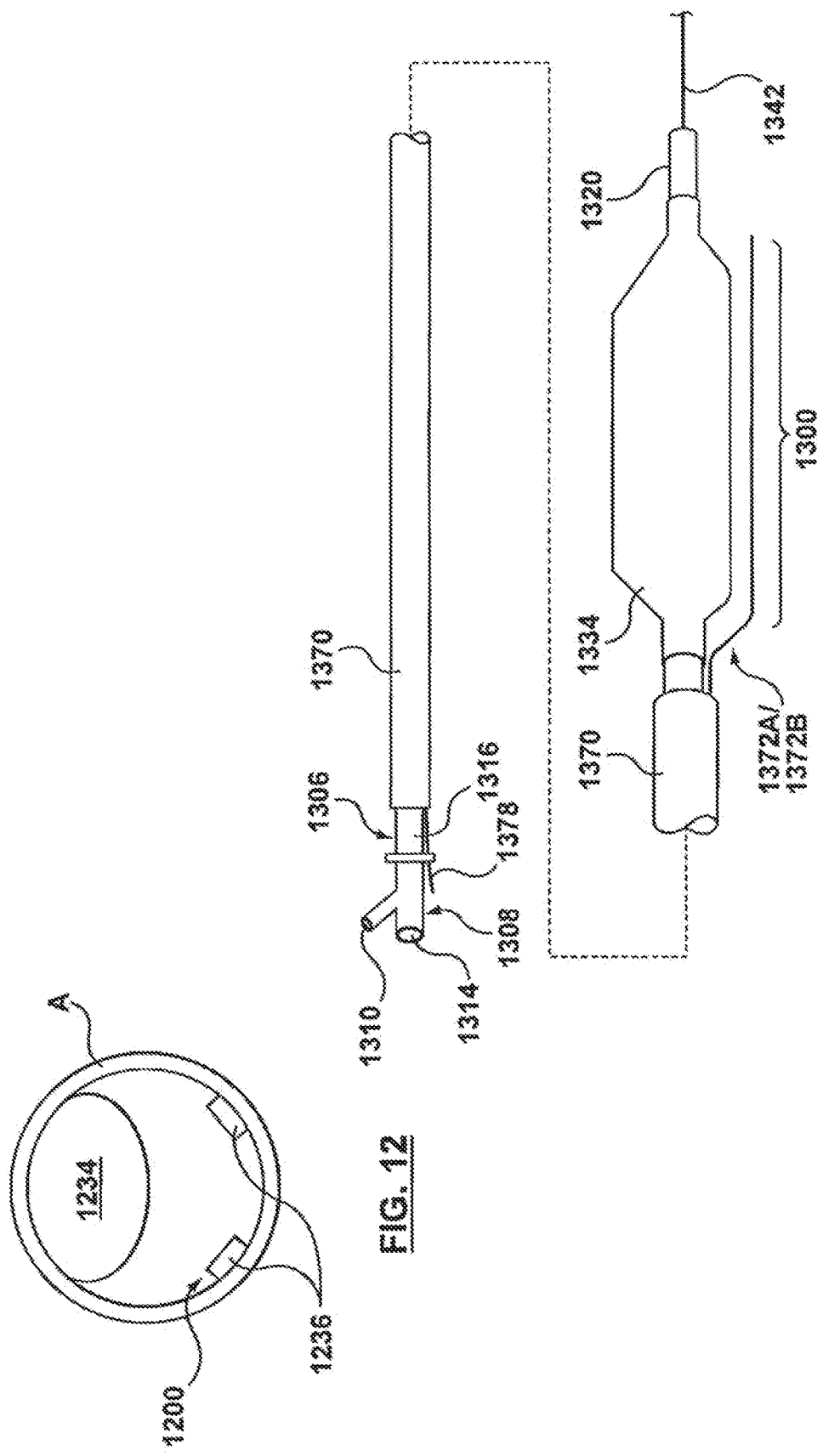

APPARATUS AND METHODS RELATED TO CONSTRAINED DEPLOYMENT OF CRYOGENIC BALLOONS FOR LIMITED CRYOGENIC ABLATION OF VESSEL WALLS

CROSS REFERENCE TO RELATED APPLICATION

This disclosure claims the benefit of U.S. Provisional Application No. 61/572,288, filed Apr. 25, 2011, which is incorporated herein by reference in its entirety.

TECHNICAL FIELD

The present technology relates in general to cryotherapy, and in particular, to apparatus and methods for cryogenically cooling a targeted area of an inner surface of an anatomical vessel or other tissue.

BACKGROUND

Cryotherapy can be a useful treatment modality in a wide range of catheter-based interventional procedures. For example, cryotherapeutic cooling can be used to modulate nerves or affect other tissue proximate anatomical vessels (e.g., blood vessels, other body lumens, or other areas in the body). This can reduce undesirable neural activity to achieve therapeutic benefits. Catheter-based neuromodulation utilizing cryotherapy can be used, for example, to modulate nerves and thereby reduce pain, local sympathetic activity, systemic sympathetic activity, associated pathologies, and other conditions. Furthermore, cryotherapy can be used, for example, for ablating tumors and treating stenosis. In some cryotherapeutic procedures, it can be useful to deliver cryotherapy via a balloon that can be expanded within an anatomical vessel. Such balloons can be operatively connected to extracorporeal support components (e.g., refrigerant supplies). As the applicability of cryotherapy for surgical intervention continues to expand, there is a need for innovation in the associated devices, systems, and methods. Such innovation has the potential to further expand the role of cryotherapy as a tool for improving the health of patients.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present technology.

FIG. 3 is a side view of a dual balloon catheter having an ablation assembly at the distal end thereof, wherein the dual balloon catheter includes a single guidewire lumen.

FIG. 3A is a cross-sectional view taken along line A-A of FIG. 3.

FIG. 3B is a cross-sectional view taken along line B-B of FIG. 3.

FIG. 3C is a sectional view taken along line C-C of FIG. 3.

FIG. 3D is a cross-sectional view taken along line D-D of FIG. 3.

FIG. 6 is a sectional view taken along line C-C of FIG. 3 according to another embodiment hereof, wherein the catheter further includes an inflation fluid return shaft for circulating warm inflation fluid within the constraining element of the ablation assembly.

FIG. 7 is a sectional view taken along line C-C of FIG. 3 according to another embodiment hereof, wherein the catheter utilizes exhaust of the cryotherapy to inflate the constraining element of the ablation assembly.

FIG. 8 is a side view of a dual balloon catheter having an ablation assembly at the distal end thereof according to another embodiment hereof, wherein the dual balloon catheter includes two separate guidewire lumens.

FIG. 8A is a cross-sectional view taken along line A-A of FIG. 8.

FIG. 8B is a cross-sectional view taken along line B-B of FIG. 8.

FIG. 9 is a side view of a catheter assembly having an ablation assembly at the distal end thereof according to another embodiment hereof, wherein the catheter assembly includes two balloon catheters.

FIG. 9A is a cross-sectional view taken along line A-A of FIG. 9.

FIG. 9B is a cross-sectional view taken along line B-B of FIG. 9.

FIG. 10 is a side view of the distal portion of FIG. 8 or FIG. 9, wherein the two balloons are joined via an adhesive.

FIG. 11 is a side view of the distal portion of FIG. 8 or FIG. 9, wherein the two balloons are located within an outer sheath.

FIG. 12 is a partially schematic cross-sectional view of an artery having an ablation assembly according to another embodiment deployed therein, wherein the ablation assembly includes a cryoballoon and a constraining element that positions the cryoballoon within the artery.

FIG. 13 is a side view of a catheter having a ablation assembly at the distal end thereof according to another embodiment hereof, wherein the ablation assembly includes a cryoballoon and a pair of self-expanding prongs for deflecting at least a portion of the cryoballoon away from the vessel wall.

DETAILED DESCRIPTION

Figure 1:
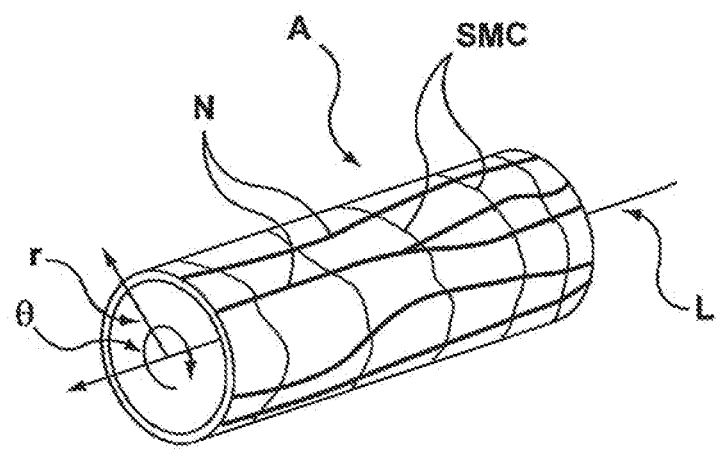
FIG. 1 is a partially schematic isometric detail view of a common location of neural fibers proximate an artery.

Specific embodiments of the present technology are now described with reference to the figures, wherein like reference numbers indicate identical or functionally similar elements. The terms "distal" and "proximal" are used in the following description with respect to a position or direction relative to the treating clinician. "Distal" and "distally" refer to positions distant from or in a direction away from the clinician. "Proximal" and "proximally" refer to positions near or in a direction toward the clinician.

The following detailed description discloses specific examples of the technology, but it is not intended to limit the present technology or the application and uses of the present technology. For example, although the description discloses the present technology in the context of treatment of blood vessels, such as renal arteries, the present technology may also be used in any other body passageways or tissues where it is deemed useful. Furthermore, there is no intention to be bound by any expressed or implied theory presented herein.

In recent years, ablation of tissue has been used to modulate neural fibers that contribute to renal function. Ablation may be accomplished in various ways, including delivery of radio frequency (RF) energy, other suitable heating energies, or cryotherapy. Modulation of renal nerves is expected to be useful in treating a variety of renal, cardio-renal, and other diseases including heart failure, renal disease, renal failure, hypertension, contrast nephropathy, arrhythmia, and myocardial infarction. Furthermore, renal neuromodulation is expected to reduce renal sympathetic nervous activity, which can increase removal of water and sodium from the body and return renin secretion to more normal levels. Normalized renin secretion can cause blood vessels supplying the kidneys to assume a steady state level of dilation and constriction corresponding to adequate renal blood flow.

In neuromodulation procedures, it may be desirable to perform circumferential ablation that extends continuously about a full 360° of the circumference of an anatomical vessel to positively affect a medical condition. For example, in the treatment of atrial fibrillation or other arrhythmia, a circumferential treatment may be achieved by forming a circumferential lesion that is continuous completely about a normal cross-section of the pulmonary vein to disrupt aberrant electrical signals. In the treatment of heart failure, a circumferential treatment may be achieved by forming a similar continuous circumferential lesion that is continuous completely about a normal cross-section of a renal artery to reduce renal sympathetic neural activity. However, in some cases, it can be desirable to reduce structural changes to a blood vessel and avoid a circumferential ablation lesion along a single radial plane or cross-section of a blood vessel. Partial circumferential, non-continuous, or helical ablation are expected to be effective to treat a variety of renal, cardio-renal, and other diseases including those listed herein with less structural changes to vessels than fully circumferential, continuous, and non-helical ablation.

FIG. 1 illustrates a common anatomical arrangement of neural structures relative to body lumens or vascular structures, typically arteries. Neural fibers N generally may extend longitudinally along a lengthwise or longitudinal dimension L of an artery A about a relatively small range of positions along the radial dimension r, often within the adventitia of the artery. The artery A has smooth muscle cells SMC that surround the arterial circumference and generally spiral around the angular dimension e of the artery, also within a relatively small range of positions along the radial dimension r. The smooth muscle cells SMC of the artery A accordingly have a lengthwise or longer dimension generally extending transverse (i.e., non-parallel) to the lengthwise dimension of the blood vessel.

Neuromodulation may be accomplished by ablating tissue through the use of an ablation catheter. As utilized herein, the term ablation includes the creation of scar tissue or a lesion that blocks or disrupts nerve conduction. In embodiments hereof, freezing temperatures or cryotherapy can be utilized to thermally damage or ablate target tissue of an artery to achieve neuromodulation of the target neural fibers. As compared to ablation lesions formed via radiofrequency energy, cryotherapy typically utilizes much less power to achieve neuromodulation. As described above, partial circumferential ablation (i.e., ablation extending around less than 360° of a vessel wall), non-continuous ablation, or helical ablation may be desirable in some cases. In order to form partial circumferential, non-continuous, or helical ablation lesions, cryotherapy can be focused on or constrained to target regions of tissue to be treated and non-target tissue can be protected from ablation (e.g., by deflecting or offsetting a portion of a cryoballoon away from the non-target tissue using the various apparatuses and methods described herein).

Figures 2, 2A:
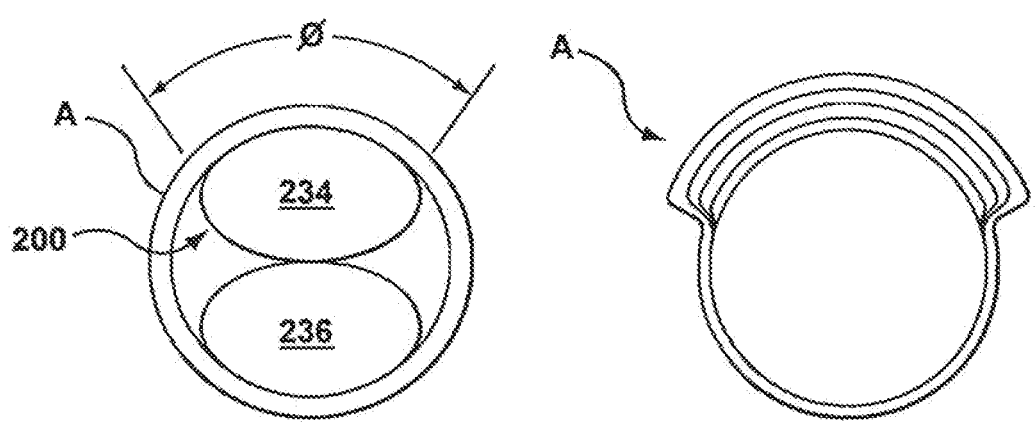
FIG. 2 is a partially schematic cross-sectional view of an artery having an ablation assembly deployed therein, wherein the ablation assembly includes a cryoballoon and a constraining element that can position the cryoballoon within the artery.
FIG. 2A is a partially schematic illustration of an ablation therapy pattern within an artery following treatment with the ablation assembly of FIG. 2.

Turning now to FIG. 2, an ablation assembly 200 is shown deployed within an artery A. Ablation assembly 200 includes a cryoballoon 234 for neuromodulation of the target neural fibers and a constraining element 236 that offsets cryoballoon 234 within the artery A. As will be explained in more detail below, in various embodiments hereof, constraining element 236 can be a radially-expandable component that expands into contact with at least one of a portion of the exterior surface of cryoballoon 234 and a portion of the vessel wall to prevent cryoballoon 234 from contacting and ablating non-targeted tissue of the vessel wall. Stated another way, constraining element 236 can deflect away or block a portion of the surface of cryoballoon 234 from contacting non-targeted tissue of the vessel wall such that cryoballoon 234 will contact a section of the vessel wall that corresponds to less than a full circumference of the vessel wall and thereby perform a partial circumferential ablation of a longitudinal section of the vessel wall. As shown in FIG. 2, in one embodiment constraining element 236 is a second balloon which pushes away or blocks a portion of cryoballoon 234 from contacting non-target tissue of the vessel wall. Partial circumferential, non-continuous, or helical ablation of artery A can alter the sympathetic nervous system and can be effective for treating a variety of renal, cardiorenal, and other diseases including but not limited to hypertension, heart failure, renal disease, renal failure, contrast nephropathy, arrhythmia, and myocardial infarction.

A resulting cross-section of the ablation pattern or footprint of ablation assembly 200 is shown in FIG. 2A. The area of contact between the exterior surface of cryoballoon 234 and the vessel wall may be considered a nominal treatment area, which is equal to or slightly smaller than the ablation pattern resulting from ablation assembly 200 because the ablation therapy may extend slightly beyond the borders of the nominal treatment area. For example, the nominal treatment area of ablation assembly 200 may extend around between 45° and 225° of the vessel wall circumference while the resulting ablation pattern of ablation assembly 200 may extend around between 10° and 340° of the vessel wall circumference. However, for purposes of the present disclosure, the nominal treatment area and the ablation pattern are considered to be approximately equal. The nominal treatment area/ablation pattern depends upon both a contact surface arc Ø of the ablation assembly and a working length LW of cryoballoon 234 (see FIG. 3 and FIG. 4 for examples of working lengths LW of a cryoballoon). More particularly, the nominal treatment area/ablation pattern may be calculated by multiplying the length of the contact surface arc LØ by the working length LW of cryoballoon 234. The length of contact surface arc may be roughly calculated by the equation LØ=R((2ˆØ)/360), wherein R is the radius and Ø is the contact surface arc. As previously mentioned, in embodiments hereof, constraining element 236 can deflect or offset cryoballoon 234 from contacting non-targeted tissue such that the contact surface arc Ø of cryoballoon 234 is constrained or limited to between 45° and 225° of the vessel wall.

The side view of FIG. 3 as well as the cross-sectional views FIG. 3A and FIG. 3B illustrate a first embodiment having an ablation assembly of a cryoballoon and a second balloon for deflecting the cryoballoon away from non-target tissue. More particularly, a dual balloon catheter 306 includes an ablation assembly 300 at a distal end thereof. Ablation assembly 300 includes a first cryoballoon 334 and a second constraining balloon 336 that are disposed substantially in parallel, i.e., side-by-side, such that at least a portion of the exterior or outer surfaces of cryoballoon 334 and constraining balloon 336 are in contact in their expanded configurations. Balloons 334, 336 are shown in their expanded or inflated configurations in FIG. 3. For illustrative purposes only, balloons 334, 336 as well as other dual balloon configurations described herein are shown in the figures as slightly separated from each other in their expanded configurations. However, it will be understood by those of ordinary skill in the art that at least a portion of the outer surfaces of balloons 334, 336 and all dual balloon configurations described herein typically press against and contact each other when deployed in a vessel and constrained by the vessel wall as shown in FIG. 2. Balloons 334, 336 and other balloons disclosed herein can be made using a variety of suitable manufacturing processes. For example, the balloons 334, 336 can be made using extrusion, molding, or a combination thereof. Furthermore, the balloons 334, 336 can be formed separately or together. In some embodiments, when the balloons 334, 336 are made of different materials (e.g., materials with different compliances), the different materials can be processed simultaneously (e.g., by coextrusion).

In the embodiment shown in FIGS. 3, 3A, and 3B, dual-balloon catheter 306 has an over-the-wire (OTW) catheter configuration with an inner guidewire shaft 320 that defines a guidewire lumen 322 extending substantially the entire length of the catheter for accommodating a guidewire 342. Catheter 306 includes a tubular component or outer shaft 316 which defines a lumen 318. Outer shaft 316 has a proximal end 340 that extends out of the patient and is coupled to a hub 308 and a distal end 341 coupled to proximal necks 315, 317 of balloons 334, 336, respectively. Distal necks 319, 321 of balloons 334, 336, respectively, are coupled to guidewire shaft 320. Proximal necks 315, 317 and distal necks 319, 321 of balloons 334, 336 may be joined to outer catheter shaft 316 and guidewire shaft 320, respectively, in any conventional manner known to one of skill in the art of balloon catheter construction, such as by laser welding, adhesives, heat fusing, or ultrasonic welding. In one embodiment, balloons 334, 336 are formed as two separate components, the ends of proximal necks 315, 317 are joined, and the ends of distal necks 319, 321 are joined. Other suitable manufacturing methods and configurations are also possible.

Guidewire shaft 320 has a proximal end (not shown) coupled to hub 308 and a distal end 338 terminating distally of balloons 334, 336. A proximal guidewire port 314 of hub 308 is in fluid communication with guidewire lumen 322 of guidewire shaft 320. Distal end 338 of guidewire shaft 320 may be coupled to a tapered distal catheter tip (not shown) that defines a distal guidewire port of the catheter. As shown in the sectional view of FIG. 3C, in one embodiment guidewire shaft 320 extends through cryoballoon 334. However, it will be apparent to those of ordinary skill in the art that catheter 306 may be modified such that guidewire shaft 320 alternatively extends through constraining balloon 336. A single guidewire lumen can simplify catheter construction and luer design, as well as reduce the outer diameter of catheter 306. In addition, since distal necks 319, 321 of balloons 334, 336, respectively, are both coupled to guidewire shaft 320, the single guidewire lumen catheter construction can help to maintain balloons 334, 336 in position relative to each other during deployment.

Catheter 306 further includes a cryo-supply tube 324 extending through outer shaft 316. The cryo-supply tube 324 defines an inflation lumen 326 (see FIGS. 3A-3B) and has a proximal end (not shown) coupled to hub 308 and a distal end 325 (see FIG. 3C) that terminates within cryoballoon 334. A cryo-inflation port 310 of hub 308 is in fluid communication with inflation lumen 326 of cryo-supply tube 324. Cryo-supply tube 324 receives and delivers a cryogenic agent such as $N_2O$ liquid into cryoballoon 334 at a high pressure, e.g., 800 psi, such that there is a pressure drop when the cryogenic agent enters the interior of cryoballoon 334 and expands to a gas. The cryogenic agent may be any liquid having a boiling point colder than approximately −10° C. at atmospheric pressure such as but not limited to $N_2O$ liquid or $CO_2$ liquid. During the phase change of the cryogenic agent, a cooling effect takes place because expansion of compressed gas is an endothermic process that absorbs energy in the form of heat and thus results in cooling of the surroundings. Accordingly, as the cryogenic agent expands into gas, cryoballoon 334 is expanded or inflated and the exterior surface of the cryoballoon is cooled to cryogenic temperatures operable to ablate or thermally damage tissue. The temperature of cryoballoon 334 may be between approximately −5° C. and −120° C., which can result in modulation of neural fibers located adjacent to cryoballoon 334. As would be understood by one of ordinary skill in the art of balloon catheter design, hub 308 can provide a luer hub or other type of fitting that may be connected to a source of inflation fluid and may be of another construction or configuration without departing from the scope of the present technology.

Catheter 306 also includes a constraining-supply tube 328 extending through outer shaft 316. The constraining-supply tube 328 defines an inflation lumen 330 and has a proximal end (not shown) coupled to hub 308 and a distal end 327 (see FIG. 3C) that terminates within constraining balloon 336. An inflation port 312 of hub 308 is in fluid communication with inflation lumen 330 of constraining-supply tube 328. Constraining-supply tube 328 receives and delivers an inflation medium such as saline or air into constraining balloon 336. Once inflated, constraining balloon 336 prevents a portion of the outer surface of cryoballoon 334 from coming into contact with non-targeted tissue of the vessel wall. More particularly, constraining balloon 336 expands to push away or deflect a portion of the outer surface of cryoballoon 334 from contacting non-targeted tissue of the vessel wall. Non-targeted tissue may thereby be prevented from contact with or protected from the cryogenically-cooled exterior surface of cryoballoon 334, and therefore constraining balloon 336 may prevent a complete continuous circumferential ablation of the vessel wall.

In addition to offsetting cryoballoon 334, in one embodiment constraining balloon 336 also serves to moderate the temperature of the cryotherapy. For example, when $N_2O$ liquid is utilized as the cryogenic agent, the phase change of the cryogenic agent to gas may result in a cryoballoon temperature in the range of −70° C. to −80° C. However, neuromodulation may be accomplished at temperatures between −10° C. and −40° C., and these higher temperatures may be preferred in certain applications to minimize unnecessary damage to the vessel. Since cryoballoon 334 and constraining balloon 336 deploy and expand against each other within the artery during treatment, heat transfer can occur therebetween. Accordingly, an inflation fluid such as water or saline within constraining balloon 336 may freeze. However, the decrease in resulting temperature will not be to such an extent that thermal injury will occur. Thermal injury or neuromodulation generally occurs at temperatures below −5° C., while a frozen constraining balloon 336 can have a temperature at or above −3° C. Notably, the heat transfer from constraining balloon 336 to cryoballoon 334 may be beneficial to increase the temperature of the cryogenically-cooled balloon outer surface from, e.g., −80° C., to a preferred temperature for ablation, e.g., between −10° C. and −40° C. Thus, the heat transfer between the balloons may help to moderate the temperatures of the cryotherapy.

In one embodiment, balloons 334, 336 are inflated simultaneously. In another embodiment, constraining balloon 336 and cryoballoon 334 are inflated sequentially. Constraining balloon 336 may be inflated prior to cryoballoon 334 in order to properly position and/or orient the balloons within the artery.

The multiple catheter shafts of catheter 306, e.g., outer shaft 316, guidewire shaft 320, cryo-supply tube 324, and constraining-supply tube 328, may be formed of a polymeric material, non-exhaustive examples of which include polyethylene, polyethylene block amide copolymer (PEBA), polyamide, and/or combinations thereof, which can be laminated, blended, co-extruded, or processed according to another suitable method. In an embodiment, guidewire shaft 320 may be a flexible tube of a polymeric material, such as, e.g., polyethylene tubing. Optionally, outer shaft 316 or some portion thereof may be formed as a composite having a reinforcement material incorporated within a polymeric body in order to enhance strength and/or flexibility. Suitable reinforcement layers can include braiding, wire mesh layers, embedded axial wires, embedded helical or circumferential wires, and the like. In one embodiment, for example, at least a proximal portion of outer shaft 316 may be formed from a reinforced polymeric tube. In addition, although catheter 306 is described herein as being constructed with various shafts extending therethrough for forming lumens of the catheter, it will be understood by those of ordinary skill in the art that other types of catheter construction are also possible, such as, without limitation thereto, a catheter shaft formed by multi-lumen profile extrusion. In another embodiment, catheter 306 may be modified to be of a rapid exchange (RX) catheter configuration without departing from the scope of the present technology such that guidewire shaft 320 extends within only the distal portion of catheter 306.

Figure 4:
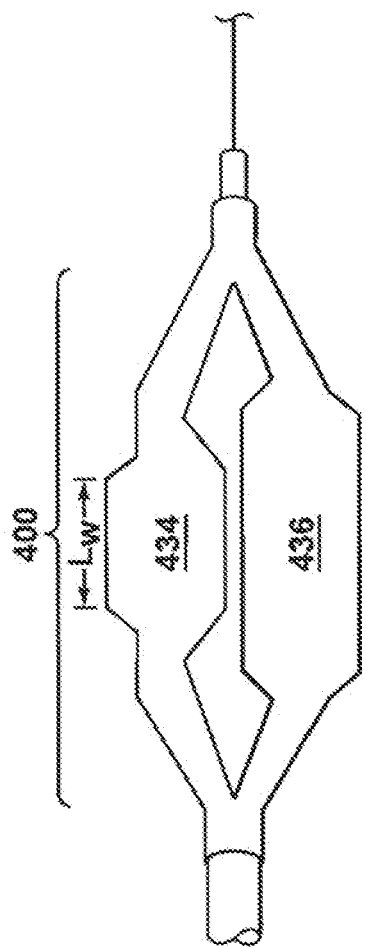
FIG. 4 is a side view of a dual-balloon configuration of the ablation assembly of FIG. 3 according to another embodiment hereof.

Although shown as having approximately equal expanded profiles, the cryoballoon and the constraining balloon may have different, unequal dimensions depending on the desired ablation therapy pattern. For example, as shown in the embodiment of FIG. 4, an ablation assembly 400 can include a cryoballoon 434 which is shorter in length than a constraining balloon 436. As described above in more detail, the nominal treatment area/ablation pattern can depend upon the working length LW of the cryoballoon. Accordingly, in general, shorter cryoballoon 434 contacts less tissue in the longitudinal direction of the vessel wall than cryoballoon 334 and thus results in a smaller nominal treatment area than cryoballoon 334. In addition, shorter cryoballoon 434 may require a longer treatment time in order to achieve neuromodulation as opposed to longer cryoballoons which may cause deeper and/or longer ablation patterns.

In another example, the cryoballoon and the constraining balloon may have different expanded outer diameters. In the embodiment of FIG. 5, an ablation assembly 500 can include a cryoballoon 534 having a smaller expanded outer diameter than a constraining balloon 536. To achieve different expanded outer diameters, the balloons may be formed of materials having different compliances. Dilatation balloons may be classified, for example, as being compliant, non-compliant, or semi-compliant. Compliant balloons can be characterized by their ability to radially expand beyond their nominal diameters in response to increasing inflation pressure. Such balloons can be said to follow a stress-strain curve obtained by plotting balloon diameter versus inflation pressure. Noncompliant balloons can be characterized by nearly flat stress-strain curves illustrating that the balloon diameters expand relatively little over the range of usable inflation pressures. To achieve a smaller expanded outer diameter, cryoballoon 534 may be semi-compliant or non-compliant. In some embodiments, cryoballoon 534 can be 10% or less compliant and formed from PEBAX polymer or nylon. Constraining balloon 536 may be, for example, between 50% and 100% compliant and formed from polyurethane or silicone. Percentage compliance can correspond to the percentage of expansion that occurs between the cryoballoon 534 at an operating pressure and the cryoballoon 534 at a rated pressure (e.g., a burst pressure or a maximum inflation pressure). The recited values for percentage compliance can also apply to dispensability, which can be calculated as follows:

$$\text{Distensibility} = \left[ \frac{\text{Diameter of Balloon at Selected Pressure}}{\text{Nominal Diameter of Balloon}} - 1 \right] \times 100\%$$

The selected pressure can be an arbitrary, relatively high pressure (e.g., 10 bar). Suitable materials that may be utilized to achieve a desired amount of compliance for the balloons include but are not limited to polymers such as polyethylene, polyethylene block amide copolymer (PEBA), PEBAX polymer, nylon, silicone, polyethylene terephthalate (PET), polyamide, polyurethane, and copolymers or blends thereof.

Figure 5A:
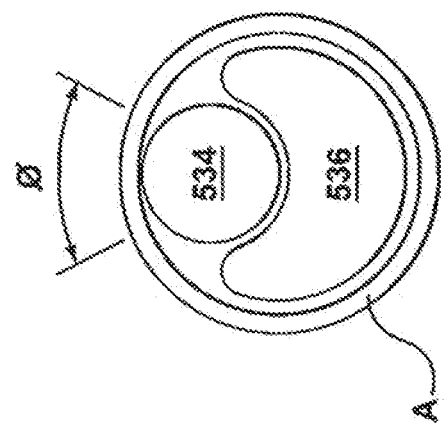
FIG. 5A is a partially schematic cross-sectional view of an artery having the ablation assembly of FIG. 5 deployed therein.
Figure 5:
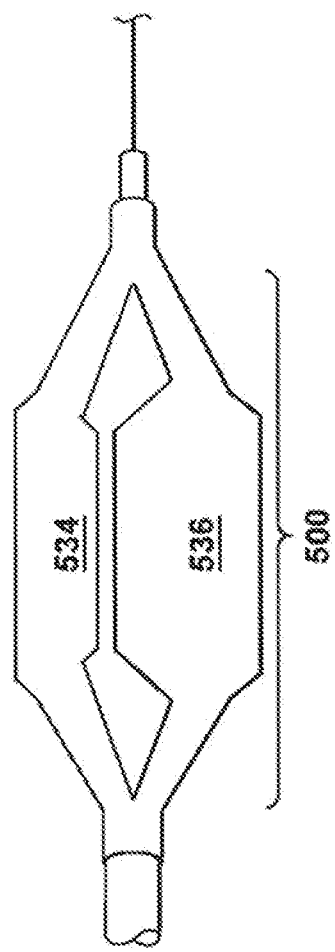
FIG. 5 is a side view of a dual-balloon configuration of the ablation assembly of FIG. 3 according to another embodiment hereof.

As shown in FIG. 5A, during deployment within artery A, constraining balloon 536 of a greater expanded outer diameter can essentially wrap or curl around smaller cryoballoon 534, thereby preventing ablation of a greater circumferential portion of the vessel wall. Stated another way, the constraining balloon 536 can curl around smaller cryoballoon 534 and effectively reduce the contact surface arc Ø of the nominal treatment area/ablation pattern. The expanded diameter of cryoballoon 534 determines the contact surface arc Ø and therefore determines the amount of circumferential tissue cryogenically ablated. In general, smaller cryoballoon 534 contacts less tissue around the circumference of the vessel wall and thus results in a smaller nominal treatment area/ablation pattern than cryoballoon 334. In the embodiment depicted in FIG. 5A, contact surface arc Ø is less than half of the circumference of the vessel wall or between 45° and 180° of the vessel wall. In another embodiment (not shown), if it is desired to ablate more than half of the circumference of the vessel wall, the cryogenic balloon can have a contact surface arc Ø between 180° and 225° of the vessel wall and may be constructed to have a greater expanded outer diameter than the constraining balloon such that the larger cryoballoon wraps around the smaller constraining balloon during deployment.

Referring back to FIG. 3 as well as the sectional views of FIG. 3B, FIG. 3C, and FIG. 3D, another feature of catheter 306 is described. In the embodiment of FIG. 3, constraining balloon 336 can be inflated and held at a constant pressure or at a constant outer diameter depending on the design thereof and an interior of constraining balloon 336 is not in fluid communication with lumen 318 of outer shaft 316. As shown in the cross-sectional view of FIG. 3B which is taken at the location of a proximal bond 329 between balloon necks 315, 317 of balloons 334, 336, respectively, proximal bond 329 surrounds and seals off constraining-supply tube 328 from lumen 318 of outer shaft 316. At the site of proximal bond 329, outer shaft 316 transforms from the annular configuration of FIG. 3A to a generally figure "8" configuration which resembles balloon necks 315, 317. In one embodiment, proximal balloon neck 315 of cryoballoon 334 has a larger diameter and corresponding lumen than proximal balloon neck 317 of constraining balloon 336 in order to allow expanded cryogenic gas or exhaust to exit from the interior of cryoballoon 334 as will be explained in more detail herein. Although proximal balloon neck 315 may be larger than proximal balloon neck 317, the expanded outer diameters of balloons 334, 336 may be the same or different as described above. Proximal bond 329 may be formed in any suitable manner known in the art, including via an adhesive and/or heat fuse.

In contrast to constraining-supply tube 328, cryo-supply tube 324 and guidewire shaft 320 extend freely through, e.g., are not bonded to, outer shaft 316 and into balloon neck 315 of cryoballoon 334. As noted above and with reference to FIG. 3C, a continuous supply of cryofluid exits distal end 325 of cryo-supply tube 324 into the interior of cryoballoon 334 to expand therein. Concurrently, the expanded cryogenic gas proximally exits the interior of cryoballoon 334 via a space between shafts 324, 320 and outer shaft 316, as best shown in FIG. 3C. In an embodiment, a vacuum may be utilized to pull the expanded cryogenic gas out of the catheter although the vacuum is not required for the gas to exit. The expanded cryogenic gas travels proximally through proximal balloon neck 315 and within lumen 318 of outer shaft 316 for the length of catheter 306, and then exits catheter 306 via an arm 309 of hub 308. As shown in the cross-sectional view of FIG. 3D, cryotherapy shaft 324 extends freely through, e.g., is not bonded to, arm 309 and thus the expanded cryogenic gas may escape via an annular lumen or space 311 defined between cryotherapy shaft 324 and arm 309. In another embodiment (not shown), cryotherapy shaft 324 may be bonded or otherwise coupled to one sidewall of outer shaft 316.

FIG. 6 illustrates another embodiment hereof in which the inflation fluid for the constraining balloon may be circulated in order to better control the temperature thereof. More particularly, an ablation assembly 600 includes a cryoballoon 634 and a constraining balloon 636. Cryo-supply tube 624 and guidewire shaft 620 extend through outer shaft 616 and into proximal balloon neck 615 of cryoballoon 634 as described above with respect to catheter 306. However, in this embodiment, constraining-supply tube 628 as well as an inflation fluid return or exhaust shaft 650 extend through outer shaft 616 and into an interior of constraining balloon 636 via proximal balloon neck 617 of constraining balloon 636. Proximal bond 629 surrounds shafts 628, 650 and seals off the interior of constraining balloon 636 from lumen 618 of outer shaft 616. A continuous supply of inflation fluid enters the interior of constraining balloon 636 via constraining-supply tube 628 to inflate and expand constraining balloon 636. The inflation fluid then exits the interior of constraining balloon 636 via exhaust shaft 650 such that the inflation fluid within constraining balloon 636 may be continuously circulated. The continuous circulation allows for the inflation fluid within the interior of constraining balloon 636 to be maintained at a warmer temperature, which improves the ability of constraining balloon 636 to protect non-targeted tissue from ablation because constraining balloon 636 is prevented from cooling to a cryoablation temperature due to heat transfer with cryoballoon 634. The relatively warmer temperature maintained in constraining balloon 636 due to the continuous circulation of inflation fluid also permits improved heat transfer from constraining balloon 636 to cryoballoon 634 to better moderate the temperature of the cryotherapy as described herein.

FIG. 7 illustrates another embodiment hereof in which exhaust from the cryoballoon serves as the inflation fluid for the constraining balloon in order to simplify the construction of the catheter and reduce the required number of lumens, which may also reduce an outer diameter of the catheter. More particularly, an ablation assembly 700 can include a cryoballoon 734 and a constraining balloon 736. Cryo-supply tube 724 and guidewire shaft 720 extend through outer shaft 716 and into proximal balloon neck 715 of cryoballoon 734 as described above with respect to catheter 306. However, in this embodiment, a U-shaped connector 752 fluidly connects the interior of cryoballoon 734 and the interior of constraining balloon 736. The cryogenic agent is delivered into cryoballoon 734 and there is a pressure drop when the cryogenic agent enters the interior of cryoballoon 734 and expands to gas. As the cryogenic agent expands into gas, cryoballoon 734 is expanded and the exhaust gas travels through U-shaped connector 752 and into constraining balloon 736 to expand the constraining balloon. Although the temperature of cryoballoon 734 ablates target tissue in contact with cryoballoon 734, the exhaust gas that leaves cryoballoon 734 and fills constraining balloon 736 can be approximately 20° C. to 50° C. warmer than the temperature of cryoballoon 734. Thus, although the gas exhaust is still cool, the temperature of constraining balloon 736 can remain above −5° C. such that thermal injury of non-targeted tissue adjacent to constraining balloon 736 will not occur. In one embodiment (not shown), the length of U-shaped connector 752 may be increased such that the distal loop extends further distally into blood flow that serves to additionally warm the exhaust gas before it enters the interior of constraining balloon 736. The exhaust gas continues to flow through proximal neck 717 of constraining balloon 736, past proximal bond 729, and proximally exits the catheter through an unsealed arm of the hub in the same way as described above with respect to FIG. 3D.

In another embodiment hereof, the catheter may include two separate guidewire lumens for more controlled positioning of the ablation assembly. Two separate guidewire lumens also allow for two different types of guidewires to be utilized for placement of the catheter. For example, a floppy-tipped guidewire and a stiff-tipped guidewire may both be useful in advancing the catheter through tortuous anatomy. Although only one guidewire is required for positioning the catheter, both guidewires are in place and may be utilized if required. For example, as shown in FIG. 8, FIG. 8A, and FIG. 8B, a dual balloon catheter 806 includes an ablation assembly 800 at a distal end thereof. Ablation assembly 800 includes a cryoballoon 834 and a constraining balloon 836 disposed adjacent, i.e., side-by-side, to cryoballoon 834. A cryo-supply tube 824 and a guidewire shaft 820A extend through an outer shaft 816 and into a proximal balloon neck 815 of cryoballoon 834, in the manner described above with respect to catheter 306. Outer shaft 816 defines a lumen 818 therethrough.

Guidewire shaft 820A defines a guidewire lumen 822A for receiving a guidewire 842A. However in this embodiment, in addition to a constraining-supply tube 828 defining an inflation lumen 830, a second inner guidewire shaft 820B extends through constraining balloon 836. Guidewire shaft 820B defines a guidewire lumen 822B extending substantially the entire length of the catheter for accommodating a second guidewire 842B. Outer shaft 816 has a proximal end 840 that extends out of the patient and is coupled to a hub 808 and a distal end 841 coupled to proximal necks 815, 817 of balloons 834, 836, respectively. Distal ends 819, 821 of balloons 834, 836, respectively, are coupled to guidewire shafts 820A, 820B, respectively. Guidewire shafts 820A, 820B have proximal ends (not shown) coupled to hub 808 and distal ends that terminate distally of balloons 834, 836. Hub 808 includes guidewire port 814A in fluid communication with guidewire lumen 822A of guidewire shaft 820A and a guidewire port 814B in fluid communication with guidewire lumen 822B of guidewire shaft 820B. In addition, hub 808 includes a first inflation port 812 in fluid communication with inflation lumen 830 of constraining-supply tube 828 and a second inflation port 810 in fluid communication with inflation lumen 826 of cryo-supply tube 824. Similar to proximal bond 329 described above, a proximal bond 829 surrounds and seals off an interior of balloon 834 from lumen 818 of outer shaft 816. At the site of proximal bond 829, outer shaft 816 transforms from the annular configuration of FIG. 8A to a generally figure "8" configuration which resembles balloon necks 815, 817.

FIG. 9, FIG. 9A, and FIG. 9B illustrate another embodiment hereof in which the catheter may include two separate guidewire lumens for more controlled positioning of the ablation assembly. In this embodiment, two individual balloon catheters 906A, 906B are coupled together via a coupler sleeve 960. An ablation assembly 900 is formed at the distal end of balloon catheters 906A, 908B, with a cryoballoon 934 disposed at the distal end of balloon catheter 906A and a constraining balloon 936 disposed at the distal end of balloon catheter 906B. The first balloon catheter 906A includes an outer shaft 916A defining a lumen 918A. A cryo-supply tube 924 defining a lumen 926 and a guidewire shaft 920A defining a guidewire lumen 922A for receiving a guidewire 942A both extend through outer shaft 916A. Cryoballoon 934 disposed at the distal end of catheter 906A is inflated with a cryogenic agent as described above with respect to cryoballoon 334. The second balloon catheter 906B includes an outer shaft 916B and an inner guidewire shaft 920B defining a guidewire lumen 922B for receiving a guidewire 942B. In the coaxial catheter construction of second balloon catheter 906B, guidewire shaft 920B extends within outer shaft 916B such that an annular inflation lumen 918B is defined between an inner surface of outer shaft 916B and an outer surface of guidewire shaft 920B. Constraining balloon 936 disposed at the distal end of catheter 906B is inflated via inflation fluid delivered through annular inflation lumen 918B. A first hub 908A is coupled to first balloon catheter 906A and a second hub 908B is coupled to second balloon catheter 906B. Hubs 908A, 908B include guidewire ports 914A, 914B, respectively, in fluid communication with guidewire lumens 922A, 922B of guidewire shafts 920A, 920B and inflation ports 910, 912 in fluid communication with inflation lumens 926, 918B of cryo-supply tube 924 and outer shaft 916B, respectively. In this embodiment, having two separate balloon catheters may simplify the bond area between each catheter and its respective balloon since each outer shaft is bonded to a single proximal balloon neck rather than two bifurcating proximal balloon necks as described with respect to embodiments described above.

Coupler sleeve 960 extends over a portion of catheters 916A, 916B to couple them together and properly position balloons 934, 936 in parallel within a target artery. In an embodiment, coupler sleeve 960 has a length between 10 mm and 30 mm long. Coupler sleeve 960 may be formed from any suitable biocompatible material, including but not limited to polyethylene, polyethylene block amide copolymer (PEBA), polyamide, and/or combinations thereof, which can be laminated, blended, co-extruded, or processed according to another suitable method. Coupler sleeve 960 may have a circular or oval cross-section as shown in FIG. 9B, or may have a profile resembling the figure "8" to reduce the profile thereof. In an embodiment, coupler sleeve 960 may be a removable separate component and an operator may assemble separate balloon catheters 906A, 906B into coupler sleeve 960. As a result, the operator may select appropriate balloon sizes or types to best treat the treatment site. For example, the operator may select a catheter having a constraining balloon with a particular expanded outer diameter and/or length in order to customize the size of the nominal treatment area/ablation pattern. Such customization is useful for accommodating individual anatomy of a patient. In another embodiment, coupler sleeve 960 and balloon catheters 906A, 906B may be formed as a single, integral assembly.

In the embodiments of FIG. 8 and FIG. 9, the distal ends of the cryoballoon and the constraining balloon separately extend in a distal direction and are not joined together. As such, in one embodiment, one or more mechanisms may be utilized to couple the cryoballoon and the constraining balloon together, which may prevent the balloons from folding over one another during deployment. Referring to FIG. 10, in one embodiment, cryoballoon 834/934 and constraining balloon 836/936 are coupled together via an adhesive 1062. In another embodiment shown in FIG. 11, an outer sheath 1164 may be used to hold cryoballoon 834/934 and constraining balloon 836/936 adjacent to one another in a side-by-side configuration during deployment. In one embodiment, outer sheath 1164 is an elastic tubular member which expands as the cryoballoon and the constraining balloon are inflated. Outer sheath 1164 surrounds and constrains the cryoballoon and the constraining balloon to keep them in an adjacent or side-by-side configuration. Outer sheath 1164 is formed of a substantially noninsulative material which does not affect ablation performed by the cryoballoon, such as polyurethane, PEBAX polymer, or silicone. In another embodiment, outer sheath 1164 is not elastic. In yet another embodiment, outer sheath 1164 may comprise one or more annular segments (not shown) rather than a continuous tubular member that covers at least a portion of the cryoballoon and the constraining balloon.

In yet another embodiment, outer sheath 1164 may be closed at the distal end thereof in order to form an outer inflatable balloon which surrounds and constrains cryoballoon 834/934 and constraining balloon 836/936. In addition to keeping cryoballoon 834/934 and constraining balloon 836/936 in an adjacent side-by-side or generally parallel configuration, outer sheath 1164 can occlude blood flow when inflated against the vessel wall. Occlusion of blood flow may be desirable since blood flow past a cryogenic balloon may affect the desired ablation therapy pattern.

In another embodiment hereof, the ablation assembly includes one or more prongs for deflecting the cryogenic balloon away from non-target tissue within a vessel. More particularly, FIG. 12 is a partially schematic cross-sectional view of an artery A having an ablation assembly 1200 deployed therein. Ablation assembly 1200 includes a cryogenic balloon 1234 for ablating tissue and a constraining element 1236 that positions cryogenic balloon 1234 within the artery. In this embodiment, constraining element 1236 is a pair of self-expanding prongs that deflect or offset contact of cryoballoon 1234 against the vessel wall.

Figure 13A:
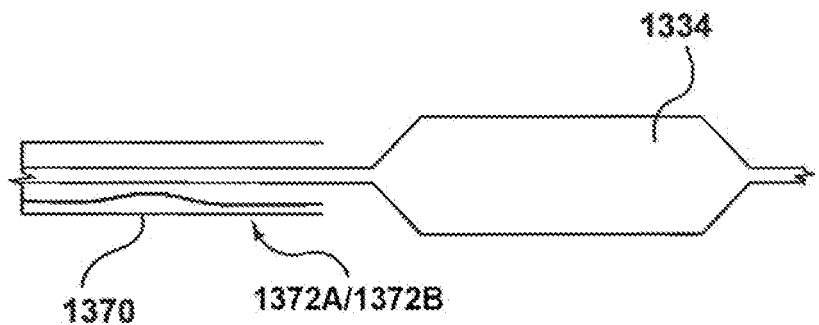
FIG. 13A is a side view of the distal portion of the catheter of FIG. 13, wherein the cryoballoon is in an expanded or inflated configuration and the prongs are constrained within a sheath.
Figure 13B:
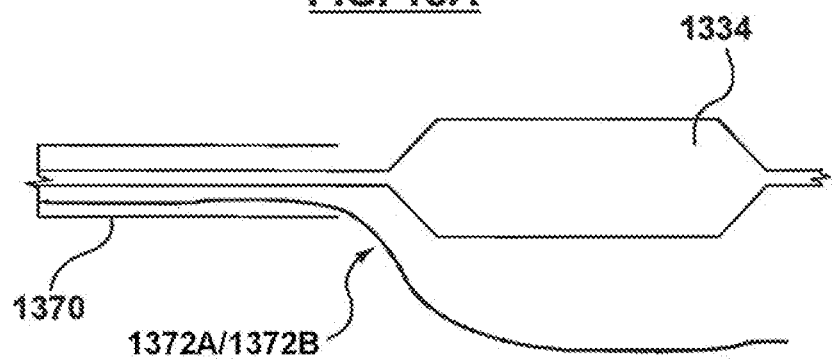
FIG. 13B is a side view of the distal portion of the catheter of FIG. 13, wherein the cryoballoon is in an expanded or inflated configuration and the prongs are released from the sheath.
Figure 13C:
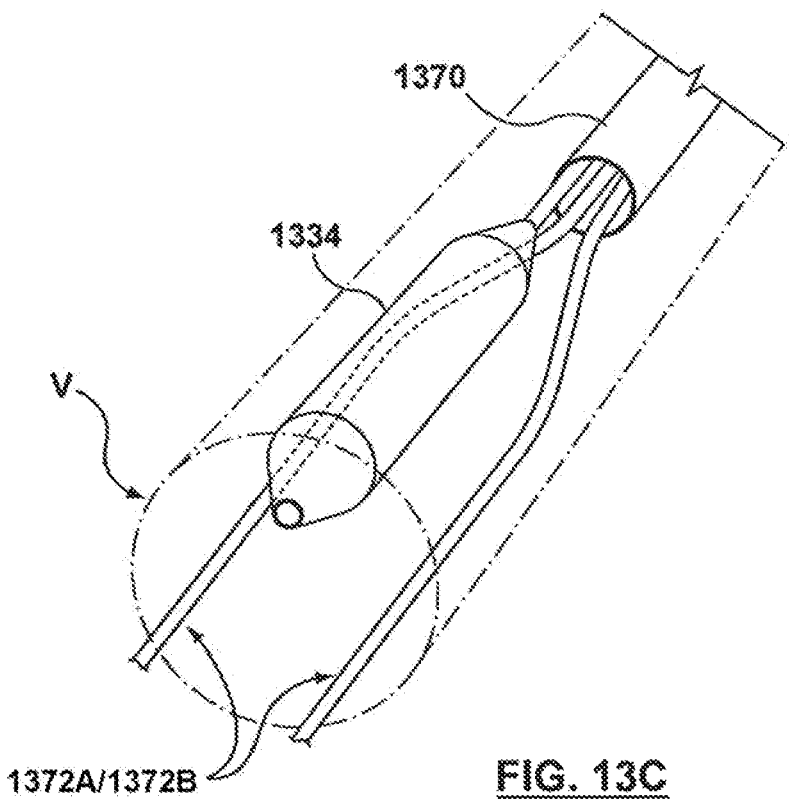
FIG. 13C is an illustrative perspective view of the distal portion of the catheter of FIG. 13 deployed within a vessel, wherein the cryoballoon is in an expanded or inflated configuration and the prongs are released from the sheath.

FIG. 13 is a side view of an example of a catheter system for delivering the self-expanding prongs that deflect a cryoballoon away from non-target tissue of the vessel wall. More particularly, a balloon catheter 1306 includes an outer shaft 1316 defining a lumen (not shown) and an inner guidewire shaft 1320 defining a guidewire lumen (not shown) for receiving a guidewire 1342. In the catheter construction of balloon catheter 1306, a cryogenic inflation shaft (not shown in FIG. 13) similar to cryo-supply tube 324 extends through catheter 1306 for receiving a cryogenic inflation medium to inflate cryogenic balloon 1334. Cryoballoon 1334 is inflated with a cryogenic agent as described above with respect to cryoballoon 334, and expanded cryogenic gas or exhaust exits catheter 1306 via the space defined between an inner surface of outer shaft 1316 and the outer surfaces of guidewire shaft 1320 and the cryogenic inflation shaft. A hub 1308 is disposed at the proximal end of catheter 1306. Hub 1308 includes an inflation port 1310 in fluid communication with the inflation lumen of the cryogenic inflation shaft and a guidewire port 1314 in fluid communication with the guidewire lumen of inner guidewire shaft 1320. An ablation assembly 1300 includes a cryoballoon 1334 and a pair of self-expanding prongs 1372A, 1372B disposed at the distal end of catheter 1306. Only one of the prongs 1372A, 1372B is shown in FIG. 13 and in FIGS. 13A, 13B, and 14, which are described below.

As shown in FIG. 13A, a tubular sheath 1370 is disposed over catheter 1306 (FIG. 13) and constrains the pair of self-expanding prongs 1372A, 1372B into a reduced diameter suitable for delivery within a vasculature. Prongs 1372A, 1372B are coupled to a push-pull wire 1378 (FIG. 13), which proximally extends out of catheter 1306 and can be manipulated by the operator. Push-pull wire 1378 is utilized for distally advancing and proximally retracting prongs 1372A, 1372B within sheath 1370. When distally advanced out of sheath 1370, prongs 1372A, 1372B deploy to an expanded configuration shown in FIG. 13, FIG. 13B, FIG. 13C, FIG. 14, and FIG. 15. For clarity purposes, cryoballoon 1334 is omitted from the side view and bottom/top view of FIG. 14 and FIG. 15, respectively. Cryoballoon 1334 is pushed to one side of a vessel by prongs 1372A, 1372B which press against the opposite side of the artery to result in a partial circumferential ablation pattern. Cryoballoon 1334 is formed from a non-compliant or low-compliant material to prevent it from expanding between prongs 1372A, 1372B and onto the vessel wall. For example, cryoballoon 1334 may be formed from nylon, PEBAX polymer, or polyethylene terephthalate (PET).

Figure 14:
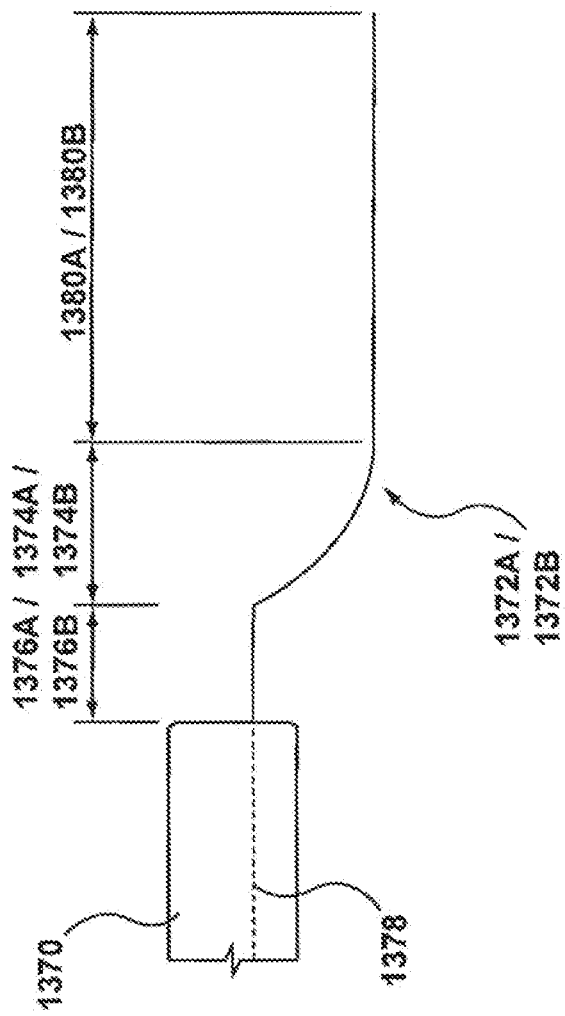
FIG. 14 is a side view of the prongs of FIG. 13, wherein the cryogenic balloon has been omitted for clarity and the prongs are in an expanded or deployed configuration.
Figure 15:
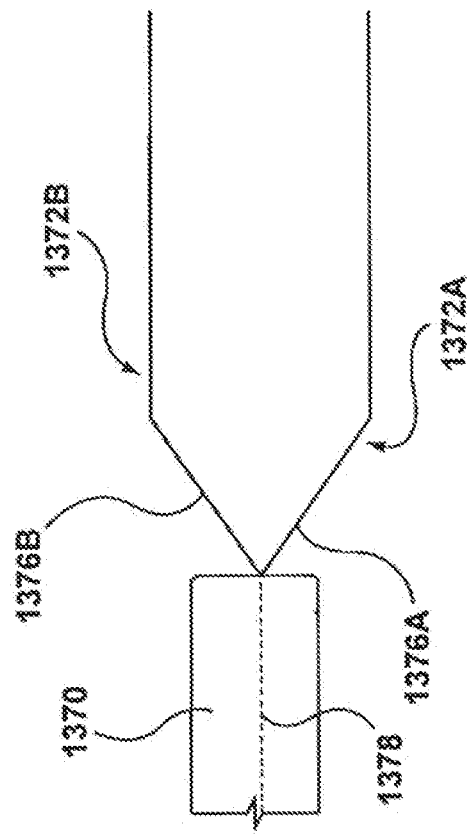
FIG. 15 is a bottom view of the prongs of FIG. 13, wherein the cryogenic balloon has been omitted for clarity and the prongs are in an expanded or deployed configuration.

Referring to FIG. 14 and FIG. 15, each prong 1372A, 1372B includes a proximal segment 1376A, 1376B, a curved segment 1374A, 1374B, and a distal segment 1380A, 1380B. In one embodiment, each prong 1372A, 1372B is a unitary structure formed out of a single or integral piece of material. In another embodiment, the curved segment 1374A, 1374B of each prong is a separate component which may be the same material or a different material that is attached to the proximal and distal segments by any suitable manner known in the art such as for example welding, including resistance welding, friction welding, laser welding or another form of welding, soldering, using an adhesive, adding a connecting element there between, or by another mechanical method. Prongs 1372A, 1372B can be formed from shape memory materials such as a nitinol wire, and can be self-expanding. The nitinol wire may be solid or hollow and may have a circular, oval, square, rectangular, or any other suitable cross-sectional shape.

During delivery, each prong 1372A, 1372B is constrained into a substantially straight configuration within sheath 1370 and when released from sheath 1370, each prong 1372A, 1372B assumes its preformed shape or deployed configuration that presses the outer surface of the balloon against the opposing vessel wall. More particularly, in the deployed configuration, proximal segments 1376A, 1376B are relatively short and substantially straight segments that distally extend from push-pull wire 1378. As shown in the bottom view of FIG. 15, proximal segments 1376A, 1376B diverge in opposing radial directions to place prongs 1372A, 1372B on opposing sides of cryogenic balloon 1334. As shown in the side view of FIG. 14, proximal segments 1376A, 1376B extend within a plane parallel to the longitudinal axis of the vessel. Curved segments 1374A, 1374B distally extend from proximal segments 1376A, 1376B and curve in a radial direction towards the vessel wall. Curved segments 1374A, 1374B operate to contact and push against the proximal portion of cryogenic balloon 1334 to deflect a portion of cryogenic balloon 1334 away from the vessel wall. Generally straight distal segments 1380A, 1380B distally extend from curved segments 1374A, 1374B in a direction parallel to the longitudinal axis of the vessel. Distal segments 1380A, 1380B press and/or lodge prongs 1372A, 1372B against one side of a vessel, while cryogenic balloon 1334 presses against the opposing side of the vessel.

Figure 16:
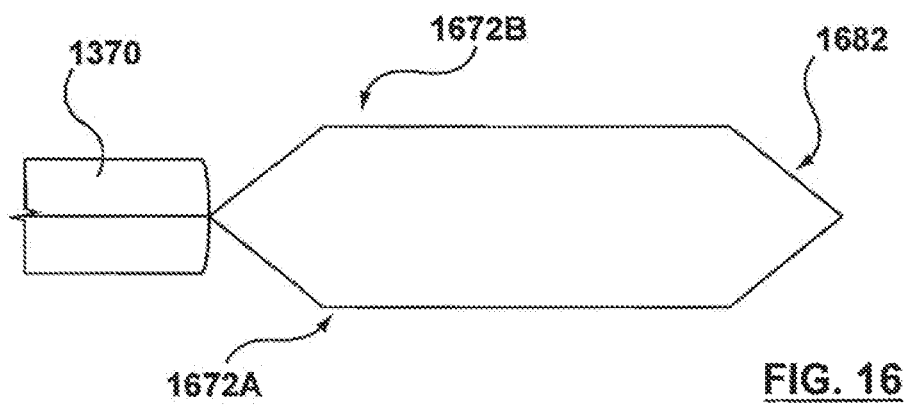
FIG. 16 is a side view of an alternative configuration of self-expanding prongs for deflecting at least a portion of the cryoballoon away from the vessel wall.
Figure 17:
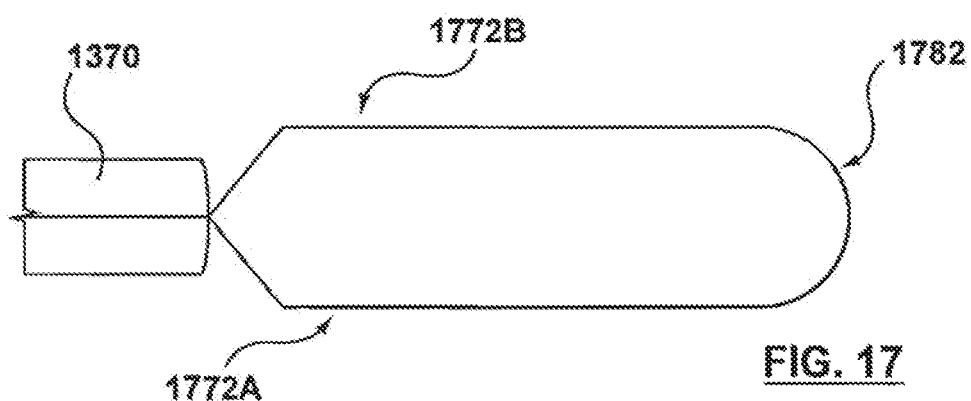
FIG. 17 is a side view of an alternative configuration of self-expanding prongs for deflecting at least a portion of the cryoballoon away from the vessel wall.

In other embodiments, different configurations of self-expanding prongs that deflect cryogenic balloon 1334 away from non-targeted tissue of the vessel wall can be used. For example, FIG. 16 shows prongs 1672A, 1672B having distal ends that are connected via a V-shaped joining segment 1682, and FIG. 17 shows prongs 1772A, 1772B having distal ends that are connected with a rounded U-shaped joining segment 1782. Joining segments 1682, 1782 may be integrally formed between the two prongs, or may be a separate component coupled to the two prongs. Connecting the distal ends of the prongs can essentially form a single prong with improved stability for deflecting a cryoballoon.

Figure 18:
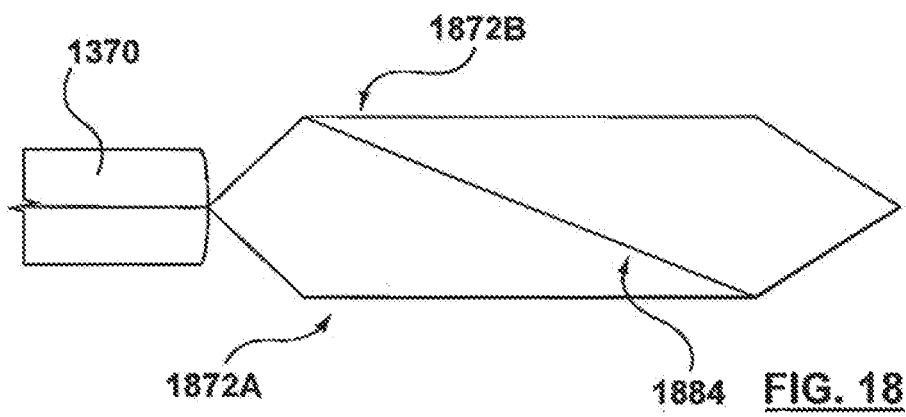
FIG. 18 is a side view of an alternative configuration of self-expanding prongs for deflecting at least a portion of the cryoballoon away from the vessel wall.
Figure 19:
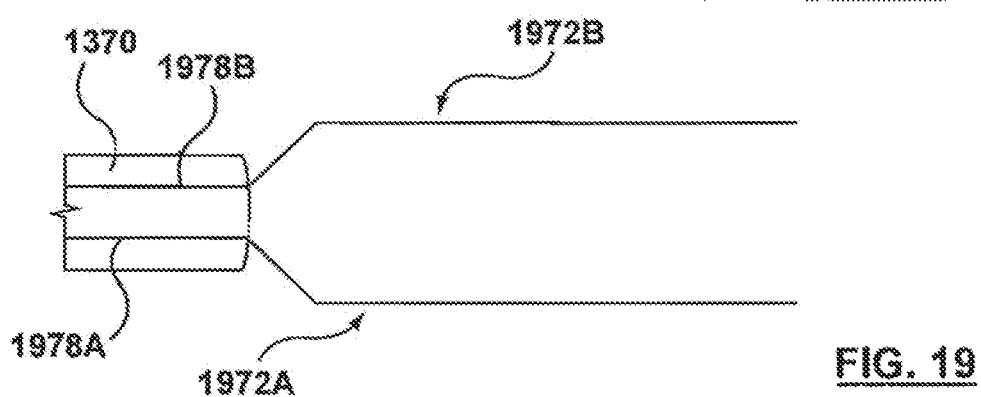
FIG. 19 is a side view of an alternative configuration of self-expanding prongs for deflecting at least a portion of the cryoballoon away from the vessel wall.

Prongs 1872A, 1872B in FIG. 18 are similar to prongs 1672A, 1672B but also include a diagonal support segment 1884 extending therebetween for stabilizing and/or strengthening the deflecting prong. Lastly, it will be understood by those of ordinary skill in the art that alternative deployment mechanisms may be utilized for deploying the deflecting prongs. For example, referring to FIG. 19, each prong 1972A, 1972B may be coupled to a separate push-pull wire 1978A, 1978B for individually controlling deployment of each prong. Separate deployment of each prong 1972A, 1972B provides selective control over the amount of the cryoballoon that is deflected away from the vessel wall, and therefore provides selective control over the ablation therapy pattern. For example, only one of prongs 1972A, 1972B may be deployed for less constraining of the cryoballoon and thus ablation occurring around a greater portion of the circumference of the vessel while both prongs 1972A, 1972B may be deployed for more constraining of the cryoballoon and thus ablation occurring around a lesser portion of the circumference of the vessel. In another embodiment, the deployment of self-expanding prongs may be accomplished and/or assisted by retraction of sheath 1370 as will be understood by those of ordinary skill in the art.

Since blood flow past a cryogenic balloon may affect the desired ablation therapy pattern, any embodiment described herein may include an occlusion balloon or other occlusive device. The occlusive device may be placed concentrically around the ablation assembly as described with respect to the outer sheath of FIG. 11, or may be placed proximal to or distal to the ablation assembly. Further, the occlusive device may be integrally formed on the delivery catheter of the ablation assembly or may be a separate device utilized with the delivery catheter of the ablation assembly.

Some embodiments are described herein with respect to partial circumferential ablation of vessel walls. However, in some applications, it may be desirable to perform full circumferential ablation of vessel walls that is also non-continuous or helical. Non-continuous, full circumferential ablation can include forming two or more partial circumferential ablations that collectively extend around the entire circumference of the vessel wall. Helical, full circumferential ablation can include forming one or more ablations that curve to extend around the entire circumference of the vessel wall without being fully circumferential in any single plane perpendicular to the vessel. The non-continuous or helical nature of these full circumferential ablations can reduce structural changes to any one region of the vessels in comparison to other full circumferential ablations. It will be understood by those of ordinary skill in the art that embodiments hereof for creating partial circumferential ablation patterns may also be utilized for creating non-continuous or helical full circumferential ablation patterns. For example, catheters having ablation assemblies described herein may be longitudinally translated within a vessel and rotated as desired in order to perform multiple, sequential partial circumferential ablations which collectively extend around the entire circumference of the vessel wall. In some embodiments, relatively short balloons having lengths between 2 mm and 5 mm may be rotated and moved longitudinally in a vessel to produce a non-continuous and helical ablation pattern.

EXAMPLES

1. A cryotherapeutic device, comprising:
   an elongated shaft including a distal portion, the shaft configured to locate the distal portion in an anatomical vessel;
   a first balloon at the distal portion;
   a first supply lumen along at least a portion of the shaft;
   a first exhaust lumen along at least a portion of the shaft, the first exhaust lumen fluidly connected to the first supply lumen via the first balloon;
   a second balloon at the distal portion fluidly separate from the first supply lumen and the first exhaust lumen, the second balloon configured to prevent the first balloon from cryogenically cooling a full circumference of a wall of the anatomical vessel in generally any plane perpendicular to a length of the anatomical vessel;
   a second supply lumen along at least a portion of the shaft; and
   a second exhaust lumen along at least a portion of the shaft, the second exhaust lumen fluidly connected to the second supply lumen via the second balloon.
2. The cryotherapeutic device of example 1 wherein—
   the first balloon is non-compliant or semi-compliant, and the second balloon is compliant.
3. The cryotherapeutic device of example 1 wherein—
   the first balloon is less than 10% compliant, and the second balloon is between 50% and 100% compliant.
4. The cryotherapeutic device of example 1 wherein—
   the second balloon includes a proximal portion and a distal portion,
   the second supply lumen includes an opening at one of the proximal and distal portions of the second balloon, and
   the second exhaust lumen includes an opening at the other of the proximal and distal portions of the second balloon.
5. The cryotherapeutic device of example 1 wherein—
   the cryotherapeutic device is configured to cryogenically cool a portion of the wall of the anatomical vessel proximate the first balloon when pressurized refrigerant is delivered to the first balloon through the first supply lumen, expanded in the first balloon, and exhausted from the first balloon through the first exhaust lumen, and
   the cryotherapeutic device is configured to warm the first balloon when a heat-transfer fluid is delivered to the second balloon through the second supply lumen, moved within the second balloon, and exhausted from the second balloon through the second exhaust lumen.
6. A method for treating a patient, comprising:
   locating a distal portion of an elongated shaft of a cryotherapeutic device within an anatomical vessel of the patient;
   delivering refrigerant to a first balloon of the cryotherapeutic device at the distal portion;
   expanding the refrigerant within the first balloon to cool the first balloon;
   cooling a portion of a wall of the anatomical vessel proximate the first balloon; and
   circulating a heat-transfer fluid through a second balloon of the cryotherapeutic device proximate the first balloon and fluidly separate from the first balloon to warm the first balloon and to moderate the cooling of the portion of the wall of the anatomical vessel.
7. The method of example 6 wherein circulating the heat-transfer fluid causes a temperature of the first balloon to be between −10° C. and −40° C.
8. The method of example 6 further comprising contacting between 45° and 225° of the wall of the anatomical vessel with the first balloon.
9. The method of example 6 further comprising—
   semi- or non-compliantly expanding the first balloon with the refrigerant; and compliantly expanding the second balloon with the heat-transfer fluid.

10. The method of example 6 further comprising using the second balloon to prevent the first balloon from cryogenically cooling a full circumference of the wall of the anatomical vessel in generally any plane perpendicular to a length of the anatomical vessel.

11. A cryotherapeutic device, comprising:
a first catheter, including—
   a first elongated shaft having a distal portion,
   a first balloon at the distal portion of the first shaft,
   a supply lumen along at least a portion of the first shaft,
   an exhaust lumen along at least a portion of the first shaft, the exhaust lumen fluidly connected to the supply lumen via the first balloon;
a second catheter, including—
   a second elongated shaft having a distal portion, and
   a second balloon at the distal portion of the second shaft; and
a coupler sleeve configured to be within an anatomical vessel and to receive the first and second catheters in a parallel arrangement.

12. The cryotherapeutic device of example 11, further comprising a third catheter, wherein—
the third catheter includes—
   a third elongated shaft having a distal portion, and
   a third balloon at the distal portion of the third shaft,
the second balloon and the third balloon are configured to expand to different sizes, and
the second and third catheters are interchangeable with respect to the coupler sleeve.

13. The cryotherapeutic device of example 11 further comprising an expandable outer sheath connected to the coupler sleeve, wherein the first and second balloons are configured to fit together within the expandable outer sheath when the first and second catheters are within the coupler sleeve.

14. The cryotherapeutic device of example 11 wherein the cryotherapeutic device is configured to cryogenically cool a portion of a wall of the anatomical vessel proximate the first balloon when pressurized refrigerant is delivered to the first balloon through the first supply lumen, expanded in the first balloon, and exhausted from the first balloon through the first exhaust lumen.

15. The cryotherapeutic device of example 11 wherein the second balloon is configured to prevent the first balloon from cryogenically cooling a full circumference of the wall of the anatomical vessel in generally any plane perpendicular to a length of the anatomical vessel.

16. The cryotherapeutic device of example 11 wherein—
the first catheter includes a first guidewire lumen along at least a portion of the first shaft and extending through the first balloon, and
the second catheter includes a second guidewire lumen along at least a portion of the second shaft and extending through the second balloon.

17. A method for treating a patient, comprising:
locating a distal portion of a first elongated shaft of a first catheter within an anatomical vessel of the patient;
delivering refrigerant to a first balloon of the first catheter at the distal portion of the first shaft;
expanding the refrigerant within the first balloon to cool the first balloon;
cooling a portion of a wall of the anatomical vessel proximate the first balloon;
selecting a second catheter from a plurality of catheters based on a size of the anatomical vessel and a size of a second balloon of the second catheter;
locating a distal portion of a second elongated shaft of the second catheter within the anatomical vessel proximate the first distal portion of the first elongated shaft, the second balloon being at the distal portion of the second elongated shaft; and
expanding the second balloon between the first balloon and the wall of the anatomical vessel to prevent the first balloon from cryogenically cooling a full circumference of the wall of the anatomical vessel in generally any plane perpendicular to a length of the anatomical vessel.

18. The method of example 17 wherein locating the distal portion of the first shaft and locating the distal portion of the second shaft are generally simultaneous.

19. The method of example 17 further comprising coupling the first and second catheters after selecting the second catheter.

20. The method of example 19 wherein coupling the first and second catheters includes introducing the first and second catheters into a coupler sleeve.

21. A cryotherapeutic device, comprising:
an elongated shaft including a distal portion, the shaft configured to locate the distal portion in an anatomical vessel;
an elongated balloon at the distal portion;
a supply lumen along at least a portion of the shaft;
an exhaust lumen along at least a portion of the shaft, the exhaust lumen fluidly connected to the supply lumen via the balloon; and
an elongated, self-expanding prong at the distal portion, wherein—
   the balloon is configured to preferentially expand away from the prong, and
   the prong is configured to prevent the balloon from cryogenically cooling a full circumference of a wall of the anatomical vessel in generally any plane perpendicular to a length of the anatomical vessel.

22. The cryotherapeutic device of example 21 wherein the balloon is non-compliant or semi-compliant.

23. The cryotherapeutic device of example 21 wherein the balloon is less than 10% compliant.

24. The cryotherapeutic device of example 21 wherein—
the prong is a first prong,
the cryotherapeutic device further comprises a second prong, and
the first and second prongs are deployable independently or together to change the size of a portion of the anatomical vessel cryogenically cooled by the balloon.

25. The cryotherapeutic device of example 21 wherein—
the prong is a first prong,
the cryotherapeutic device further comprises a second prong, and
the first and second prongs are proximally connected to a push/pull wire.

26. The cryotherapeutic device of example 25 wherein—
the first and second prongs are distally connected, and
the cryotherapeutic device further comprises a diagonal support between the first and second prongs.

27. A method for treating a patient, comprising:
locating a distal portion of an elongated shaft of a catheter within an anatomical vessel of the patient;
pressing an elongated prong at the distal portion of the shaft against a first portion of a wall of the anatomical vessel, delivering refrigerant to a balloon of the catheter at the distal portion of the shaft to cool the balloon and to preferentially expand the balloon in a radial direction away from the prong; and cooling a second portion of the wall of the anatomical vessel proximate the balloon, wherein the prong urges the balloon against the second portion of the wall of the anatomical vessel and spaces the balloon apart from the first portion of the wall of the anatomical vessel.

28. The method of example 27 wherein the first and second portions of the wall of the anatomical vessel are at generally opposite sides of the wall of the anatomical vessel.

29. The method of example 27 wherein delivering refrigerant to the balloon non-compliantly or semi-compliantly expands the balloon.

30. The method of example 27 further comprising controlling deflection of the prong to control the size of the second portion of the wall of the anatomical vessel.

31. The method of example 27 further comprising selecting a number of elongated prongs at the distal portion of the shaft to press against the first portion of the wall of the anatomical vessel to control the size of the second portion of the wall of the anatomical vessel.

CONCLUSION

While various embodiments according to the present technology have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described embodiments. It will also be understood that each feature of each embodiment discussed herein, and of each reference cited herein, can be used in combination with the features of any other embodiment. All patents and publications discussed herein are incorporated by reference herein in their entirety.

Where the context permits, singular or plural terms may also include the plural or singular terms, respectively. Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the terms "comprising" and the like are used throughout the disclosure to mean including at least the recited feature(s) such that any greater number of the same feature(s) and/or additional types of other features are not precluded. It will also be appreciated that various modifications may be made to the described embodiments without deviating from the present technology. Further, while advantages associated with certain embodiments of the present technology have been described in the context of those embodiments, other embodiments may also exhibit such advantages, and not all embodiments need necessarily exhibit such advantages to fall within the scope of the present technology. Accordingly, the disclosure and associated technology can encompass other embodiments not expressly shown or described herein.

We claim:

1. A cryotherapeutic device, comprising:
an elongate shaft having a distal end portion, wherein the shaft is configured to locate its distal end portion at a treatment site within an anatomical lumen of a human patient;
a first balloon at the distal end portion of the shaft, wherein the first balloon includes a flexible wall defining an expandable interior volume;
a first supply lumen carried by the shaft;
a first exhaust lumen carried by the shaft, wherein the first exhaust lumen is fluidly connected to the first supply lumen via the interior volume of the first balloon;
a second balloon at the distal end portion of the shaft, wherein the second balloon includes a flexible wall defining an expandable interior volume fluidly separate from the first supply lumen and from the first exhaust lumen, and wherein the second balloon is configured to prevent the first balloon from contacting a full circumference of a wall of the anatomical lumen in any plane perpendicular to a length of the anatomical lumen;
a second supply lumen carried by the shaft; and
a second exhaust lumen carried by the shaft, wherein the second exhaust lumen is fluidly connected to the second supply lumen via the interior volume of the second balloon, and wherein the respective interior volumes of the first and second balloons are non-overlapping.

2. The cryotherapeutic device of claim 1 wherein:
the wall of the first balloon is non-compliant or semi-compliant; and
the wall of the second balloon is compliant.

3. The cryotherapeutic device of claim 1 wherein:
the wall of the first balloon is less than 10% compliant; and
the wall of the second balloon is between 50% and 100% compliant.

4. The cryotherapeutic device of claim 1 wherein:
the second supply lumen includes an opening at a proximal portion of the interior volume of the second balloon; and
the second exhaust lumen includes an opening at a distal portion of the interior volume of the second balloon.

5. The cryotherapeutic device of claim 1 wherein:
the cryotherapeutic device is configured to cryogenically cool a first portion of the wall of the anatomical lumen via the wall of the first balloon when pressurized refrigerant is delivered to the interior volume of the first balloon through the first supply lumen, expanded in the interior volume of the first balloon, and exhausted from the interior volume of the first balloon through the first exhaust lumen; and
the cryotherapeutic device is configured to warm a second portion of the wall of the anatomical lumen via the wall of the second balloon when a heat-transfer fluid is delivered to the interior volume of the second balloon through the second supply lumen, moved within the interior volume of the second balloon, and exhausted from the interior volume of the second balloon through the second exhaust lumen.

6. The cryotherapeutic device of claim 1 wherein the first balloon and the second balloon are configured to be disposed in parallel at the treatment site.

7. The cryotherapeutic device of claim 1 wherein the first balloon and the second balloon are coextruded.

8. The cryotherapeutic device of claim 1 wherein the wall of the first balloon includes polyethylene block amide copolymer (PEBA) or nylon.

9. The cryotherapeutic device of claim 8 wherein the wall of the second balloon includes polyurethane or silicone.

10. The cryotherapeutic device of claim 1 wherein the wall of the first balloon and the wall of the second balloon are made of different materials.

11. The cryotherapeutic device of claim 1 wherein the first balloon and the second balloon are configured to be disposed side-by-side at the treatment site.

12. A method for treating a patient, the method comprising:
- locating a distal end portion of an elongate shaft of a cryotherapeutic device at a treatment site within an anatomical lumen of the patient;
- supplying refrigerant to a first balloon of the cryotherapeutic device at the distal end portion of the shaft;
- expanding the refrigerant within an interior volume defined by a flexible wall of the first balloon;
- cooling a first portion of a wall of the anatomical lumen via the wall of the first balloon;
- supplying heat-transfer fluid to a second balloon of the cryotherapeutic device at the distal end portion of the shaft;
- flowing the heat-transfer fluid through an interior volume defined by a flexible wall of the second balloon, wherein the respective interior volumes of the first and second balloons are non-overlapping while flowing the heat-transfer fluid through the interior volume of the second balloon; and
- warming a second portion of the wall of the anatomical lumen via the wall of the second balloon,
- wherein a plane perpendicular to a length of the anatomical lumen intersects the first balloon, the second balloon, the first portion of the wall of the anatomical lumen, and the second portion of the wall of the anatomical lumen while cooling the first portion of the wall of the anatomical lumen and while warming the second portion of the wall of the anatomical lumen.

13. The method of claim 12 wherein the first portion of the wall of the anatomical lumen encompasses between 45° and 225° of a circumference of the anatomical lumen.

14. The method of claim 12, further comprising:
- semi- or non-compliantly expanding the first balloon with the refrigerant; and
- compliantly expanding the second balloon with the heat-transfer fluid.

15. The method of claim 12 wherein the second balloon prevents the first balloon from contacting a full circumference of the wall of the anatomical lumen in any plane perpendicular to the length of the anatomical lumen while cooling the first portion of the wall of the anatomical lumen and while warming the second portion of the wall of the anatomical lumen.

16. The method of claim 12 wherein flowing the heat-transfer fluid through the interior volume of the second balloon includes continuously circulating the heat-transfer fluid through the interior volume of the second balloon while warming the second portion of the wall of the anatomical lumen.

17. The method of claim 12 wherein cooling the first portion of the wall of the anatomical lumen and warming the second portion of the wall of the anatomical lumen include cooling the first portion of the wall of the anatomical lumen and warming the second portion of the wall of the anatomical lumen while the first and second balloons are disposed in parallel at the treatment site.

18. The method of claim 12 wherein cooling the first portion of the wall of the anatomical lumen and warming the second portion of the wall of the anatomical lumen include cooling the first portion of the wall of the anatomical lumen and warming the second portion of the wall of the anatomical lumen while the first and second balloons are disposed side-by-side at the treatment site.

19. The method of claim 12 wherein warming the second portion of the wall of the anatomical lumen prevents the first balloon from contacting a full circumference of the wall of the anatomical lumen in any plane perpendicular to the length of the anatomical lumen.

* * * * *